US011008555B2

(12) United States Patent
Oakes et al.

(10) Patent No.: US 11,008,555 B2
(45) Date of Patent: May 18, 2021

(54) VARIANT CAS9 POLYPEPTIDES COMPRISING INTERNAL INSERTIONS

(71) Applicant: The Regents of the University of California, Oakland, CA (US)

(72) Inventors: Benjamin Oakes, Berkeley, CA (US); David Savage, Berkeley, CA (US); Dana Nadler, Berkeley, CA (US); Abraham I. Flamholz, Berkeley, CA (US); Jennifer A. Doudna, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/751,432

(22) PCT Filed: Sep. 15, 2016

(86) PCT No.: PCT/US2016/051958
§ 371 (c)(1),
(2) Date: Feb. 8, 2018

(87) PCT Pub. No.: WO2017/048969
PCT Pub. Date: Mar. 23, 2017

(65) Prior Publication Data

US 2020/0199552 A1 Jun. 25, 2020

Related U.S. Application Data

(60) Provisional application No. 62/220,161, filed on Sep. 17, 2015.

(51) Int. Cl.

| | |
|---|---|
| ***C12N 9/22*** | (2006.01) |
| ***C12N 15/113*** | (2010.01) |
| ***C07K 14/72*** | (2006.01) |

(52) U.S. Cl.
CPC .............. *C12N 9/22* (2013.01); *C07K 14/721* (2013.01); *C12N 15/113* (2013.01); *C07K 2319/00* (2013.01)

(58) Field of Classification Search
CPC ......... C12N 9/22; C12N 15/113; C07K 14/72
See application file for complete search history.

(56) References Cited

U.S. PATENT DOCUMENTS

2015/0024500 A1 1/2015 Yu et al.

FOREIGN PATENT DOCUMENTS

| | | |
|---|---|---|
| WO | WO 2014/093712 A1 | 6/2014 |
| WO | WO 2015/089486 A2 | 6/2015 |
| WO | WO 2015/103153 A1 | 7/2015 |
| WO | WO 2016/196655 A1 | 12/2016 |
| WO | WO 2016/205759 A1 | 12/2016 |

OTHER PUBLICATIONS

Davis et al. Online Apr. 6, 2015; Small-molecule triggered Cas9 protein with improved genome-editing specificity. Nat. Chem. Biol. 11(5): 316-318.*
Oakes et al. 2016; Profiling of engineering hotspots identifies an allosteric CRISPR-Cas9 switch. Nature Biotechnology. 34(6): 646-651 plus online methods.*
Oakes, et al.; "Protein Engineering of Cas9 for Enhanced Function"; Methods of Enzymology; vol. 546, pp. 491-511 (2014).
Oakes, et al.; "Profiling of engineering hotspots identifies an allosteric CRISPR-Cas9 switch"; Nature Biotechnology; 8 pages (May 2, 2016).

* cited by examiner

*Primary Examiner* — Karen Cochrane Carlson
(74) *Attorney, Agent, or Firm* — Bozicevic Field & Francis, LLP; Paula A. Borden

(57) ABSTRACT

The present disclosure provides variant Cas9 polypeptides, where a variant Cas9 polypeptide of the present disclosure comprises an internal insertion of a heterologous polypeptide. The present disclosure provides nucleic acids comprising nucleotide sequences encoding the variant Cas9 polypeptides. The present disclosure provides host cells comprising a variant Cas9 polypeptide of the present disclosure, or comprising a nucleic acid encoding a variant Cas9 polypeptide of the present disclosure. The present disclosure provides methods of binding and/or modifying a target nucleic acid, involving use of a variant Cas9 polypeptide of the present disclosure.

14 Claims, 40 Drawing Sheets

Specification includes a Sequence Listing.

β -E: (Estrogen)

4-HT(4-Hydroxytamoxifen)

FIG. 13B
9926 bp
dCas9
ER-LBD
FLAG
chicken β-actin promoter
U6 promoter
new sgRNA #10
ori
AmpR
AmpR promoter
f1 ori
AAV2 ITR
bGH poly(A) signal
mCherry
T2A
dCas9
1000
2000
3000
4000
5000
6000
7000
8000
9000

Fig. 14A, cont.
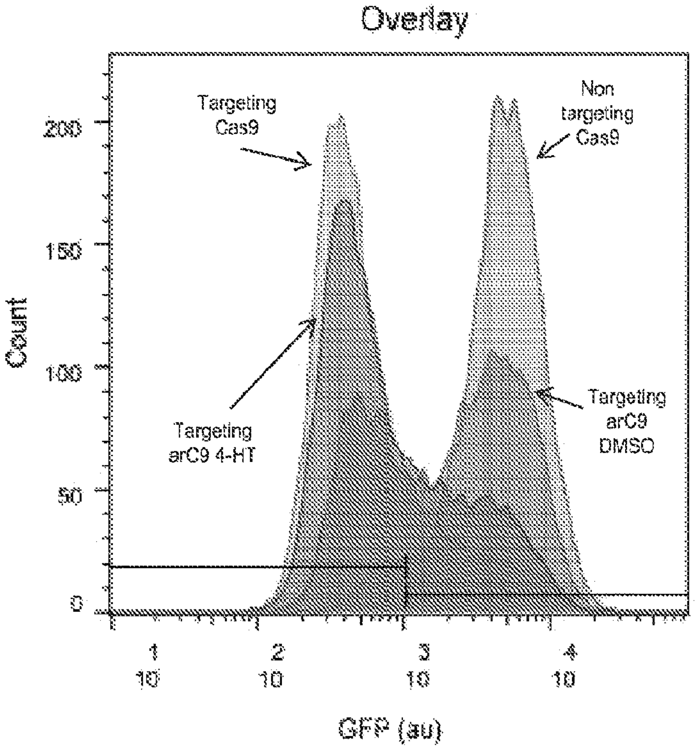

Fig. 18A

```
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD             1368
(SEQ ID NO:5)
```

Fig. 18B

```
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD             1368
(SEQ ID NO:1078)
```

Fig. 19A

Table 1.

| Site in Cas9 | Log2 fold change |
|---|---|
| 1018 | inf |
| 195 | inf |
| 1369 | 6.537581 |
| 1244 | 5.90856 |
| 202 | 5.880755 |
| 208 | 5.725993 |
| 468 | 5.546104 |
| 1058 | 5.47677 |
| 209 | 5.462511 |
| 211 | 5.314298 |
| 1052 | 5.255898 |
| 204 | 5.120876 |
| 1027 | 5.028689 |
| 588 | 4.702083 |
| 238 | 4.656574 |
| 1071 | 4.610846 |
| 228 | 4.594095 |
| 460 | 4.41714 |
| 804 | 4.355887 |
| 802 | 4.283583 |
| 193 | 4.195801 |
| 1156 | 4.184407 |
| 1243 | 4.089836 |
| 1287 | 4.060985 |
| 1064 | 4.047255 |
| 4 | 4.010276 |
| 1191 | 4.004418 |
| 1282 | 3.992484 |
| 1206 | 3.971253 |
| 1251 | 3.960973 |
| 1153 | 3.955239 |
| 390 | 3.840531 |
| 1212 | 3.809598 |
| 1228 | 3.780341 |
| 1155 | 3.761442 |
| 536 | 3.76125 |
| 257 | 3.705058 |
| 112 | 3.656396 |

| Site in Cas9 | Log2 fold change |
|---|---|
| 259 | 3.649234 |
| 577 | 3.623236 |
| 1073 | 3.61586 |
| 1252 | 3.592049 |
| 456 | 3.591599 |
| 944 | 3.584317 |
| 798 | 3.5065 |
| 576 | 3.47602 |
| 205 | 3.457409 |
| 1367 | 3.39478 |
| 689 | 3.37754 |
| 1204 | 3.360447 |
| 690 | 3.35676 |
| 1300 | 3.345254 |
| 231 | 3.342111 |
| 1207 | 3.33079 |
| 467 | 3.312679 |
| 1194 | 3.291399 |
| 214 | 3.286094 |
| 719 | 3.268878 |
| 1012 | 3.236734 |
| 579 | 3.224255 |
| 1050 | 3.113719 |
| 1063 | 3.090399 |
| 1260 | 3.059211 |
| 1253 | 3.058898 |
| 533 | 3.053918 |
| 1291 | 3.028422 |
| 1056 | 3.024106 |
| 313 | 3.007244 |
| 206 | 2.990492 |
| 1196 | 2.965823 |
| 639 | 2.940872 |
| 1010 | 2.895731 |
| 1262 | 2.871035 |
| 721 | 2.862704 |
| 1068 | 2.833959 |
| 1295 | 2.812824 |
| 1188 | 2.807493 |

Fig. 19B

| Site in Cas9 | Log2 fold change |
|---|---|
| 952 | 2.795347 |
| 1240 | 2.79077 |
| 1205 | 2.789325 |
| 1016 | 2.757925 |
| 940 | 2.754248 |
| 1294 | 2.753419 |
| 474 | 2.728515 |
| 1015 | 2.723671 |
| 1304 | 2.707897 |
| 1053 | 2.705848 |
| 647 | 2.691099 |
| 1022 | 2.684456 |
| 1239 | 2 .681188 |
| 1293 | 2.681075 |
| 1306 | 2.670753 |
| 1267 | 2.665259 |
| 1062 | 2.657491 |
| 1183 | 2.642133 |
| 1250 | 2.609533 |
| 1189 | 2.580186 |
| 1347 | 2.576579 |
| 1346 | 2.573419 |
| 1302 | 2.567642 |
| 207 | 2.54121 |
| 1070 | 2.519385 |
| 42 | 2.504722 |
| 1230 | 2.502407 |
| 1237 | 2.492178 |
| 717 | 2.455672 |
| 1061 | 2.433091 |
| 1195 | 2.430744 |
| 1268 | 2.410116 |
| 470 | 2.400358 |
| 1363 | 2.382656 |
| 1248 | 2.374777 |
| 1269 | 2.339512 |
| 1366 | 2.334839 |
| 1190 | 2.314143 |
| 1289 | 2.31364 |

| Site in Cas9 | Log2 fold change |
|---|---|
| 1299 | 2.280437 |
| 1149 | 2.271431 |
| 1348 | 2.249434 |
| 641 | 2.224144 |
| 532 | 2.219087 |
| 1259 | 2.213163 |
| 947 | 2.18174 |
| 1270 | 2.176901 |
| 687 | 2.160619 |
| 127 | 2.132743 |
| 1145 | 2.129331 |
| 1047 | 2.11518 |
| 1298 | 2.109966 |
| 197 | 2.104738 |
| 1054 | 2.077985 |
| 1360 | 2.069469 |
| 1229 | 2.033288 |
| 713 | 2.016597 |
| 692 | 1.978763 |
| 1065 | 1.967878 |
| 1197 | 1.95762 |
| 1034 | 1.944992 |
| 1049 | 1.933411 |
| 834 | 1.918002 |
| 1296 | 1.915903 |
| 3 | 1.848453 |
| 1283 | 1.836786 |
| 868 | 1.817833 |
| 715 | 1.80892 |
| 1247 | 1.806032 |
| 1186 | 1.774574 |
| 1242 | 1.768939 |
| 1238 | 1.768871 |
| 1284 | 1.743205 |
| 645 | 1.726138 |
| 1051 | 1.712075 |
| 217 | 1.699377 |
| 801 | 1.688054 |
| 1213 | 1.681946 |

Fig. 19C

| Site in Cas9 | Log2 fold change |
|---|---|
| 1234 | 1.672037 |
| 1152 | 1.634558 |
| 724 | 1.599034 |
| 1179 | 1.597579 |
| 1233 | 1.569233 |
| 1344 | 1.535246 |
| 941 | 1.480935 |
| 1160 | 1.470846 |
| 1026 | 1.456162 |
| 1246 | 1.439117 |
| 1148 | 1.432723 |
| 1175 | 1.39704 |
| 890 | 1.385042 |
| 1046 | 1.310135 |
| 1307 | 1.288956 |
| 1193 | 1.276877 |
| 1161 | 1.262313 |
| 1255 | 1.220555 |
| 1292 | 1.197644 |
| 1011 | 1.165218 |
| 1031 | 1.161142 |
| 1281 | 1.142497 |
| 1144 | 0.98377 |
| 1150 | 0.934458 |
| 1170 | 0.920757 |
| 648 | 0.786469 |
| 722 | 0.67588 |
| 1286 | 0.639105 |
| 953 | 0.611701 |

Fig. 20A

Table 2.

| Site in Cas9 | Sequences in Cas 9 flanking an heterologous polypeptide inserted at the site | | | |
|---|---|---|---|---|
| | N-term* | SEQ ID NO: | C-Term | SEQ ID NO: |
| 3 | MDK | | KYSI | 1129 |
| 4 | DKK | | YSI | |
| 42 | KKF | | KVLG | 1130 |
| 112 | EDKK | 1131 | HER | |
| 127 | EVA | | YHE | |
| 193 | TYN | | QLFE | 1132 |
| 197 | LFE | | ENP | |
| 202 | PIN | | ASG | |
| 204 | NAS | | GVD | |
| 205 | ASG | | VDA | |
| 206 | SGV | | DAK | |
| 207 | GVD | | AKA | |
| 208 | VDA | | KAIL | 1133 |
| 209 | VDAK | 1134 | AILS | 1135 |
| 211 | AKAI | 1136 | LSAR | 1137 |
| 214 | ILSA | 1138 | RLSK | 1139 |
| 217 | RLS | | KSR | |
| 228 | IAQ | | LPG | |
| 231 | LPG | | EKK | |
| 238 | GLF | | GNL | |
| 257 | NFD | | LAE | |
| 259 | DLA | | EDA | |
| 313 | EIT | | KAP | |
| 390 | ELL | | VKL | |
| 456 | PLA | | RGN | |
| 460 | GNS | | RFA | |
| 467 | MTR | | KSEE | 1140 |
| 468 | TRK | | SEET | 1141 |
| 470 | KSE | | ETI | |
| 474 | TIT | | PWN | |
| 532 | VTE | | GMR | |
| 533 | TEG | | MRK | |
| 536 | MRK | | PAF | |
| 576 | CFD | | SVE | |
| 577 | FDS | | VEI | |
| 579 | SVE | | ISG | |
| 588 | RFN | | ASL | |
| 639 | FEDR | 1142 | EMI | |
| 641 | REM | | IEER | 1143 |
| 645 | EER | | LKT | |
| 647 | ERLK | 1144 | TYA | |
| 687 | SDG | | FAN | |
| 689 | GFA | | NRN | |
| 690 | FAN | | RNF | |
| 692 | NRN | | FMQ | |
| 713 | AQV | | SGQ | |
| 715 | VSG | | QGD | |
| 717 | GQG | | DSL | |
| 719 | GDS | | LHE | |
| 721 | SLH | | EHI | |
| 724 | EHI | | ANLA | 1145 |
| 798 | ILKE | 1146 | HPV | |
| 801 | HPV | | ENT | |
| 802 | PVE | | NTQ | |
| 804 | ENT | | QLQ | |
| 834 | NRLS | 1147 | DYD | |
| 868 | GKSD | 1148 | NVP | |
| 890 | NAK | | LIT | |
| 940 | RMN | | TKY | |
| 941 | MNT | | KYD | |
| 944 | KYD | | END | |
| 947 | END | | KLIR | 1149 |
| 952 | IRE | | VKV | |
| 1010 | FVY | | GDY | |
| 1011 | VYG | | DYK | |
| 1012 | YGD | | YKV | |
| 1015 | DYKV | 1150 | YDV | |
| 1016 | KVY | | DVR | |
| 1022 | KMI | | AKS | |
| 1026 | AKSE | 1151 | QEI | |
| 1027 | SEQ | | EIG | |
| 1031 | IGK | | ATA | |
| 1034 | ATA | | KYFF | 1152 |

Fig. 20B

| Site in Cas9 | Sequences in Cas 9 flanking an heterologous polypeptide inserted at the site | | | |
|---|---|---|---|---|
| | N-term* | SEQ ID NO: | C-Term | SEQ ID NO: |
| 1046 | NFF | | KTEI | 1153 |
| 1047 | FFK | | TEIT | 1154 |
| 1049 | KTE | | ITL | |
| 1050 | KTEI | 1155 | TLA | |
| 1051 | KTEIT | 1156 | LAN | |
| 1052 | EITL | 1157 | ANG | |
| 1053 | TLA | | NGEI | 1158 |
| 1054 | LAN | | GEIR | 1159 |
| 1056 | NGE | | IRK | |
| 1058 | EIR | | KRP | |
| 1061 | KRP | | LIE | |
| 1062 | RPL | | IET | |
| 1063 | PLI | | ETN | |
| 1064 | PLIE | 1160 | TNG | |
| 1065 | IET | | NGE | |
| 1068 | TNGE | 1161 | TGE | |
| 1070 | ETG | | EIV | |
| 1071 | TGE | | IVW | |
| 1073 | EIV | | WDK | |
| 1145 | VLV | | VAK | |
| 1148 | VAK | | VEK | |
| 1149 | VAKV | 1162 | EKG | |
| 1152 | EKG | | KSK | |
| 1153 | KGK | | SKK | |
| 1155 | GKSK | 1163 | KLKS | 1164 |
| 1156 | KSKK | 1165 | LKS | |
| 1160 | KSV | | KEL | |
| 1161 | SVK | | ELL | |
| 1175 | SFE | | KNP | |
| 1179 | KNPI | 1166 | DFL | |
| 1183 | FLE | | AKG | |
| 1186 | AKG | | YKE | |
| 1188 | GYK | | EVK | |
| 1189 | GYKE | 1167 | VKK | |
| 1190 | KEV | | KKD | |
| 1191 | KEVK | 1168 | KDL | |
| 1193 | VKKD | 1169 | LII | |

| Site in Cas9 | Sequences in Cas 9 flanking an heterologous polypeptide inserted at the site | | | |
|---|---|---|---|---|
| | N-term* | SEQ ID NO: | C-Term | SEQ ID NO: |
| 1194 | KDL | | IIK | |
| 1195 | DLI | | IKL | |
| 1196 | LII | | KLP | |
| 1197 | LIIK | 1170 | LPK | |
| 1204 | SLF | | ELE | |
| 1205 | SLFE | 1171 | LEN | |
| 1206 | FEL | | ENG | |
| 1207 | ELE | | NGR | |
| 1212 | GRKR | 1172 | MLA | |
| 1213 | KRM | | LASA | 1173 |
| 1228 | ELAL | 1174 | PSK | |
| 1229 | ALP | | SKY | |
| 1230 | LPS | | KYV | |
| 1233 | SKYV | 1175 | NFL | |
| 1234 | YVN | | FLY | |
| 1237 | FLY | | LAS | |
| 1238 | FLYL | 1176 | ASH | |
| 1239 | LYLA | 1177 | SHY | |
| 1240 | YLAS | 1178 | HYE | |
| 1242 | SHY | | EKL | |
| 1243 | HYE | | KLK | |
| 1244 | YEK | | LKG | |
| 1246 | EKLK | 1179 | GSP | |
| 1247 | LKG | | SPE | |
| 1248 | KGS | | PED | |
| 1250 | SPE | | DNE | |
| 1251 | PED | | NEQ | |
| 1252 | EDN | | EQK | |
| 1253 | EDNE | 1180 | QKQ | |
| 1255 | NEQK | 1181 | QLF | |
| 1259 | LFV | | EQH | |
| 1260 | FVE | | QHK | |
| 1262 | EQH | | KHY | |
| 1267 | YLD | | EII | |
| 1268 | LDE | | IIE | |
| 1269 | DEI | | IEQ | |
| 1270 | EII | | EQI | |

Fig. 20C

| Site in Cas9 | Sequences in Cas 9 flanking an heterologous polypeptide inserted at the site | | | |
|---|---|---|---|---|
| | N-term* | SEQ ID NO: | C-Term | SEQ ID NO: |
| 1281 | RVI | | LAD | |
| 1282 | VIL | | ADA | |
| 1283 | ILA | | DAN | |
| 1284 | LAD | | ANL | |
| 1287 | DANL | 1182 | DKV | |
| 1289 | NLDK | 1183 | VLS | |
| 1291 | DKVL | 1184 | SAY | |
| 1292 | DKVLS | 1185 | AYN | |
| 1293 | VLSA | 1186 | YNK | |
| 1294 | SAY | | NKH | |
| 1295 | AYN | | KHR | |
| 1296 | YNK | | HRD | |
| 1298 | KHR | | DKP | |
| 1299 | HRD | | KPI | |
| 1300 | HRDK | 1187 | PIR | |
| 1302 | DKPI | 1188 | REQ | |
| 1304 | PIRE | 1189 | QAE | |
| 1306 | EQA | | ENI | |
| 1307 | QAE | | NII | |
| 1344 | VLD | | ATL | |
| 1346 | DAT | | LIH | |
| 1347 | ATL | | IHQ | |
| 1348 | TLI | | HQS | |
| 1360 | TRI | | DLS | |
| 1363 | DLS | | QLG | |
| 1366 | QLG | | GD | |
| 1367 | LGG | | D | |
| 1369 | | | | |

*The last amino acid of the Cas9 sequence flanking the heterologous peptide at the N-terminal end, if it is L, M, Q, K, E, W, or R may be substituted with F, I, H, N, D, C, or S, respectively.

Fig. 21A

[alpha-1-syntrophin PDZ domain]

```
 1 rrrvtvrkad agglgisikg grenkmpili skifkglaad qtealfvgda ilsvngedls
61 sathdeavqa lkktgkevvl evkymk (SEQ ID NO:1079)
```

Fig. 21B

[ER LBD]

```
  1 kknslalslt adqmvsalld aeppilysey dptrpfseas mmglltnlad relvhminwa
 61 krvpgfvdlt lhdqvhllec awleilmigl vwrsmehpgk llfapnllld rnqgkcvegm
121 veifdmllat ssrfrmmnlq geefvclksi illnsgvytf lsstlkslee kdhihrvldk
181 itdtlihlma kagltlqqqh qrlaqlllil shirhmsnkg mehlysmkck nvvplydlll
241 emldahrlha p (SEQ ID NO:1080)
```

MDKKYSIGL$Z^1$IGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAASX$^1$X$^2$RRRVTVRKADAGGLGISI
KGGRENKMPILISKIFKGLAADQTEALFVGDAILSVNGEDLSSATHDEAVQALKKTGKEVVLEVKYMKX$^3$X$^4$AS*DA*KA
ILSARLSKSRRLENLIAQLPGEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECFDSVEISGVEDRFNASLGTYH
DLLKIIKDKDFLDNEENEDILEDIVLTLTLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLHEHIANLAGSPAIKKGILQTVKVVDELVK
VMGRHKPENIVIEMARENQTTQKGQKNSRERMKRIEEGIKELGSQILKEHPVENTQLQNEKLYLYYLQNGRDMYVDQ
ELDINRLSDYDVD$Z^2$IVPQSFLKDDSIDNKVLTRSDKNRGKSDNVPSEEVVKKMKNYWRQLLNAKLITQRKFDNLTKA
ERGGLSELDKAGFIKRQLVETRQITKHVAQILDSRMNTKYDENDKLIREVKVITLKSKLVSDFRKDFQFYKVREINN
YHHAHDAYLNAVVGTALIKKYPKLESEFVYGDYKVYDVRKMIAKSEQEIGKATAKYFFYSNIMNFFKTEITLANGEI
RKRPLIETNGETGEIVWDKGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKDLIIKLPKYSLFELENGRK
RMLASAGELQKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLYETRIDLSQL
GGD (SEQ ID NO:1081)

where $Z^1$ is Asp and $Z^2$ is His (wtCas9), or $Z^1$ is Ala and $Z^2$ is Ala (dCas9);

and $X^1$, $X^2$, $X^3$, and $X^4$ are, independently, either present or absent, and if present, is Pro, Ser or Ala.

MDKKYSIGL$Z^1$IGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVD$Z^2$IVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSE*H*AS$X^1X^2$RRRVTVRKADAGGLGISIKGGRENKMPILISKIFKGLAADQTEALF
VGDAILSVNGEDLSSATHDEAVQALKKTGKEVVLEVKYMK$X^3X^4$AS*EQ*EIGKATAKYFFYSNIMNFFKTEITLANGEI
RKRPLIETNGETGEIVWDKGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKDLIIKLPKYSLFELENGRK
RMLASAGELQKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLYETRIDLSQL
GGD (SEQ ID NO:1082)

where $Z^1$ is Asp and $Z^2$ is His (wtCas9), or $Z^1$ is Ala and $Z^2$ is Ala (dCas9);

and $X^1$, $X^2$, $X^3$, and $X^4$ are, independently, either present or absent, and if present, is Pro, Ser or Ala.

Fig. 23

[arC9:231]

MDKKYSIGL$Z^1$IGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
ASX$^1$X$^2$KKNSLALSLTADQMVSALLDAEPPILYSEYDPTRPFSEASMMGLLTNLADRELVHMINWAKRVPGFVDLTLH
DQVHLLECAWLEILMIGLVWRSMEHPGKLLFAPNLLLDRNQGKCVEGMVEIFDMLLATSSRFRMMNLQGEEFVCLKS
IILLNSGVYTFLSSTLKSLEEKDHIHRVLDKITDTLIHLMAKAGLTLQQQHQRLAQLLLILSHIRHMSNKGMEHLYS
MKCKNVVPLYDLLLEMLDAHRLHAPX$^3$X$^4$AS*PG*EKKNGLFGNLIALSLGLTPNFKSNFDLAEDAKLQLSKDTYDDDLD
NLLAQIGDQYADLFLAAKNLSDAILLSDILRVNTEITKAPLSASMIKRYDEHHQDLTLLKALVRQQLPEKYKEIFFD
QSKNGYAGYIDGGASQEEFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQSFIERMTNFDKNLPNEKV
LPKHSLLYEYFTVYNELTKVKYVTEGMRKPAFLSGEQKKAIVDLLFKTNRKVTVKQLKEDYFKKIECFDSVEISGVE
DRFNASLGTYHDLLKIIKDKDFLDNEENEDILEDIVLTLTLFEDREMIEERLKTYAHLFDDKVMKQLKRRRYTGWGR
LSRKLINGIRDKQSGKTILDFLKSDGFANRNFMQLIHDDSLTFKEDIQKAQVSGQGDSLHEHIANLAGSPAIKKGIL
QTVKVVDELVKVMGRHKPENIVIEMARENQTTQKGQKNSRERMKRIEEGIKELGSQILKEHPVENTQLQNEKLYLYY
LQNGRDMYVDQELDINRLSDYDVD$Z^2$IVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVITLKSKLVSDFRKD
FQFYKVREINNYHHAHDAYLNAVVGTALIKKYPKLESEFVYGDYKVYDVRKMIAKSEQEIGKATAKYFFYSNIMNFF
KTEITLANGEIRKRPLIETNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVEQHKHYLDEIIEQISEFS
KRVILADANLDKVLSAYNKHRDKPIREQAENIIHLFTLTNLGAPAAFKYFDTTIDRKRYTSTKEVLDATLIHQSITG
LYETRIDLSQLGGD (SEQ ID NO:1083)

where $Z^1$ is Asp and $Z^2$ is His (wtCas9), or $Z^1$ is Ala and $Z^2$ is Ala (dCas9);

and $X^1$, $X^2$, $X^3$, and $X^4$ are, independently, either present or absent, and if present, is Pro, Ser or Ala.

VARIANT CAS9 POLYPEPTIDES COMPRISING INTERNAL INSERTIONS

CROSS-REFERENCE

This application claims the benefit of U.S. Provisional Patent Application No. 62/220,161, filed Sep. 17, 2015, which application is incorporated herein by reference in its entirety.

STATEMENT REGARDING FEDERALLY SPONSORED RESEARCH

This invention was made with government support under Grant No. EB018658 awarded by The National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-301PRV_Seq_List_ST25.txt" created on Sep. 17, 2015 and having a size of 7,737 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, the Cas9 protein functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 (or variants of Cas9 such as nickase variants) can generate site-specific DSBs or single-stranded breaks (SSBs) within target nucleic acids. Target nucleic acids can include double-stranded DNA (dsDNA) and single-stranded DNA (ssDNA) as well as RNA. When cleavage of a target nucleic acid occurs within a cell (e.g., a eukaryotic cell), the break in the target nucleic acid can be repaired by non-homologous end joining (NHEJ) or homology directed repair (HDR).

Thus, the Cas9 system provides a facile means of modifying genomic information. In addition, catalytically inactive Cas9 alone or fused to transcriptional activator or repressor domains can be used to alter transcription levels at sites within target nucleic acids by binding to the target site without cleavage.

SUMMARY

The present disclosure provides variant Cas9 polypeptides, where a variant Cas9 polypeptide of the present disclosure comprises an internal insertion of a heterologous polypeptide. The present disclosure provides nucleic acids comprising nucleotide sequences encoding the variant Cas9 polypeptides. The present disclosure provides host cells comprising a variant Cas9 polypeptide of the present disclosure, or comprising a nucleic acid encoding a variant Cas9 polypeptide of the present disclosure. The present disclosure provides methods of binding and/or modifying a target nucleic acid, involving use of a variant Cas9 polypeptide of the present disclosure.

BRIEF DESCRIPTION OF THE DRAWINGS

FIGS. 18A and 18B show amino acid sequences for wild-type and catalytically inactive *Streptococcus pyogenes* Cas9 protein.

FIG. 19A-19C show Table 1, showing Cas9 insertion sites for a heterologous polypeptide, according to embodiments of the present disclosure.

FIG. 20A-20C show Table 2, showing sequences flanking a heterologous polypeptide inserted in a Cas9 fusion polypeptide, according to embodiments of the present disclosure.

FIGS. 21A and 21B show amino acid sequences of heterologous polypeptides, according to embodiments of the present disclosure.

FIGS. 22A and 22B show amino acid sequences of Cas9 fusion polypeptides, according to embodiments of the present disclosure. As noted at the bottom of FIG. 20C, in some cases, the last amino acid of the Cas9 sequence flanking the heterologous peptide at the N-terminal end (at the junction of the N-terminal end of the heterologous polypeptide with the Cas9 polypeptide) is mutated. As an illustrative example, in the case depicted in FIG. 22B, there is a Q to H amino acid substitution at position 1027. In this case, the insert site is referred to as 1027 despite the presence of the mutation. Also as noted in FIG. 22B, these cases can be recognized when the amino acid of the Cas9 polypeptide that is N-terminal to the insertion site was mutated from an L, M, Q, K, E, W, or R to an F, I, H, N, D, C, or S, respectively.

FIG. 23 shows an amino acid sequence of a Cas9 fusion polypeptide, according to embodiments of the present disclosure.

DEFINITIONS

Figure 1A:
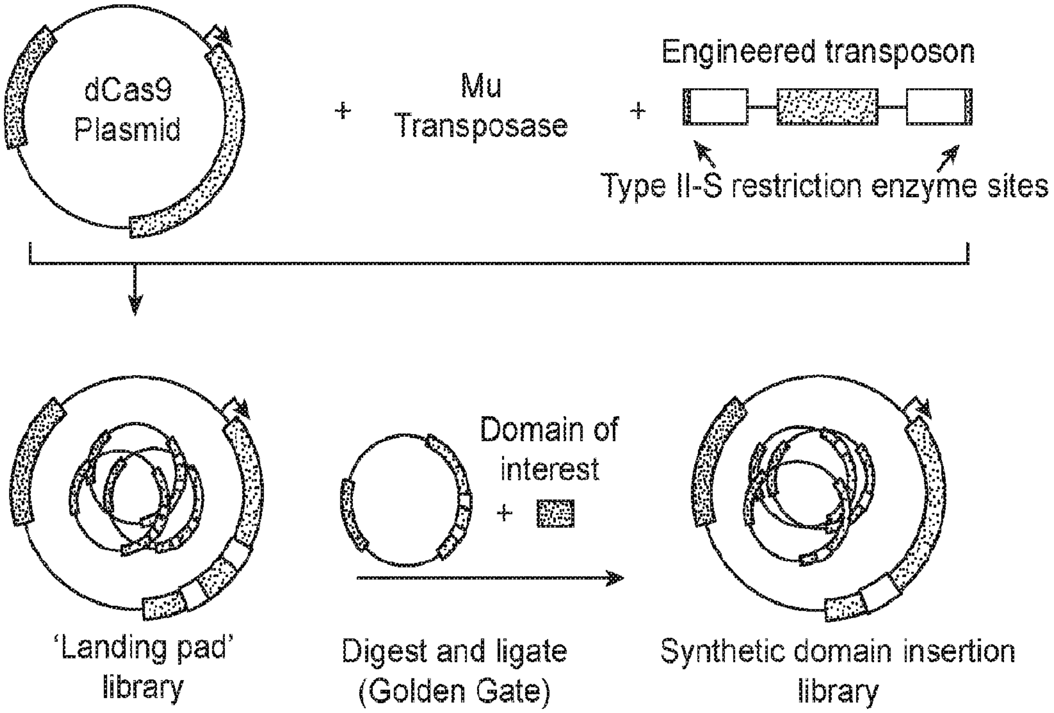
FIG. 1A-1E are a collection of diagrams, images and figures showing mapping domain insertion potential into Cas9, according to embodiments of the present disclosure.

By "Cas9 polypeptide" or "Cas9 protein" or "site-directed modifying polypeptide" or "RNA-binding site-directed polypeptide" or "RNA-binding site-directed modifying polypeptide" or "site-directed polypeptide" it is meant a polypeptide that binds RNA and is targeted to a specific DNA sequence. A Cas9 protein as described herein is targeted to a specific DNA sequence by the RNA (a guide RNA) to which it is bound. The guide RNA comprises a sequence that is complementary to a target sequence within the target DNA, thus targeting the bound Cas9 protein to a specific location within the target DNA (the target sequence).

"Heterologous," as used herein, means a nucleotide or polypeptide sequence that is not found in the native nucleic acid or protein, respectively. For example, a variant Cas9 polypeptide of the present disclosure comprises: a) a Cas9 polypeptide; and b) a heterologous polypeptide comprising an amino acid sequence from a protein other than Cas9 polypeptide.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant Cas9 polypeptide" includes a plurality of such polypeptides and reference to "the heterologous polypeptide" includes reference to one or more heterologous polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant Cas9 polypeptides ("Cas9 fusion polypeptides"), where a variant Cas9 polypeptide of the present disclosure comprises an internal insertion of a heterologous polypeptide. The present disclosure provides nucleic acids comprising nucleotide sequences encoding the variant Cas9 polypeptides. The present disclosure provides host cells comprising a variant Cas9 polypeptide of the present disclosure, or comprising a nucleic acid encoding a variant Cas9 polypeptide of the present disclosure. The present disclosure provides methods of binding and/or modifying a target nucleic acid, involving use of a variant Cas9 polypeptide of the present disclosure.

Variant Cas9 Polypeptides

The present disclosure provides variant Cas9 polypeptides comprising one or more heterologous polypeptides inserted internally within the Cas9 polypeptide at one or more internal insertion sites. A variant Cas9 polypeptide of the present disclosure is also referred to as a "Cas9 fusion polypeptide."

A Cas9 fusion polypeptide of the present disclosure comprises: a) a Cas9 polypeptide; and (b) a heterologous amino acid or heterologous polypeptide inserted internally within the Cas9 polypeptide. In some cases, the heterologous amino acid or heterologous polypeptide is inserted at a position that is immediately adjacent and C-terminal to an amino acid residue corresponding to a residue selected from 3, 4, 42, 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, 713, 715, 717, 719, 721, 724, 798, 801, 802, 804, 834, 868, 890, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, 1073, 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, based on the numbering of the Cas9 protein set forth in SEQ ID NO: 5. The Cas9 fusion polypeptide retains binding target nucleic acid binding activity relative to the binding activity of the Cas9 polypeptide without the inserted heterologous amino acid or heterologous polypeptide.

In some cases, the heterologous amino acid or heterologous polypeptide is inserted at a position that is immediately adjacent and N-terminal to an amino acid residue corresponding to a residue selected from 3, 4, 42, 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, 713, 715, 717, 719, 721, 724, 798, 801, 802, 804, 834, 868, 890, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, 1073, 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, based on the numbering of the Cas9 protein set forth in SEQ ID NO: 5. The Cas9 fusion polypeptide retains binding target nucleic acid binding activity relative to the binding activity of the Cas9 polypeptide without the inserted heterologous amino acid or heterologous polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to an amino acid residue corresponding to a residue selected from 3, 4, 42, 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, 713, 715, 717, 719, 721, 724, 798, 801, 802, 804, 834, 868, 890, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, 1073, 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, of the Cas9 protein set forth in SEQ ID NO: 5, and wherein the Cas9 fusion polypeptide retains cleavage and/or binding activity relative to the activity of the Cas9 polypeptide without the inserted heterologous amino acid or heterologous polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to an amino acid residue corresponding to a residue selected from 3, 4, 42, 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, 713, 715, 717, 719, 721, 724, 798, 801, 802, 804, 834, 868, 890, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, 1073, 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, of the Cas9 protein set forth in SEQ ID NO: 5, and wherein the Cas9 fusion polypeptide retains cleavage and/or binding activity relative to the activity of the Cas9 polypeptide without the inserted heterologous amino acid or heterologous polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 3 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 3 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 2 and 3, or between residues 3 and 4, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 4 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 4 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 3 and 4, or between residues 4 and 5, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 42 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 42 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 41 and 42, or between residues 42 and 43, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 112 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 112 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 111 and 112, or between residues 112 and 113, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 127 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 127 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 126 and 127, or between residues 127 and 128, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 193 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 193 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 192 and 193, or between residues 193 and 194, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 197 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 197 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 196 and 197, or between residues 197 and 198, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 202 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 202 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 201 and 202, or between residues 202 and 203, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 204 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 204 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 203 and 204, or between residues 204 and 205, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 205 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 205 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 204 and 205, or between residues 205 and 206, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 206 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 206 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 205 and 206, or between residues 206 and 207, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 207 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 207 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 206 and 207, or between residues 207 and 208, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 208 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 208 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 207 and 208, or between residues 208 and 209, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 209 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 209 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 208 and 209, or between residues 209 and 210, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 211 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 211 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 210 and 211, or between residues 211 and 212, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 214 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 214 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 213 and 214, or between residues 214 and 215, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 217 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 217 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 216 and 217, or between residues 217 and 218, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 228 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 228 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 227 and 228, or between residues 228 and 229, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 231 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 231 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 230 and 231, or between residues 231 and 232, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 238 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 238 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 237 and 238, or between residues 238 and 239, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 257 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 257 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 257 and 257, or between residues 257 and 258, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 259 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 259 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 258 and 259, or between residues 259 and 260, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 313 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 313 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 312 and 313, or between residues 313 and 314, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 390 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 390 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 389 and 390, or between residues 390 and 391, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 456 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 456 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 455 and 456, or between residues 456 and 457, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 460 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 460 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 459 and 460, or between residues 460 and 461, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 467 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 467 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 466 and 467, or between residues 467 and 468, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 468 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 468 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 467 and 468, or between residues 468 and 469, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 470 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 470 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 469 and 470, or between residues 470 and 471, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 474 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 474 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 473 and 474, or between residues 474 and 475, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 532 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 532 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 531 and 532, or between residues 532 and 533, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 533 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 533 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 532 and 533, or between residues 533 and 534, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 536 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 536 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 535 and 536, or between residues 536 and 537, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 576 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 576 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 575 and 576, or between residues 576 and 577, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 577 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 577 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 577 and 578, or between residues 578 and 579, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 579 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 579 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 579 and 580, or between residues 580 and 581, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 588 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 588 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 587 and 588, or between residues 588 and 589, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 639 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 639 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 638 and 639, or between residues 639 and 670, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 641 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 641 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 640 and 641, or between residues 641 and 642, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 645 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 645 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 644 and 645, or between residues 645 and 646, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 647 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 647 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 646 and 647, or between residues 647 and 648, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 687 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 687 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 686 and 687, or between residues 687 and 688, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 689 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 689 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 688 and 689, or between residues 689 and 690, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 690 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 690 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 689 and 690, or between residues 690 and 691, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 692 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 692 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 691 and 692, or between residues 692 and 693, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 713 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 713 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 712 and 713, or between residues 713 and 714, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 715 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 715 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 714 and 715, or between residues 715 and 716, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 717 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 717 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 716 and 717, or between residues 717 and 718, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 719 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 719 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 718 and 719, or between residues 719 and 720, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 721 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 721 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 720 and 721, or between residues 721 and 722, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 724 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 724 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 723 and 724, or between residues 724 and 725, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 798 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 798 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 797 and 798, or between residues 798 and 799, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 801 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 801 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 800 and 801, or between residues 801 and 802, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 802 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 802 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 801 and 802, or between residues 802 and 803, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 804 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 804 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 803 and 804, or between residues 804 and 805, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 834 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 834 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 833 and 834, or between residues 834 and 835, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 868 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 868 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 867 and 868, or between residues 868 and 869, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 890 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 890 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 889 and 890, or between residues 890 and 891, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 940 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 940 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 939 and 940, or between residues 940 and 941, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 941 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 941 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 940 and 941, or between residues 941 and 942, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 944 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 944 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 943 and 944, or between residues 944 and 945, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 947 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 947 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 946 and 947, or between residues 947 and 948, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 952 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 952 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 951 and 952, or between residues 952 and 953, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1010 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1010 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1009 and 1010, or between residues 1010 and 1011, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1011 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1011 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1011 and 1012, or between residues 1010 and 1011, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1012 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1012 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1011 and 1012, or between residues 1012 and 1013, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1015 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1015 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1014 and 1015, or between residues 1015 and 1016, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1016 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1016 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1015 and 1016, or between residues 1016 and 1017, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1022 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1022 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1021 and 1022, or between residues 1022 and 1023, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1026 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1026 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1025 and 1026, or between residues 1026 and 1027, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1027 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1027 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1026 and 1027, or between residues 1027 and 1028, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1031 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1031 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1030 and 1031, or between residues 1031 and 1032, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1034 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1034 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1033 and 1034, or between residues 1034 and 1035, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1046 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1046 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1045 and 1046, or between residues 1046 and 1047, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1047 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1047 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1046 and 1047, or between residues 1047 and 1048, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1049 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1049 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1048 and 1049, or between residues 1049 and 1050, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1050 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1050 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1049 and 1050, or between residues 1050 and 1051, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1051 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1051 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1050 and 1051, or between residues 1051 and 1052, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1052 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1052 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1051 and 1052, or between residues 1052 and 1053, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1053 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and H-terminal to amino acid 1053 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1052 and 1053, or between residues 1053 and 1054, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1054 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1054 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1053 and 1054, or between residues 1054 and 1055, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1056 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1056 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1055 and 1056, or between residues 1056 and 1057, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1058 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1058 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1057 and 1058, or between residues 1058 and 1059, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1061 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1061 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1060 and 1061, or between residues 1061 and 1062, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1062 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1062 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1061 and 1062, or between residues 1062 and 1063, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1063 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1063 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1062-1063, or between residues 1063-1064, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1064 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1064 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1063-1064, or between residues 1064-1065, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1065 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1065 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1064-1065, or between residues 1065-1066, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1068 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1068 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1067-1068, or between residues 1068-1069, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1070 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1070 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1069-1070, or between residues 1070-1071, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1071 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1071 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1070-1071, or between residues 1071-1072, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1073 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1073 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1072-1073, or between residues 1073-1074, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1145 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1145 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1144-1145, or between residues 1145-1146, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1148 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1148 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1147-1148, or between residues 1148-1149, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1149 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1149 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1148-1149, or between residues 1149-1150, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1152 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1152 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1151-1152, or between residues 1152-1153, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1153 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1153 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1152-1153, or between residues 1153-1154, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1155 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1155 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1154-1155, or between residues 1155-1156, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1156 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1156 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1155-1156, or between residues 1156-1157, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1160 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1160 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1159-1160, or between residues 1160-1161, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1161 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1161 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1160-1161, or between residues 1161-1162, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1175 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1175 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1174-1175, or between residues 1175-1176, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1179 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1179 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1178-1179, or between residues 1179-1180, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1183 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1183 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1182-1183, or between residues 1183-1184, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1186 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1186 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1185-1186, or between residues 1186-1187, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1188 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1188 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1187-1188, or between residues 1188-1189, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1189 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1189 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1188-1189, or between residues 1189-1190, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1190 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1190 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1189-1190, or between residues 1190-1191, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1191 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1191 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1190-1191, or between residues 1191-1192, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1193 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1193 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1192-1193, or between residues 1193-1194, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1194 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1194 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1193-1194, or between residues 1194-1195, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1195 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1195 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1194-1195, or between residues 1195-1196, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1196 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1196 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1195-1196, or between residues 1196-1197, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1197 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1197 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1196-1197, or between residues 1197-1198, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1204 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1204 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1203-1204, or between residues 1204-1205, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1205 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1205 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1204-1205, or between residues 1205-1206, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1206 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1206 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1205-1206, or between residues 1206-1207, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1207 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1207 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1206-1207, or between residues 1207-1208, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1212 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1212 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1211-1212, or between residues 1212-1213, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1213 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1213 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1212-1213, or between residues 1213-1214, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1228 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1228 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1227-1228, or between residues 1228-1229, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1229 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1229 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1228-1229, or between residues 1229-1230, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1230 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1230 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1229-1230, or between residues 1230-1231, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1233 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1233 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1232-1233, or between residues 1233-1234, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1234 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1234 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1234-1235, or between residues 1235-1236, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1237 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1237 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1236-1237, or between residues 1237-1238, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1238 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1238 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1237-1238, or between residues 1238-1239, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1239 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1239 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1238-1239, or between residues 1239-1240, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1240 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1240 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1239-1240, or between residues 1240-1241, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1242 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1242 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1241-1242, or between residues 1242-1243, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1243 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1243 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1242-1243, or between residues 1243-1244, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1244 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1244 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1243-1244, or between residues 1244-1245, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1246 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1246 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1245-1246, or between residues 1246-1247, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1247 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1247 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1246-1247, or between residues 1247-1248, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1248 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1248 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1247-1248, or between residues 1248-1249, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1250 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1250 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1249-1250, or between residues 1250-1251, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1251 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1251 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1250-1251, or between residues 1251-1252, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1252 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1252 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1251-1252, or between residues 1252-1253, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1253 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1253 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1252-1253, or between residues 1253-1254, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1255 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1255 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1254-1255, or between residues 1255-1256, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1259 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1259 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1258-1259, or between residues 1259-1260, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1260 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1260 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1259-1260, or between residues 1260-1261, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1262 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1262 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1261-1262, or between residues 1262-1263, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1267 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1267 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1266-1267, or between residues 1267-1268, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1268 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1268 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1267-1268, or between residues 1268-1269, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1269 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1269 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1268-1269, or between residues 1269-1270, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1270 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1270 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1269-1270, or between residues 1270-1271, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1281 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1281 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1280-1281, or between residues 1281-1282, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1282 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1282 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1281-1282, or between residues 1282-1283, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1283 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1283 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1282-1283, or between residues 1283-1284, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1284 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1284 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1283-1284, or between residues 1284-1285, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1287 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1287 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1286-1287, or between residues 1287-1288, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1289 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1289 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1288-1289, or between residues 1289-1290, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1291 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1291 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1290-1291, or between residues 1291-1292, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1292 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1292 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1291-1292, or between residues 1292-1293, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1293 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1293 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1292-1293, or between residues 1293-1294, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1294 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1294 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1293-1294, or between residues 1294-1295, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1295 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1295 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1294-1295, or between residues 1295-1296, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1296 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1296 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1295-1296, or between residues 1296-1297, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1298 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1298 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1297-1298, or between residues 1298-1299, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1299 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1299 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1298-1299, or between residues 1299-1300, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1300 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1300 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1299-1300, or between residues 1300-1301, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1302 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1302 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1301-1302, or between residues 1302-1303, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1304 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1304 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1303-1304, or between residues 1304-1305, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1306 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1306 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1305-1306, or between residues 1306-1307, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1307 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1307 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1306-1307, or between residues 1307-1308, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1344 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1344 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1343-1344, or between residues 1344-1345, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1346 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1346 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1345-1346, or between residues 1346-1347, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1347 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1347 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1346-1347, or between residues 1347-1348, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1348 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1348 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1347-1348, or between residues 1348-1349, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1360 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1360 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1359-1360, or between residues 1360-1361, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1363 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1363 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1363-1363, or between residues 1363-1364, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1366 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and N-terminal to amino acid 1366 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1365-1366, or between residues 1366-1367, of the Cas9 protein set forth in SEQ ID NO:5, or a corresponding amino acid residue in another Cas9 polypeptide.

In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1367 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, a Cas9 fusion polypeptide of the present disclosure comprises: (a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal to amino acid 1367 of the Cas9 protein set forth in SEQ ID NO:5, or a corresponding amino acid residue in another Cas9 polypeptide; and wherein the Cas9 fusion polypeptide retains cleavage and/or binding activity relative to the activity of the Cas9 polypeptide without the inserted heterologous amino acid or heterologous polypeptide. In some cases, the heterologous amino acid or heterologous polypeptide is inserted between residues 1366-1367, or between residues 1367-1368, of the Cas9 protein set forth in SEQ ID NO:5, or a corresponding amino acid residue in another Cas9 polypeptide.

As noted at the bottom of FIG. 20C, in some cases, the last amino acid of the Cas9 sequence flanking the heterologous peptide at the N-terminal end is mutated upon insertion of the heterologous polypeptide. As an illustrative example, in the case depicted in FIG. 22B, there is a Q to H amino acid substitution at position 1027. In this case, the insert site is referred to as 1027 despite the presence of the mutation. Refer to FIG. 22B for an illustrative example.

Cas9 Polypeptide

TABLE 3

Table 3 lists 4 motifs that are present in Cas9 sequences from various species. The amino acids listed here are from the Cas9 from *S. pyogenes* set forth in SEQ ID NO: 5.

| Motif # | Motif | Amino acids (residue #s) | Highly conserved |
|---|---|---|---|
| 1 | RuvC-like I | AGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like II | HHAHDAYL (982-989) (SEQ ID NO: 4) | H982, H983, A984, D986, A987 |

A variant Cas9 protein can have the same parameters for sequence identity as for a wild type Cas9 protein (except the variant has at least one sequence difference relative to a wild type Cas9 protein). Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NOs: 1-4, respectively, as depicted in Table 3, or to the corresponding portions in any of the amino acid sequences set forth in SEQ ID NOs: 5-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 3 and are set forth as SEQ ID NOs: 1-4, respectively), or to the corresponding portions in any of the amino acid sequences set forth in SEQ ID NOs: 6-816.

In some cases, a suitable variant Cas9 protein (e.g., the Cas9 polypeptide portion of a subject Cas9 fusion polypeptide) comprises an amino acid sequence having 60% or more, 70% or more, 75% or more, 80% or more, 85% or more, 90% or more, 95% or more, or 99% or more sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816.

In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816.

Any Cas9 protein as defined above can be used as a Cas9 polypeptide portion of a subject Cas9 fusion polypeptide, and any Cas9 polypeptide portion described above can include one or more amino acid mutations that render the Cas9 polypeptide portion of a subject Cas9 fusion polypeptide to be a nickase or a catalytically inactive Cas9 protein.

In some embodiments, a subject Cas9 fusion polypeptide includes a Cas9 polypeptide portion that has reduced catalytic activity (e.g., a Cas9 protein with nickase activity or a Cas9 protein that is catalytically inactive, e.g., dCas9). For example, when a Cas9 protein has a mutation at an amino acid position corresponding to D10, G12, G17, E762, H840, N854, N863, H982, H983, A984, D986, and/or a A987 of the Cas9 protein set forth in SEQ ID NO: 5 (e.g., D10A, G12A, G17A, E762A, H840A, N854A, N863A, H982A, H983A, A984A, and/or D986A), the variant Cas9 protein can still bind to target DNA in a site-specific manner (because it is still guided to a target DNA sequence by a guide RNA) as long as it retains the ability to interact with the guide RNA.

In some cases, the variant Cas9 protein is a nickase (e.g., cleaves one strand of a double stranded target nucleic acid but not the other strand) (e.g., the Cas9 polypeptide portion of a subject Cas9 fusion polypeptide can be a nickase, e.g., can include one or more amino acid mutations that make it a nickase). For example, in some cases the variant Cas9 protein has a mutation in a catalytic domain (e.g., a mutation in a RuvC or HNH domain). For example, in some cases, a variant Cas9 protein can cleave the complementary strand of a target nucleic acid but has reduced ability to cleave the non-complementary strand of a target nucleic acid. For example, the variant Cas9 protein can have a mutation (amino acid substitution) that reduces the function of the RuvC domain. As a non-limiting example, in some embodiments, a variant Cas9 protein has a mutation at residue D10 (e.g., D10A, aspartate to alanine) of SEQ ID NO: 5 (or the corresponding position of any of the proteins set forth in SEQ ID NOs: 6-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). Examples of such amino acid positions in a RuvC domain can include (as depicted in Table 3): D10, G12, G17, E762, H982, H983, A984, D986, and/or A987 of the Cas9 protein set forth in SEQ ID NO: 5 (e.g., D10A, G12A, G17A, E762A, H982A, H983A, A984A, and/or D986A).

In some cases, a variant Cas9 protein is a nickase (e.g., cleaves one strand of a double stranded target nucleic acid but not the other strand (e.g., the Cas9 polypeptide portion of a subject Cas9 fusion polypeptide can be a nickase, e.g., can include one or more amino acid mutations that make it a nickase). For example, in some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand (e.g., does not cleave a single stranded target nucleic acid). As a non-limiting example, in some embodiments, the variant Cas9 protein has a mutation at position H840 (e.g., an H840A mutation, histidine to alanine) of SEQ ID NO: 5 (or the corresponding position of any of the proteins set forth as SEQ ID NOs: 6-816, e.g., H839 (e.g., H839A) of SEQ ID NO: 6) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid). Examples of such amino acid positions in an HNH domain can include (as depicted in Table 3): H840, N854, and/or N863 of the Cas9 protein set forth in SEQ ID NO: 5 (e.g., H840A, N854A, and/or N863A).

In some cases, a variant Cas9 protein has a reduced ability to cleave both the complementary and the non-complementary strands of a double stranded target nucleic acid. As a non-limiting example, in some cases, the variant Cas9 protein harbors mutations at residues D10 and H840 (e.g., D10A and H840A) of SEQ ID NO: 5 (or the corresponding residues of any of the proteins set forth as SEQ ID NOs: 6-816, e.g., D10 and H839 of SEQ ID NO: 6) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. For example, a variant Cas9 protein can have a mutation in one or more of amino acid positions in (i) a RuvC domain (as depicted in Table 3): D10, G12, G17, E762, H982, H983, A984, D986, and/or A987 of the Cas9 protein set forth in SEQ ID NO: 5 (e.g., D10A, G12A, G17A, E762A, H982A, H983A, A984A, and/or D986A); and one or more of amino acid positions in (ii) an HNH domain (as depicted in Table 3): H840, N854, and/or N863 of the Cas9 protein set forth in SEQ ID NO: 5 (e.g., H840A, N854A, and/or N863A).

Insertion Sites

A heterologous polypeptide (or heterologous amino acid such as a cysteine residue or a non-natural amino acid) can be inserted at several positions within a Cas9 polypeptide to generate a subject Cas9 fusion polypeptide. For example, by insertional screening (i.e., insertion of a heterologous polypeptide at positions throughout a Cas9 protein), the inventors discovered several sites that tolerate insertions without substantially affecting the function of the Cas9 protein (e.g., without substantially affecting the cleaving of a target nucleic acid and/or the binding of a target nucleic acid).

In some cases, the Cas9 fusion polypeptide retains (has) activity (e.g., cleavage and/or binding activity) relative to the activity of the Cas9 polypeptide without the inserted heterologous amino acid or heterologous polypeptide, where the Cas9 polypeptide without the inserted heterologous amino acid or heterologous polypeptide is also referred to as the "parent Cas9 polypeptide." For example, in some cases, the Cas9 fusion polypeptide has (retains) 50% or more of the activity (e.g., cleavage and/or binding activity) of the corresponding parent Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the activity (e.g., cleavage and/or binding activity) of the corresponding parent Cas9 polypeptide (the Cas9 polypeptide that does not have the insertion).

In some cases, the Cas9 fusion polypeptide retains (has) binding activity relative to the activity of the Cas9 polypeptide without the inserted heterologous amino acid or heterologous polypeptide. For example, in some cases, the Cas9 fusion polypeptide has (retains) 50% or more of the binding activity of the corresponding Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the binding activity of the corresponding Cas9 polypeptide (the Cas9 polypeptide that does not have the insertion).

In some cases, the Cas9 fusion polypeptide retains (has) cleavage activity relative to the activity of the Cas9 polypeptide without the inserted heterologous amino acid or heterologous polypeptide. For example, in some cases, the Cas9 fusion polypeptide has (retains) 50% or more of the cleavage activity of the corresponding Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the cleavage activity of the corresponding Cas9 polypeptide (the Cas9 polypeptide that does not have the insertion).

In some cases, the Cas9 fusion polypeptide retains (has) binding and cleavage activity relative to the activity of the Cas9 polypeptide without the inserted heterologous amino acid or heterologous polypeptide. For example, in some cases, the Cas9 fusion polypeptide has (retains) 50% or more of the binding and cleavage activity of the corresponding Cas9 polypeptide (the Cas9 polypeptide that does not have the insertion). For example, in some cases, the Cas9 fusion polypeptide has (retains) 60% or more (70% or more, 80% or more, 90% or more, 92% or more, 95% or more, 98% or more, or 100%) of the binding and cleavage activity of the corresponding Cas9 polypeptide (the Cas9 polypeptide that does not have the insertion). Methods of measuring cleaving and/or binding activity of a Cas9 polypeptide and/or a Cas9 fusion polypeptide will be known to one of ordinary skill in the art and any convenient method can be used.

Table 4 lists suitable Cas9 polypeptide insertion sites into which a heterologous amino acid or heterologous polypeptide can be inserted to generate a fusion Cas9 polypeptide of the present disclosure.

TABLE 4

Identified insertion sites within the Cas9 protein. A heterologous amino acid or heterologous polypeptide can be inserted immediately adjacent and C-terminal to the position listed (see examples section below), or immediately adjacent and N-terminal to the position listed. Numbering is according to the Cas9 protein set forth in SEQ ID NO: 5. Corresponding insertion sites in other Cas9 polypeptides are readily identified by aligning the amino acid sequence of any given Cas9 polypeptide with the amino acid sequence of the Cas9 protein set forth in SEQ ID NO: 5.

| Domain/Region of insertion | Insertion Sites |
|---|---|
| RuvC domain (RuvCI Region) | 3, 4, 42 |
| RuvC domain (RuvCII Region) | 719, 721,724 |
| RuvC domain (RuvCIII Region) | 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, 1073 |
| alpha helical RNA recognition lobe | 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, 713 |
| linker between the alpha helical and nuclease lobes | 715, 717 |
| PAM interacting domain | 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, 1367 |

In some cases, a heterologous amino acid or heterologous polypeptide is inserted in a RuvC domain (e.g., immediately adjacent and C-terminal to an amino acid residue corresponding to a residue selected from 3, 4, 42, 719, 721, 724, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, and 1073 of the Cas9 protein set forth in SEQ ID NO: 5). In some cases, a heterologous amino acid or heterologous polypeptide is inserted in a RuvC domain (e.g., immediately adjacent and N-terminal to an amino acid residue corresponding to a residue selected from 3, 4, 42, 719, 721, 724, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, and 1073 of the Cas9 protein set forth in SEQ ID NO: 5).

In some cases, a heterologous amino acid or heterologous polypeptide is inserted in a RuvCI region (e.g., immediately adjacent and C-terminal to an amino acid residue corresponding to a residue selected from 3, 4, and 42 of the Cas9 protein set forth in SEQ ID NO: 5). In some cases, a heterologous amino acid or heterologous polypeptide is inserted in a RuvCI region (e.g., immediately adjacent and N-terminal to an amino acid residue corresponding to a residue selected from 3, 4, and 42 of the Cas9 protein set forth in SEQ ID NO: 5).

In some cases, a heterologous amino acid or heterologous polypeptide is inserted in a RuvCII region (e.g., immediately adjacent and C-terminal to an amino acid residue corresponding to a residue selected from 719, 721, and 724 of the Cas9 protein set forth in SEQ ID NO: 5). In some cases, a heterologous amino acid or heterologous polypeptide is inserted in a RuvCII region (e.g., immediately adjacent and N-terminal to an amino acid residue corresponding to a residue selected from 719, 721, and 724 of the Cas9 protein set forth in SEQ ID NO: 5).

In some cases, a heterologous amino acid or heterologous polypeptide is inserted in a Ruv CIII region (e.g., immediately adjacent and C-terminal to an amino acid residue corresponding to a residue selected from 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, and 1073 of the Cas9 protein set forth in SEQ ID NO: 5). In some cases, a heterologous amino acid or heterologous polypeptide is inserted in a Ruv CIII region (e.g., immediately adjacent and N-terminal to an amino acid residue corresponding to a residue selected from 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, and 1073 of the Cas9 protein set forth in SEQ ID NO: 5).

In some cases, a heterologous amino acid or heterologous polypeptide is inserted in an alpha helical RNA recognition lobe (sometimes referred to as REC in the art) at a position that is immediately adjacent and C-terminal to an amino acid residue corresponding to a residue selected from 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, and 713, of the Cas9 protein set forth in SEQ ID NO: 5. In some cases, a heterologous amino acid or heterologous polypeptide is inserted in an alpha helical RNA recognition lobe (sometimes referred to as REC in the art) at a position that is immediately adjacent and N-terminal to an amino acid residue corresponding to a residue selected from 112, 127, 193, 197, 202, 204, 205, 206, 207, 208, 209, 211, 214, 217, 228, 231, 238, 257, 259, 313, 390, 456, 460, 467, 468, 470, 474, 532, 533, 536, 576, 577, 579, 588, 639, 641, 645, 647, 687, 689, 690, 692, and 713, of the Cas9 protein set forth in SEQ ID NO: 5.

In some cases, a heterologous amino acid or heterologous polypeptide is inserted in a linker that is between the alpha helical and nuclease lobes at a position that is immediately adjacent and C-terminal to an amino acid residue corresponding to a residue selected from 715 and 717, of the Cas9 protein set forth in SEQ ID NO: 5. In some cases, a heterologous amino acid or heterologous polypeptide is inserted in a linker that is between the alpha helical and nuclease lobes at a position that is immediately adjacent and N-terminal to an amino acid residue corresponding to a residue selected from 715 and 717, of the Cas9 protein set forth in SEQ ID NO: 5.

In some cases, a heterologous amino acid or heterologous polypeptide is inserted in an HNH domain at a position that is immediately adjacent and C-terminal to an amino acid residue corresponding to a residue selected from 798, 801, 802, 804, 834, 868, and 890, of the Cas9 protein set forth in SEQ ID NO: 5. In some cases, a heterologous amino acid or heterologous polypeptide is inserted in an HNH domain at a position that is immediately adjacent and N-terminal to an amino acid residue corresponding to a residue selected from 798, 801, 802, 804, 834, 868, and 890, of the Cas9 protein set forth in SEQ ID NO: 5.

In some cases, a heterologous amino acid or heterologous polypeptide is inserted in a PAM interacting domain at a position that is immediately adjacent and C-terminal to an amino acid residue corresponding to a residue selected from 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, of the Cas9 protein set forth in SEQ ID NO: 5. In some cases, a heterologous amino acid or heterologous polypeptide is inserted in a PAM interacting domain at a position that is immediately adjacent and N-terminal to an amino acid residue corresponding to a residue selected from 1145, 1148, 1149, 1152, 1153, 1155, 1156, 1160, 1161, 1175, 1179, 1183, 1186, 1188, 1189, 1190, 1191, 1193, 1194, 1195, 1196, 1197, 1204, 1205, 1206, 1207, 1212, 1213, 1228, 1229, 1230, 1233, 1234, 1237, 1238, 1239, 1240, 1242, 1243, 1244, 1246, 1247, 1248, 1250, 1251, 1252, 1253, 1255, 1259, 1260, 1262, 1267, 1268, 1269, 1270, 1281, 1282, 1283, 1284, 1287, 1289, 1291, 1292, 1293, 1294, 1295, 1296, 1298, 1299, 1300, 1302, 1304, 1306, 1307, 1344, 1346, 1347, 1348, 1360, 1363, 1366, and 1367, of the Cas9 protein set forth in SEQ ID NO: 5.

In some cases, a heterologous amino acid or heterologous polypeptide is inserted inside within a region of secondary structure (e.g., at a position that is immediately adjacent and C-terminal to an amino acid residue corresponding to a residue selected from: 42, 127, 193, 195, 208, 209, 211, 214, 238, 390, 639, 641, 645, 647, 721, 722, 724, 802, 804, 1034, 1063, 1064, 1065, 1148, 1149, 1150, 1175, 1179, 1183, 1197, 1204, 1212, 1213, 1255, 1259, 1260, 1262, 1267, 1268, 1269, 1270, 1286, 1287, 1289, 1291, 1292, 1293, 1294, 1295, 1296, 1306, 1307, 1347, and 1348, of the Cas9 protein set forth in SEQ ID NO: 5). For example, in some cases, a heterologous amino acid or heterologous polypeptide is inserted within a region of secondary structure (e.g., at a position that is immediately adjacent and C-terminal to an amino acid residue corresponding to a residue selected from: 1291, 1260, 1196, 1267, 1064, 1161, and 1148, of the Cas9 protein set forth in SEQ ID NO: 5). In some cases, a heterologous amino acid or heterologous polypeptide is inserted inside within a region of secondary structure (e.g., at a position that is immediately adjacent and N-terminal to an amino acid residue corresponding to a residue selected from: 42, 127, 193, 195, 208, 209, 211, 214, 238, 390, 639, 641, 645, 647, 721, 722, 724, 802, 804, 1034, 1063, 1064, 1065, 1148, 1149, 1150, 1175, 1179, 1183, 1197, 1204, 1212, 1213, 1255, 1259, 1260, 1262, 1267, 1268, 1269, 1270, 1286, 1287, 1289, 1291, 1292, 1293, 1294, 1295, 1296, 1306, 1307, 1347, and 1348, of the Cas9 protein set forth in SEQ ID NO: 5). For example, in some cases, a heterologous amino acid or heterologous polypeptide is inserted within a region of secondary structure (e.g., at a position that is immediately adjacent and N-terminal to an amino acid residue corresponding to a residue selected from: 1291, 1260, 1196, 1267, 1064, 1161, and 1148, of the Cas9 protein set forth in SEQ ID NO: 5).

In some cases, a heterologous amino acid or heterologous polypeptide is inserted immediately adjacent and C-terminal to an amino acid residue corresponding to residue 231 of the Cas9 protein set forth in SEQ ID NO: 5. For example, in some such cases, an inserted heterologous polypeptide confers an inducible conformational change on the Cas9 fusion polypeptide (e.g., the heterologous polypeptide can be an estrogen receptor alpha ligand binding domain (ER-LBD)). In some cases, an inserted heterologous polypeptide (inserted immediately adjacent and C-terminal to an amino acid residue corresponding to residue 231 of the Cas9 protein set forth in SEQ ID NO: 5) confers an inducible conformational change on the Cas9 fusion polypeptide and the heterologous polypeptide is a light-inducible LOV2 domain. In some cases, a heterologous amino acid or heterologous polypeptide is inserted immediately adjacent and N-terminal to an amino acid residue corresponding to residue 231 of the Cas9 protein set forth in SEQ ID NO: 5. For example, in some such cases, an inserted heterologous polypeptide confers an inducible conformational change on the Cas9 fusion polypeptide (e.g., the heterologous polypeptide can be an estrogen receptor alpha ligand binding domain (ER-LBD)). In some cases, an inserted heterologous polypeptide (inserted immediately adjacent and C-terminal to an amino acid residue corresponding to residue 231 of the Cas9 protein set forth in SEQ ID NO: 5) confers an inducible conformational change on the Cas9 fusion polypeptide and the heterologous polypeptide is a light-inducible LOV2 domain.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 3 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 3 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 4 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 4 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 42 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 42 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 112 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 112 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 127 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 127 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 193 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 193 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 197 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 197 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 202 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 202 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 204 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 204 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 205 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 206 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 206 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 207 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 208 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 208 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 209 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 209 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 211 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 214 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 214 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 217 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 217 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 228 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 231 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 231 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 238 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 238 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 257 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 259 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 259 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 313 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 313 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 390 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 390 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 456 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 456 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 460 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 460 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 467 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 467 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 468 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 468 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 470 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 470 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 474 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 474 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 532 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 532 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 533 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 533 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 536 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 536 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 576 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 576 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 577 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 577 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 579 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 579 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 588 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 588 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 639 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 639 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 641 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 641 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 645 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 645 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 647 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 647 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 687 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 687 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 689 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 689 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 690 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 690 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 692 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 692 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 713 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 713 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 715 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 715 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 717 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 717 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 719 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 719 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 721 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 721 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 724 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 724 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 798 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 798 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 801 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 801 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 802 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 802 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 804 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 804 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 834 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 834 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 868 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 868 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 890 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 890 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 940 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 940 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 941 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 941 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 944 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 944 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 947 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 947 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 952 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 952 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1010 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1010 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1011 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1011 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1012 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1012 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1015 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1015 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1016 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1016 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1022 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1022 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1025 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1025 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1027 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1027 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1031 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1031 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1034 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1034 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1046 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1046 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1047 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1047 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1049 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1049 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1050 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1050 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1051 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1051 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1052 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1052 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1053 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1053 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1054 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1054 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1056 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1056 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1058 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1058 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1061 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1061 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1062 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1062 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1063 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1063 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1064 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1064 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1065 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1065 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1068 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1068 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1070 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1070 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1071 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1071 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1073 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1073 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1145 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1145 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1148 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1148 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1149 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1149 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1152 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1152 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1153 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1153 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1155 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1155 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1156 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1156 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1160 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1160 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1161 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1161 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1175 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1175 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1179 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1179 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1183 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1183 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1186 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1186 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1188 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1188 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1189 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1189 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1190 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1190 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1191 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1191 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1193 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1193 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1194 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1194 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1195 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1195 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1196 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1196 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1197 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1197 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1204 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1204 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1205 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1205 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1206 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1206 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1207 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1207 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1211 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1211 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1213 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1213 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1228 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1228 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1229 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1229 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1230 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1230 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1233 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1233 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1234 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1234 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1237 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1237 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1238 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1238 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1239 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1239 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1240 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1240 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1242 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1242 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1243 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1243 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1244 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1244 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1246 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1246 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1247 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1248 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1248 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1250 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1250 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1251 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1251 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1252 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1252 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1253 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1255 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1255 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1259 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1259 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1260 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1260 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1262 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1262 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1267 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1267 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1268 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1268 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1269 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1269 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1270 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1270 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1281 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1281 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1282 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1282 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1283 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1283 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1284 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1284 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1287 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1287 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1289 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1289 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1291 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1291 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1292 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1292 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1293 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1293 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1294 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1294 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1295 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1295 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1296 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1296 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1298 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1299 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1299 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1300 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1300 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1302 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1302 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1304 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1304 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1306 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1306 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1307 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1307 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1344 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1344 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1346 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1346 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1347 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1347 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1348 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1348 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1360 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1360 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1363 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1363 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1366 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1366 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and C-terminal to an amino acid residue corresponding to amino acid 1367 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide. In some cases, a Cas9 polypeptide of the present disclosure comprises: a) a Cas9 polypeptide; and b) a heterologous amino acid or heterologous polypeptide inserted internally within the Cas9 polypeptide, where the heterologous amino acid or heterologous polypeptide is inserted at a position that is immediately adjacent and N-terminal to an amino acid residue corresponding to amino acid 1367 of the Cas9 protein set forth in SEQ ID NO: 5, where the Cas9 fusion polypeptide retains cleavage and/or binding activity relative to the activity of the Cas9 polypeptide without the inserted heterologous amino acid or heterologous polypeptide.

As noted at the bottom of FIG. 20C (and as depicted in FIG. 22B as an illustrative example) in some cases, the last amino acid of the Cas9 sequence flanking the heterologous peptide at the N-terminus (at the junction of the N-terminal end of the heterologous polypeptide with the Cas9 polypeptide) is mutated. As an illustrative example, in the case depicted in FIG. 22B, there is a Q to H amino acid substitution at position 1027. In this case, the insert site is referred to as 1027 despite the presence of the mutation. Also as noted in FIG. 22B, these cases can be recognized when the amino acid of the Cas9 polypeptide that is N-terminal to the insertion site was mutated from an L, M, Q, K, E, W, or R to an F, I, H, N, D, C, or S, respectively.

Heterologous Polypeptides

A variety of heterologous polypeptides are suitable for inclusion in a Cas9 fusion polypeptide of the present disclosure. In some embodiments, the heterologous polypeptide can be fused to one or more internal portions (i.e., a portion other than the N- or C-terminus) of the Cas9 fusion polypeptide, as described herein. In some embodiments, the heterologous polypeptide is fused to the C-terminus of the Cas9 fusion polypeptide. In some embodiments, the heterologous polypeptide is fused to the N-terminus of the Cas9 fusion polypeptide. In some cases, a Cas9 fusion polypeptide of the present disclosure does not include a heterologous polypeptide fused to the N-terminus of the Cas9 polypeptide. In some cases, a Cas9 fusion polypeptide of the present disclosure does not include a heterologous polypeptide fused to the C-terminus of the Cas9 polypeptide. In some cases, a Cas9 fusion polypeptide of the present disclosure does not include a heterologous polypeptide fused to the C-terminus of the Cas9 polypeptide and does not include a heterologous polypeptide fused to the N-terminus of the Cas9 polypeptide.

The Cas9 fusion polypeptide can contain any convenient number of heterologous polypeptides at one or more insertion sites. Thus, the Cas9 fusion polypeptide can contain one or more, e.g., 2 or more, 3 or more, 4 or more, 5 or more, 7 or more, including 10 or more heterologous polypeptides, and can contain 15 or fewer, e.g., 12 or fewer, 10 or fewer, 8 or fewer, 6 or fewer, 4 or fewer, 3 or fewer, including 2 or fewer distinct heterologous polypeptides. In some cases, the Cas9 fusion polypeptide contains between 1 to 10, e.g., between 1 to 8, between 1 to 5, between 1 to 4, between 1 to 3, including between 1 to 2 heterologous polypeptides. Where the Cas9 fusion polypeptide contains more than one heterologous polypeptide, any two of the heterologous polypeptides may be the same or may be distinct heterologous polypeptides. In some cases, a Cas9 fusion polypeptide of the present disclosure comprises a single heterologous polypeptide inserted at a site internal to the Cas9 polypeptide. In some cases, a Cas9 fusion polypeptide of the present disclosure comprises 2 heterologous polypeptides inserted at two different sites internal to the Cas9 polypeptide.

A heterologous polypeptide suitable for inclusion in a Cas9 fusion polypeptide of the present disclosure can be any suitable length. In some cases, the length of the heterologous polypeptide is 1 amino acid or more, e.g., 5 amino acids or more, 10 amino acids or more, 15 amino acids or more, 20 amino acids or more, 25 amino acids or more, 30 amino acids or more, 40 amino acids or more, 50 amino acids or more, 75 amino acids or more, 100 amino acids or more, 150 amino acids or more, 200 amino acids or more, 300 amino acids or more, 400 amino acids or more, including 500 amino acids or more, and is 1000 amino acids or less, e.g., 750 amino acids or less, 600 amino acids or less, 500 amino acids or less, 400 amino acids or less, 350 amino acids or less, 300 amino acids or less, 250 amino acids or less, 200 amino acids or less, 150 amino acids or less, 125 amino acids or less, 100 amino acids or less, 75 amino acids or less, 50 amino acids or less, 40 amino acids or less, 35 amino acids or less, 30 amino acids or less, including 20 amino acids or less. A heterologous polypeptide suitable for inclusion in a Cas9 fusion polypeptide of the present disclosure can have a length in the range of about 1 to about 1000 amino acids, e.g. 1 to about 600 amino acids, 5 to about 500 amino acids, about 10 to about 400 amino acids, about 20 to about 300 amino acids, including about 50 to about 250 amino acids. A heterologous polypeptide suitable for inclusion in a Cas9 fusion polypeptide of the present disclosure can have a length in the range of from 5 amino acids to 20 amino acids, from 20 amino acids to 25 amino acids, from 25 amino acids to 50 amino acids, from 50 amino acids to 100 amino acids, from 100 amino acids to 150 amino acids, from 150 amino acids to 200 amino acids, or from 200 amino acids to 250 amino acids.

Suitable heterologous polypeptides for inclusion in a Cas9 fusion polypeptide of the present disclosure include, but are not limited to: 1) a member of a specific binding pair; 2) a polypeptide that confers an inducible conformational change on the Cas9 fusion polypeptide (e.g., a ligand binding domain of an estrogen receptor, an EF domain from calmodulin which specifically binds $Ca^{2+}$, and the like); 3) a targeting polypeptide that provides for binding to a cell surface moiety on a target cell or target cell type; 4) a polypeptide that provides an attachment site for a small molecule agent (e.g., a therapeutic agent); 5) a polypeptide (e.g., domain) that modifies DNA and/or or RNA (e.g., appends moieties such as methyl groups), 6) a polypeptide (e.g., domain) that can bind DNA and/or or RNA specifically, 7) a polypeptide (e.g., domain) that binds DNA and/or or RNA non-specifically, 8) a polypeptide (e.g., domain) that modifies proteins associated with DNA (e.g., methylates or acetylates a protein such as a histone), 9) a polypeptide (e.g., domain) that degrades DNA and/or RNA, 10) a polypeptide (e.g., domain) that polymerizes DNA and/or RNA, 11) a polypeptide (e.g., domain) that modulates transcription (e.g., represses transcription or activates transcription, 12) a polypeptide (e.g., domain) that covalently attaches to other polypeptide domains (e.g., spyCatcher), 13) any of the aforementioned polypeptides (e.g., domains) which have been engineered themselves e.g. a PDZ domain engineered for alternate specificity.

For example, in some cases, a Cas9 fusion polypeptide of the present disclosure is capable of sensing the physiological state of the cell and acting in a conditional fashion. For example, this sensing could be related to metabolism or the disorder of metabolism. There are a number of known periplasmic binding proteins and homologous bacterial transcriptions factors that have been validated to bind critical cellular metabolites including, but not limited, to those in glycolysis, the pentose phosphate pathway, the tricarboxylic acid (TCA) cycle, amino acid metabolism, nucleotide metabolism, and Warburg metabolism. As an example, higher levels of lactate can be correlated with altered metabolism and the progression towards cancer. For example, the heterologous polypeptide can be a lactate-binding protein (or fragment thereof), such as LldR, from *E. coli*; where the Cas9 fusion polypeptide comprising such a heterologous polypeptide has lactate-sensing ability. Following increased (or decreased) levels of lactate, the Cas9 fusion polypeptide could be used to initiate a gene editing or reprogramming.

In a similar fashion, in some cases, a Cas9 fusion polypeptide of the present disclosure exhibits the ability to sense a specific ion related to a change in cellular physiology; such ions include, but are not limited to, $Ca^{2+}$, $Zn^{2+}$, $Cu^{2+}$, $Na^{+}$, and Cl. There are numerous known protein domains that specifically bind these ions.

Specific Binding Pairs

In some cases, the heterologous polypeptide present in a Cas9 fusion polypeptide of the present disclosure is a member of a specific binding pair. Thus, for example, in some cases, a variant Cas9 polypeptide of the present disclosure comprises a heterologous polypeptide that binds a second polypeptide that is a specific binding partner of the heterologous polypeptide; in other words, in some cases, a variant Cas9 polypeptide of the present disclosure comprises a heterologous polypeptide that is a first member of a specific binding pair, where the variant Cas9 polypeptide binds a second polypeptide comprising a second member of the specific binding pair. The heterologous polypeptide may contain any member of a specific binding pair suitable for inserting into a Cas9 polypeptide. In certain embodiments, the specific binding pair undergoes binding through protein-protein interaction domains, such as, but not limited to, coiled-coil, zinc finger, RING finger, WD40 repeat, armadillo repeat, ankyrin repeat, src homology 2 (SH2-), SH3-, phosphotyrosine-bindin (PTB-), PDZ-, WW-, epidermal growth factor receptor substrate (EPS) 15 homology (EH-), LIM-, tetratrico peptide repeat region (TPR-), sterile alpha motif (SAM-), Ena/Vasp homology (EVH1-), or any other modular protein-protein interaction domains. Thus, in some cases, the heterologous polypeptide includes a coiled-coil, zinc finger, RING finger, WD40 repeat, armadillo repeat, ankyrin repeat, SH2-, SH3-, PTB-, PDZ-, WW-, EH-, LIM-, TPR-, SAM-, EVH1- or any other member of a modular protein-protein interaction domains. In some embodiments, the heterologous polypeptide includes a suitable binding partner for the coiled-coil, zinc finger, RING finger, WD40 repeat, armadillo repeat, ankyrin repeat, SH2-, SH3-, PTB-, PDZ-, WW-, EH-, LIM-, TPR-, SAM-, EVH1-, or any other member of the modular protein-protein interaction domains. The modular protein-protein interaction domain may be a suitable domain, or a derivative thereof, found in any suitable protein. Examples of proteins that contain modular protein-protein interaction domains are found in, e.g., PCT publication No. WO 2003056329, which is incorporated herein by reference.

In some cases, the heterologous polypeptide contains a PDZ domain. The heterologous polypeptide may contain a PDZ domain found in any suitable protein. In some cases, the heterologous polypeptide contains the alpha-1-syntrophin PDZ domain. In some cases, the heterologous polypeptide contains an amino acid sequence at least 90%, e.g., at least 95%, at least 98%, at least 99%, or 100% identical to the sequence set forth in SEQ ID NO:1079 (FIG. 21A). The specific binding partner for alpha-1-syntrophin PDZ domain is the peptide sequence GVKESLV (SEQ ID NO: 1084) at the C-terminus of a second protein. Thus a subject Cas9 fusion polypeptide that includes a heterologous polypeptide having an alpha-1-syntrophin PDZ domain, as described herein, can specifically bind a second polypeptide that includes the PDZ ligand amino acid sequence GVKESLV (SEQ ID NO: 1084) at the C-terminus via the interaction between the PDZ domain and the PDZ ligand amino acid sequence. Other PDZ domains suitable for including in the subject heterologous polypeptide is found in PDZ domain-containing proteins such as CASK, hDlg1, SHANK1, SHANK3, EBP-50, KIAA0807, TIP1, PSD-95, Pick1, CNK, GRIP, DVL-2, ZO-1, InaD, Par-6, Dvl, Tamalin, NHERF, nNOS, X11alpha, HtrA, etc. Examples of PDZ domain-containing proteins are found in, e.g., PCT publication Nos. WO 2003056329 and WO 2003004604, which are incorporated herein by reference.

In some cases, the heterologous polypeptide includes a PDZ domain ligand, which can bind to a PDZ domain, as described above. Any suitable PDZ domain ligand may be included in the heterologous polypeptide. PDZ domain ligands suitable for including in the subject heterologous polypeptide is found in PDZ domain ligand-containing proteins such as PAG, LPAP, ITK, DNAM-1, Shroom, PTEN, BLR-1, fyn, Vac14, Frizzled, Idax, Pals1, etc.

In certain embodiments, the heterologous polypeptide includes a coiled-coil domain. Examples of a suitable coiled-coil domains include, but are not limited to:

```
SYNZIP14:
                                        (SEQ ID NO: 1085)
NDLDAYEREAEKLEKKNEVLRNRLAALENELATLRQEVASMKQELQS;

SYNZIP17:
                                        (SEQ ID NO: 1086)
NEKEELKSKKAELRNRIEQLKQKREQLKQKIANLRKEIEAYK;
and

SYNZIP18:
                                        (SEQ ID NO: 1087)
SIAATLENDLARLENENARLEKDIANLERDLAKLEREEAYFs.
```

In some cases, the modular protein-protein interaction domain is a ligand-gated or inducible interaction domain. The heterologous polypeptide can include any suitable ligand-gated interaction domain or protein, such as, but not limited to, FK506 binding protein (FKBP); the FKBP12-rapamycin binding (FRB) domain (e.g., of mammalian target of rapamycin (mTOR); protein phosphatase 3, catalytic subunit, alpha isozyme (PPP3CA); the dimerization domain of gyrase B (GyrB); gibberellin insensitive dwarf1 (GID1); gibberellin insensitive (GAI); pyrabactin resistance (PYR) 1-like (PYL); abscisic acid (ABA) insensitive (BAI); dihydrofolate reductase (DHFR); DmrB; cryptochrome 2 (Cry2); CIB1, etc.

In some cases, a heterologous polypeptide inserted in a subject Cas9 fusion polypeptide is derived from FKBP1A (also known as FKBP12, FKBP1; PKC12; PKCI2; PPIASE; FKBP-12; FKBP-1A). For example, a suitable heterologous polypeptide can include a rapamycin binding portion of FKBP1A. For example, a suitable heterologous polypeptide can comprise an amino acid sequence having 75% or more amino acid sequence identity (e.g., 80% or more, 85% or more, 90% or more, 95% or more, 98% or more, or 100% amino acid sequence identity) to the following amino acid sequence (a rapamycin binding portion of FKBP1A):

```
                                        (SEQ ID NO: 1088)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE.
```

In some cases, a heterologous polypeptide inserted in a Cas9 fusion polypeptide is derived from protein phosphatase 3, catalytic subunit, alpha isozyme (PPP3CA) (also known as "Serine/threonine-protein phosphatase 2B catalytic subunit alpha isoform"; CNA; CALN; CALNA; CALNA1; CCN1; CNA1; PPP2B; "CAM-PRP catalytic subunit"; and "calmodulin-dependent calcineurin A subunit alpha isoform"). For example, a suitable heterologous polypeptide can include a binding portion of PPP3CA. For example, a suitable heterologous polypeptide can comprise an amino acid sequence having 75% or more amino acid sequence identity (e.g., 80% or more, 85% or more, 90% or more, 95% or more, 98% or more, or 100% amino acid sequence identity) to the following amino acid sequence (PP2Ac domain):

```
                                        (SEQ ID NO: 1089)
LEESVALRIITEGASILRQEKNLLDIDAPVTVCGDIHGQFFDLMKLFEVG

GSPANTRYLFLGDYVDRGYFSIECVLYLWALKILYPKTLFLLRGNHECRH

LTEYFTFKQECKIKYSERVYDACMDAFDCLPLAALMNQQFLCVHGGLSPE

INTLDDIRKLDRFKEPPAYGPMCDILWSDPLEDFGNEKTQEHFTHNTVRG

CSYFYSYPAVCEFLQHNNLLSILRAHEAQDAGYRMYRKSQTTGFPSLITI

FSAPNYLDVYNNKAAVLKYENNVMNIRQFNCSPHPYWLPNFM.
```

In some cases, a heterologous polypeptide inserted in a Cas9 fusion polypeptide is derived from cyclophilin (also known cyclophilin A, PPIA, CYPA, CYPH, PPIase A, etc.). For example, a suitable heterologous polypeptide can include a binding portion of cyclophilin. For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to the following amino acid sequence:

```
                                        (SEQ ID NO: 1090)
MVNPTVFFDIAVDGEPLGRVSFELFADKVPKTAENFRALSTGEKGFGYKG

SCFHRIIPGFMCQGGDFTRHNGTGGKSIYGEKFEDENFILKHTGPGILSM

ANAGPNTNGSQFFICTAKTEWLDGKHVVFGKVKEGMNIVEAMERFGSRNG

KTSKKITIADCGQLE.
```

In some cases, a heterologous polypeptide inserted in a Cas9 fusion polypeptide is derived from MTOR (also known as FKBP-rapamycin associated protein; FK506 binding protein 12-rapamycin associated protein 1; FK506 binding protein 12-rapamycin associated protein 2; FK506-binding protein 12-rapamycin complex-associated protein 1; FRAP; FRAP1; FRAP2; RAFT1; and RAPT1). For example, a suitable heterologous polypeptide can include the Fkbp-Rapamycin Binding Domain (also known as FRB). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to the following amino acid sequence (FRB):

```
                                        (SEQ ID NO: 1091)
VAILWHEMWHEGLEEASRLYFGERNVKGMFEVLEPLHAMMERGPQTLKET

SFNQAYGRDLMEAQEWCRKYMKSGNVKDLTQAWDLYYHVFRRIS.
```

Rapamycin can serve as a ligand for inducing interaction between protein-protein interaction domains, such as between FKBP1A (e.g., a rapamycin binding portion) and FKBP1A (e.g., a rapamycin binding portion); FKBP1A (e.g., a rapamycin binding portion) and FRB (Fkbp-Rapamycin Binding Domain); FKBP1A (e.g., a rapamycin binding portion) and CnA (calcineurin catalytic subunit A)

and FKBP1A (e.g., a rapamycin binding portion) and cyclophilin. Alternatively, a rapamycin derivative or analog can be used. See, e.g., WO96/41865; WO 99/36553; WO 01/14387; and Ye et al (1999) Science 283:88-91. For example, analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional information is presented in, e.g., U.S. Pat. Nos. 5,525,610; 5,310,903 5,362,718; and 5,527,907. Selective epimerization of the C-28 hydroxyl group has been described; see, e.g., WO 01/14387. Additional synthetic ligands suitable for use as an alternative to rapamycin include those described in U.S. Patent Publication No. 2012/0130076.

Rapamycin has the structure:

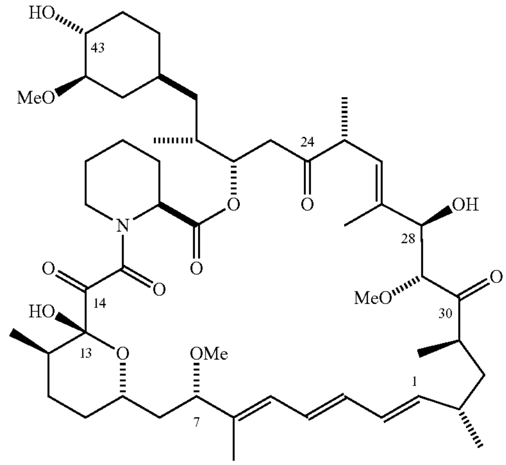

Rapamycin

Suitable rapalogs include, e.g.,

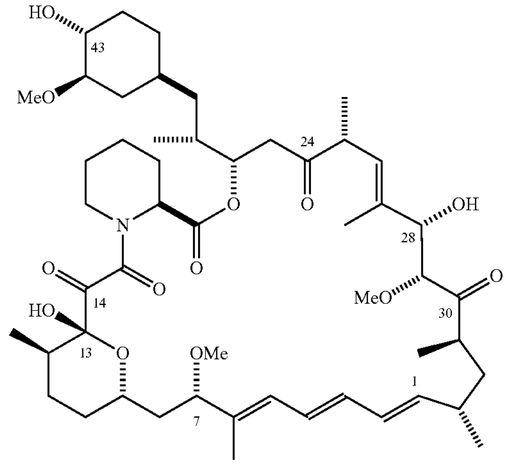

28-eplrapamycin

Also suitable as a rapalog is a compound of the formula:

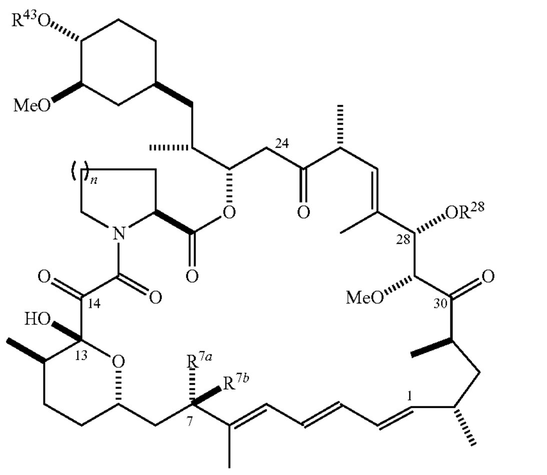

where n is 1 or 2; $R^{28}$ and $R^{43}$ are independently H, or a substituted or unsubstituted aliphatic or acyl moiety; one of $R^{7a}$ and $R^{7b}$ is H and the other is halo, $R^A$, $OR^A$, $SR^A$, $—OC(O)R^A$, $—OC(O)NR^AR^B$, $—NR^AR^B$, $—NR^BC(OR)R^A$, $NR^BC(O)OR^A$, $—NR^BSO_2R^A$, or $NR^BSO_2NR^AR^{B'}$; or $R^{7a}$ and $R^{7b}$, taken together, are H in the tetraene moiety:

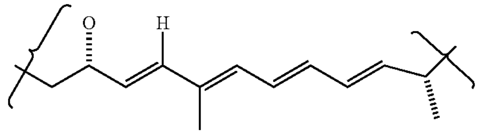

where $R^A$ is H or a substituted or unsubstituted aliphatic, heteroaliphatic, aryl, or heteroaryl moiety and where $R^B$ and $R^{B'}$ are independently H, OH, or a substituted or unsubstituted aliphatic, heteroaliphatic, aryl, or heteroaryl moiety.

In some cases, a heterologous polypeptide present in a Cas9 fusion polypeptide is derived from GyrB (also known as DNA gyrase subunit B). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 200 amino acids (aa), from about 200 aa to about 300 aa, from about 300 aa to about 400 aa, from about 400 aa to about 500 aa, from about 500 aa to about 600 aa, from about 600 aa to about 700 aa, or from about 700 aa to about 800 aa, of the following GyrB amino acid sequence from *Escherichia coli* (or to the DNA gyrase subunit B sequence from any organism): MSNSYDSSSIKVLKGLDAVRKRPGMYIGDTDDGTGLHHMVFEVVDNAIDEALAGHCKE IIVTIHADNSVSVQDDGRGIPTGIHPEEGVSAAEVIMTVLHAGGKFDDNSYKVSGGLHGV GVSVVNALSQKLELVIQREGKIHRQIYEHGVPQAPLAVTGETEKTGTMVRFWPSLETFT NVTEFEYEILAKRLRELSFLNSGVSIRLRDKRDGKEDHFHYEGGIKAFVEYLNKNKTPIH PNIFYFSTEKDGIGVEVALQWNDGFQENIYCFTNNIPQRDGGTHLAGFRAAMTRTLNAY MDKEGYSKKAKVSATGDDAREGLIAVVSVKVPDPKFSSQTKDKLVSSEVKSAVEQQM NELLAEYLLENPTDAKIVVGKIIDAARAREAARRAREMTRRKGALDLAGLPGKLA- DCQ ERDPALSELYLVEGDSAGGSAKQGRNRKNQA-ILPLKGKILNVEKARFDKMLSSQEVATL ITALGC-GIGRDEYNPDKLRYHSIIIMTDADVDGSHIRTLLLTF-FYRQMPEIVERGHVYIAQ PPLYKVKKGKQEQYIKD-DEAMDQYQISIALDGATLHTNASAPALAGEALEKLV-SEYNA TQKMINRMERRYPKAMLKELIYQPTL-TEADLSDEQTVTRWVNALVSELNDKEQHGSQ WKFDVHTNAEQNLFEPIVRVRTHGVDTDYPLDHE-FITGGEYRRICTLGEKLRGLLEEDA FIERGERRQP-VASFEQALDWLVKESRRGLSIQRYKGLGEMNPE-QLWETTMDPESRRML RVTVKDAIAADQLFTTLMG-DAVEPRRAFIEENALKAANIDI (SEQ ID NO:1092). In some cases, a heterologous polypeptide includes an amino acid sequence having 75% or more amino acid sequence identity (e.g., 80% or more, 85% or more, 90% or more, 95% or more, 98% or more, or 100% amino acid sequence identity) to amino acids 1-220 of the above-listed GyrB amino acid sequence from *Escherichia coli.*

Coumermycin can serve as a ligand for inducing interaction between protein-protein interaction domains, such as between GyrB and GyrB. Alternatively, a coumermycin analog can be used. See, e.g., Farrar et al. (1996) Nature 383:178-181; and U.S. Pat. No. 6,916,846.

In some cases, a heterologous polypeptide inserted in a Cas9 fusion polypeptide is derived from DHFR (also known as dihydrofolate reductase, DHFRP1, and DYR). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to the following amino acid sequence:

```
                                        (SEQ ID NO: 1093)
MVGSLNCIVAVSQNMGIGKNGDLPWPPLRNEFRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND.
```

In some cases, methotrexate, e.g., a non-cytotoxic, homo-bifunctional methotrexate dimer can serve as a ligand for inducing interaction between protein-protein interaction domains, such as between DHFR and DHFR. See, e.g., U.S. Pat. No. 8,236,925.

In some cases, a heterologous polypeptide inserted in a Cas9 fusion polypeptide is derived from the DmrB binding domain (i.e., DmrB homodimerization domain). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to the following amino acid sequence:

```
                                        (SEQ ID NO: 1094)
MASRGVQVETISPGDGRTFPKRGQTCVVHYTGMLEDGKKVDSSRDRNKPF

KFMLGKQEVIRGWEEGVAQMSVGQRAKLTISPDYAYGATGHPGIIPPHAT

LVFDVELLKLE.
```

In some cases, a heterologous polypeptide inserted in a Cas9 fusion polypeptide is derived from a PYL protein (also known as abscisic acid receptor and as RCAR). For example a subject heterologous polypeptide can be derived from proteins such as those of *Arabidopsis thaliana*: PYR1, RCAR1(PYL9), PYL1, PYL2, PYL3, PYL4, PYL5, PYL6, PYL7, PYL8 (RCAR3), PYL10, PYL11, PYL12, PYL13. For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to the following amino acid sequences:

```
PYL10:
                                        (SEQ ID NO: 1095)
MNGDETKKVESEYIKKHHRHELVESQCSSTLVKHIKAPLHLVWSIVRRFD

EPQKYKPFISRCVVQGKKLEVGSVREVDLKSGLPATKSTEVLEILDDNEH

ILGIRIVGGDHRLKNYSSTISLHSETIDGKTGTLAIESFVVDVPEGNTKE

ETCFFVEALIQCNLNSLADVTERLQAESMEKKI;

PYL11:
                                        (SEQ ID NO: 1096)
METSQKYHTCGSTLVQTIDAPLSLVWSILRRFDNPQAYKQFVKTCNLSSG

DGGEGSVREVTVVSGLPAEFSRERLDELDDESHVMMISIIGGDHRLVNYR

SKTMAFVAADTEEKTVVVESYVVDVPEGNSEEETTSFADTIVGFNLKSLA

KLSERVAHLKL

PYL12:
                                        (SEQ ID NO: 1097)
MKTSQEQHVCGSTVVQTINAPLPLVWSILRRFDNPKTFKHFVKTCKLRSG

DGGEGSVREVTVVSDLPASFSLERLDELDDESHVMVISIIGGDHRLVNYQ

SKTTVFVAAEEEKTVVVESYVVDVPEGNTEEETTLFADTIVGCNLRSLAK

LSEKMMELT.

PYL13:
                                        (SEQ ID NO: 1098)
MESSKQKRCRSSVVETIEAPLPLVWSILRSFDKPQAYQRFVKSCTMRSGG

GGGKGGEGKGSVRDVTLVSGFPADFSTERLEELDDESHVMVVSIIGGNHR

LVNYKSKTKVVASPEDMAKKTVVVESYVVDVPEGTSEEDTIFFVDNIIRY

NLTSLAKLTKKMMK.

PYL1:
                                        (SEQ ID NO: 1099)
MANSESSSSPVNEEENSQRISTLHHQTMPSDLTQDEFTQLSQSIAEFHTY

QLGNGRCSSLLAQRIHAPPETVWSVVRRFDRPQIYKHFIKSCNVSEDFEM

RVGCTRDVNVISGLPANTSRERLDLLDDDRRVTGFSITGGEHRLRNYKSV

TTVHRFEKEEEEERIWTVVLESYVVDVPEGNSEEDTRLFADTVIRLNLQK

LASITEAMNRNNNNNNNSSQVR.

PYL2:
                                        (SEQ ID NO: 1100)
MSSSPAVKGLTDEEQKTLEPVIKTYHQFEPDPTTCTSLITQRIHAPASVV

WPLIRRFDNPERYKHFVKRCRLISGDGDVGSVREVTVISGLPASTSTERL

EFVDDDHRVLSFRVVGGEHRLKNYKSVTSVNEFLNQDSGKVYTVVLESYT

VDIPEGNTEEDTKMFVDTVVKLNLQKLGVAATSAPMHDDE.

PYL3:
                                        (SEQ ID NO: 1101)
MNLAPIHDPSSSSTTTTSSSTPYGLTKDEFSTLDSIIRTHHTFPRSPNTC

TSLIAHRVDAPAHAIWRFVRDFANPNKYKHFIKSCTIRVNGNGIKEIKVG

TIREVSVVSGLPASTSVEILEVLDEEKRILSFRVLGGEHRLNNYRSVTSV

NEFVVLEKDKKKRVYSVVLESYIVDIPQGNTEEDTRMFVDTVVKSNLQNL

AVISTASPT.
```

-continued

PYL4:

(SEQ ID NO: 1102)

MLAVHRPSSAVSDGDSVQIPMMIASFQKRFPSLSRDSTAARFHTHEVGPN

QCCSAVIQEISAPISTVWSVVRRFDNPQAYKHFLKSCSVIGGDGDNVGSL

RQVHVVSGLPAASSTERLDILDDERHVISFSVVGGDHRLSNYRSVTTLHP

SPISGTVVVESYVVDVPPGNTKEETCDFVDVIVRCNLQSLAKIAENTAAE

SKKKMSL.

PYL5:

(SEQ ID NO: 1103)

MRSPVQLQHGSDATNGFHTLQPHDQTDGPIKRVCLTRGMHVPEHVAMHHT

HDVGPDQCCSSVVQMIHAPPESVWALVRRFDNPKVYKNFIRQCRIVQGDG

LHVGDLREVMVVSGLPAVSSTERLEILDEERHVISFSVVGGDHRLKNYRS

VTTLHASDDEGTVVVESYIVDVPPGNTEEETLSFVDTIVRCNLQSLARST

NRQ.

PYL6:

(SEQ ID NO: 1104)

MPTSIQFQRSSTAAEAANATVRNYPHHHQKQVQKVSLTRGMADVPEHVEL

SHTHVVGPSQCFSVVVQDVEAPVSTVWSILSRFEHPQAYKHFVKSCHVVI

GDGREVGSVREVRVVSGLPAAFSLERLEIMDDDRHVISFSVVGGDHRLMN

YKSVTTVHESEEDSDGKKRTRVVESYVVDVPAGNDKEETCSFADTIVRCN

LQSLAKLAENTSKFS.

PYL7:

(SEQ ID NO: 1105)

MEMIGGDDTDTEMYGALVTAQSLRLRHLHHCRENQCTSVLVKYIQAPVHL

VWSLVRRFDQPQKYKPFISRCTVNGDPEIGCLREVNVKSGLPATTSTERL

EQLDDEEHILGINIIGGDHRLKNYSSILTVHPEMIDGRSGTMVMESFVVD

VPQGNTKDDTCYFVESLIKCNLKSLACVSERLAAQDITNSIATFCNASNG

YREKNHTETNL.

PYL8:

(SEQ ID NO: 1106)

MEANGIENLTNPNQEREFIRRHHKHELVDNQCSSTLVKHINAPVHIVWSL

VRRFDQPQKYKPFISRCVVKGNMEIGTVREVDVKSGLPATRSTERLELLD

DNEHILSIRIVGGDHRLKNYSSIISLHPETIEGRIGTLVIESFVVDVPEG

NTKDETCYFVEALIKCNLKSLADISERLAVQDTTESRV.

PYL9:

(SEQ ID NO: 1107)

MMDGVEGGTAMYGGLETVQYVRTHHQHLCRENQCTSALVKHIKAPLHLVW

SLVRRFDQPQKYKPFVSRCTVIGDPEIGSLREVNVKSGLPATTSTERLEL

LDDEEHILGIKIIGGDHRLKNYSSILTVHPEIIEGRAGTMVIESFVVDVP

QGNTKDETCYFVEALIRCNLKSLADVSERLASQDITQ.

PYR1:

(SEQ ID NO: 1108)

MPSELTPEERSELKNSIAEFHTYQLDPGSCSSLHAQRIHAPPELVWSIVR

RFDKPQTYKHFIKSCSVEQNFEMRVGCTRDVIVISGLPANTSTERLDILD

DERRVTGFSIIGGEHRLTNYKSVTTVHRFEKENRIWTVVLESYVVDMPEG

NSEDDTRMFADTVVKLNLQKLATVAEAMARNSGDGSGSQVT.

In some cases, a heterologous polypeptide inserted in a Cas9 fusion polypeptide is derived from an ABI protein (also known as Abscisic Acid-Insensitive). For example a subject heterologous polypeptide can be derived from proteins such as those of *Arabidopsis thaliana*: ABI1 (Also known as ABSCISIC ACID-INSENSITIVE 1, Protein phosphatase 2C 56, AtPP2C56, P2C56, and PP2C ABI1) and/or ABI2 (also known as P2C77, Protein phosphatase 2C 77, AtPP2C77, ABSCISIC ACID-INSENSITIVE 2, Protein phosphatase 2C ABI2, and PP2C ABI2). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

ABI1:

(SEQ ID NO: 1109)

MEEVSPAIAGPFRPFSETQMDFTGIRLGKGYCNNQYSNQDSENGDLMVSL

PETSSCSVSGSHGSESRKVLISRINSPNLNMKESAAADIVVVDISAGDEI

NGSDITSEKKMISRTESRSLFEFKSVPLYGFTSICGRRPEMEDAVSTIPR

FLQSSSGSMLDGRFDPQSAAHFFGVYDGHGGSQVANYCRERMHLALAEEI

AKEKPMLCDGDTWLEKWKKALFNSFLRVDSEIESVAPETVGSTSVVAVVF

PSHIFVANCGDSRAVLCRGKTALPLSVDHKPDREDEAARIEAAGGKVIQW

NGARVFGVLAMSRSIGDRYLKPSIIPDPEVTAVKRVKEDDCLILASDGVW

DVMTDEEACEMARKRILLWHKKNAVAGDASLLADERRKEGKDPAAMSAAE

YLSKLAIQRGSKDNISVVVVDLKPRRKLKSKPLN;

and

ABI2:

(SEQ ID NO: 1110)

MDEVSPAVAVPFRPFTDPHAGLRGYCNGESRVTLPESSCSGDGAMKDSSF

EINTRQDSLTSSSSAMAGVDISAGDEINGSDEFDPRSMNQSEKKVLSRTE

SRSLFEFKCVPLYGVTSICGRRPEMEDSVSTIPRFLQVSSSSLLDGRVTN

GFNPHLSAHFFGVYDGHGGSQVANYCRERMHLALTEEIVKEKPEFCDGDT

WQEKWKKALFNSFMRVDSEIETVAHAPETVGSTSVVAVVFPTHIFVANCG

DSRAVLCRGKTPLALSVDHKPDRDDEAARIEAAGGKVIRWNGARVFGVLA

MSRSIGDRYLKPSVIPDPEVTSVRRVKEDDCLILASDGLWDVMTNEEVCD

LARKRILLWHKKNAMAGEALLPAEKRGEGKDPAAMSAAEYLSKMALQKGS

KDNISVVVVDLKGIRKFKSKSLN.

In some cases, a heterologous polypeptide inserted in a subject Cas9 fusion polypeptide is derived from a Cry2 protein (also known as cryptochrome 2). For example a subject heterologous polypeptide can be derived from Cry2 proteins from any organism (e.g., a plant) such as, but not limited to, those of *Arabidopsis thaliana*. For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequence:

Cry2 (*Arabidopsis thaliana*)

(SEQ ID NO: 1111)

MKMDKKTIVWFRRDLRIEDNPALAAAAHEGSVFPVFIWCPEEEGQFYPGR

ASRWWMKQSLAHLSQSLKALGSDLTLIKTHNTISAILDCIRVTGATKVVF

NHLYDPVSLVRDHTVKEKLVERGISVQSYNGDLLYEPWEIYCEKGKPFTS

FNSYWKKCLDMSIESVMLPPPWRLMPITAAAEAIWACSIEELGLENEAEK

PSNALLTRAWSPGWSNADKLLNEFIEKQLIDYAKNSKKVVGNSTSLLSPY

LHFGEISVRHVFQCARMKQIIWARDKNSEGEESADLFLRGIGLREYSRYI

CFNFPFTHEQSLLSHLRFFPWDADVDKFKAWRQGRTGYPLVDAGMRELWA

TGWMHNRIRVIVSSFAVKFLLLPWKWGMKYFWDTLLDADLECDILGWQYI

SGSIPDGHELDRLDNPALQGAKYDPEGEYIRQWLPELARLPTEWIHHPWD

APLTVLKASGVELGTNYAKPIVDIDTARELLAKAISRTREAQIMIGAAPD

EIVADSFEALGANTIKEPGLCPSVSSNDQQVPSAVRYNGSKRVKPEEEEE

RDMKKSRGFDERELFSTAESSSSSSVFFVSQSCSLASEGKNLEGIQDSSD

QITTSLGKNGCK.

In some cases, a heterologous polypeptide inserted in a subject Cas9 fusion polypeptide is derived from the CIB1 *Arabidopsis thaliana* protein (also known as transcription factor bHLH63). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 1112)

MNGAIGGDLLLNFPDMSVLERQRAHLKYLNPTFDSPLAGFFADSSMITGG

EMDSYLSTAGLNLPMMYGETTVEGDSRLSISPETTLGTGNFKKRKFDTET

KDCNEKKKKMTMNRDDLVEEGEEEKSKITEQNNGSTKSIKKMKHKAKKEE

NNFSNDSSKVTKELEKTDYIHVRARRGQATDSHSIAERVRREKISERMKF

LQDLVPGCDKITGKAGMLDEIINYVQSLQRQIEFLSMKLAIVNPRPDFDM

DDIFAKEVASTPMTVVPSPEMVLSGYSHEMVHSGYSSEMVNSGYLHVNPM

QQVNTSSDPLSCFNNGEAPSMWDSHVQNLYGNLGV.

In some cases, a heterologous polypeptide inserted in a subject Cas9 fusion polypeptide is derived from the GAI *Arabidopsis thaliana* protein (also known as Gibberellic Acid Insensitive, and DELLA protein GAI). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 1113)

MKRDHHHHHHQDKKTMMMNEEDDGNGMDELLAVLGYKVRSSEMADVAQKL

EQLEVMMSNVQEDDLSQLATETVHYNPAELYTWLDSMLTDLNPPSSNAEY

DLKAIPGDAILNQFAIDSASSSNQGGGGDTYTTNKRLKCSNGVVETTTAT

AESTRHVVLVDSQENGVRLVHALLACAEAVQKENLTVAEALVKQIGFLAV

SQIGAMRKVATYFAEALARRIYRLSPSQSPIDHSLSDTLQMHFYETCPYL

KFAHFTANQAILEAFQGKKRVHVIDFSMSQGLQWPALMQALALRPGGPPV

FRLTGIGPPAPDNFDYLHEVGCKLAHLAEAIHVEFEYRGFVANTLADLDA

SMLELRPSEIESVAVNSVFELHKLLGRPGAIDKVLGVVNQIKPEIFTVVE

QESNHNSPIFLDRFTESLHYYSTLFDSLEGVPSGQDKVMSEVYLGKQICN

VVACDGPDRVERHETLSQWRNRFGSAGFAAAHIGSNAFKQASMLLALFNG

GEGYRVEESDGCLMLGWHTRPLIATSAWKLSTN.

In some cases, a heterologous polypeptide inserted in a subject Cas9 fusion polypeptide is derived from a GID1 *Arabidopsis thaliana* protein (also known as Gibberellin receptor GID1). For example, a suitable heterologous polypeptide can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences: GID1A:

GID1A:

(SEQ ID NO: 1114)

MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC.

GID1B:

(SEQ ID NO: 1115)

MAGGNEVNLNECKRIVPLNTWVLISNFKLAYKVLRRPDGSFNRDLAEFLD

RKVPANSFPLDGVFSFDHVDSTTNLLTRIYQPASLLHQTRHGTLELTKPL

-continued

```
STTEIVPVLIFFHGGSFTHSSANSAIYDTFCRRLVTICGVVVVSVDYRRS

PEHRYPCAYDDGWNALNWVKSRVWLQSGKDSNVYVYLAGDSSGGNIAHNV

AVRATNEGVKVLGNILLHPMFGGQERTQSEKTLDGKYFVTIQDRDWYWRA

YLPEGEDRDHPACNPFGPRGQSLKGVNFPKSLVVVAGLDLVQDWQLAYVD

GLKKTGLEVNLLYLKQATIGFYFLPNNDHFHCLMEELNKFVHSIEDSQSK

SSPVLLTP
```

GID1C:

(SEQ ID NO: 1116)

```
MAGSEEVNLIESKTVVPLNTWVLISNFKLAYNLLRRPDGTFNRHLAEFLD

RKVPANANPVNGVFSFDVIIDRQTNLLSRVYRPADAGTSPSITDLQNPVD

GEIVPVIVFFHGGSFAHSSANSAIYDTLCRRLVGLCGAVVVSVNYRRAPE

NRYPCAYDDGWAVLKWVNSSSWLRSKKDSKVRIFLAGDSSGGNIVHNVAV

RAVESRIDVLGNILLNPMFGGTERTESEKRLDGKYFVTVRDRDWYWRAFL

PEGEDREHPACSPFGPRSKSLEGLSFPKSLVVVAGLDLIQDWQLKYAEGL

KKAGQEVKLLYLEQATIGFYLLPNNNHFHTVMDEIAAFVNAECQ.
```

Allosteric Modulation

In some cases, the heterologous polypeptide present in a Cas9 fusion polypeptide of the present disclosure confers an inducible conformational change on the Cas9 fusion polypeptide. In some cases, a variant Cas9 polypeptide of the present disclosure comprises a heterologous polypeptide that modifies the ability of the Cas9 polypeptide to bind to and/or cleave a target nucleic acid. For example, in some cases, a variant Cas9 polypeptide of the present disclosure comprises a heterologous polypeptide that reversibly modifies the ability of the Cas9 polypeptide to bind to and/or cleave a target nucleic acid (e.g., the heterologous polypeptide can confer an inducible conformational change on the Cas9 fusion polypeptide). The heterologous polypeptide can modify the ability of the Cas9 polypeptide to bind to and/or cleave a target nucleic acid by an allosteric mechanism, e.g., where binding of a small molecule to the heterologous polypeptide induces a conformational change in the variant Cas9 polypeptide. In some cases, the small molecule enhances the ability of the Cas9 polypeptide to bind to and/or cleave a target nucleic acid. In some cases, the small molecule reduces the ability of the Cas9 polypeptide to bind to and/or cleave a target nucleic acid.

The heterologous polypeptide that confers allosteric modulation of Cas9 may be any suitable polypeptide domain that changes conformation upon binding of a ligand (and thus confers an inducible conformational change on the Cas9 fusion polypeptide), e.g., a small molecule, hormone, cellular metabolite, ions, etc. The heterologous polypeptide may include all, or at least a ligand binding domain, of a metal ion-binding protein, cyclic nucleotide-binding protein (e.g., cAMP-dependent protein kinase, cGMP-dependent protein kinase, cyclic nucleotide-gated channel), hydrolase, ATP-binding protein, GTP-binding protein, nitric monoxide synthase, bacterial metabolite sensing proteins (e.g., glucose-binding protein, maltose-binding protein), hormone receptor, G-protein coupled receptor (GPCR), etc.

In some cases, the heterologous polypeptide includes a calcium binding protein, or a calcium binding domain thereof. The calcium binding protein may be any suitable calcium binding protein, such as, but not limited to, EF-hand containing proteins or a calcium-sensing GPCR. Suitable EF-hand containing proteins include, without limitation, calmodulin, troponin C, and S100 proteins. In some embodiments, the heterologous peptide includes one or more, e.g., 2 or more, 3 or more, and up to 4 EF hand domains of the EF-hand containing protein, such as troponin C and calmodulin. In some cases, the heterologous peptide includes an EF-hand containing polypeptide, e.g., calmodulin, and a helical peptide that binds to the EF-hand containing polypeptide when the EF-hand containing polypeptide is bound to calcium. The helical peptide may be the M13 domain of a myosin light chain kinase, or any other suitable helical peptide.

In some cases, the heterologous polypeptide includes a zinc binding protein, or a suitable zinc binding domain thereof. The zinc binding protein may be any suitable zinc binding protein, such as, but not limited to, zinc finger containing proteins and metallothioneins. Suitable zinc finger containing proteins include, without limitation, zinc-responsive transcription factor (Zap1) and metal regulatory transcription factor 1 (MTF1). In some embodiments, the heterologous peptide includes one or more, e.g., 2 or more, 3 or more, and up to 4 zinc finger domains of the zinc finger containing protein, such as Zap-1 and MTF1.

In some cases, the heterologous polypeptide includes a magnesium binding protein, or a suitable magnesium binding domain thereof. The magnesium binding protein may be any suitable magnesium binding protein, such as, but not limited to, human centrin protein 3.

In some cases, the heterologous polypeptide includes a cyclic monophosphate nucleotide (e.g., cAMP, cGMP) binding protein, or a suitable binding domain thereof. The heterologous polypeptide may include a cyclic nucleotide binding domain from any suitable cyclic nucleotide binding protein, including, but not limited to, protein kinase A (PKA), exchange protein activated by cyclic AMP (epac), protein kinase G (PKG), phosphodiesterase, and MloK1.

In some embodiments, the heterologous polypeptide includes a GTP-binding protein, e.g., a small GTPase protein (G protein). The GTP-binding protein may be any suitable GTP-binding protein. In certain cases, the heterologous polypeptide includes a G protein, including, but not limited to, Ras, Rho, Ran, Rab and Arf GTPases. In some cases, the heterologous polypeptide includes a G protein (e.g., Ras, Rap 1) and a G-protein binding domain of a G-protein-interacting protein (e.g., Raf kinase).

In some cases, the heterologous polypeptide includes a bacterial metabolite sensing proteins, such as a periplasmic binding protein (PBP). The heterologous polypeptide may include any suitable PBP, such as, but not limited to glucose-binding protein, maltose-binding protein, etc., or a suitable binding domain thereof. The glucose-binding protein may be any suitable glucose-binding protein, such as, but not limited to, MglB.

In some cases, the heterologous polypeptide includes a receptor, e.g., a hormone receptor, metabolite receptor, GPCR, or any other suitable receptor, or a suitable portion thereof. In some cases, the heterologous polypeptide includes a hormone receptor, or a portion thereof. In some cases, the heterologous polypeptide includes a ligand-binding domain of the hormone receptor. The hormone receptor may be any suitable hormone receptor, including, but not limited to an estrogen receptor, estrogen-related receptor, androgen receptor, glucocorticoid receptor, mineralocorticoid receptor, progesterone receptor, retinoic acid receptor, vitamin D receptor, thyroid hormone receptor, peroxisome proliferator-activated receptor (PPAR), Rev-ErbA receptor, RAR-related orphan receptor, liver X receptor, farnesoid X receptor, pregnane X receptor, constitutive androstane receptor, hepatocyte nuclear factor-4, retinoid receptor, testicular receptor, nerve growth factor IB, nuclear receptor related 1, neuron-derived orphan receptor, steroidogenic factor 1, liver receptor homolog-1, germ cell nuclear factor, or any other hormone receptor. In some cases, the hormone receptor is an estrogen receptor. In certain embodiments, the heterologous polypeptide contains the ligand binding domain of an estrogen receptor, e.g., estrogen receptor alpha. In some cases, the heterologous polypeptide contains an amino acid sequence at least 90%, e.g., at least 95%, at least 98%, at least 99%, or 100% identical to the sequence set forth in SEQ ID NO:1080 (FIG. 21B).

The heterologous polypeptide that confers allosteric modulation of Cas9 may be any suitable polypeptide domain that changes conformation upon post-translational modification of the domain, including, but not limited to phosphorylation, acetylation, formylation, methylation, amidation, butyrylation, gamma-carboxylation, glycosylation, malonylation, hydroxylation, ADP-ribosylation, oxidation, adenylylation, propionylation, S-glutathionylation, S-nitrosylation, succinylation, sulfation, ubiquitination, SUMOylation, Neddylation, Pupylation. In some embodiments, the heterologous polypeptide includes a substrate for post-translational modification. In some instances, the heterologous polypeptide includes a substrate for post-translational modification, and a binding domain that binds the substrate upon post-translational medication. Thus, in some embodiments, the heterologous polypeptide includes a PKA substrate peptide from a cAMP response element binding protein (CREB). In some cases, the heterologous polypeptide includes a PKA substrate peptide from CREB and a phospho-peptide binding domain (such as a phosphoserine/threonine binding domain from a 14-3-3 protein). In some cases, the substrate is a mitogen-activated protein kinase (MAPK) substrate and the binding domain is a phospho-peptide binding domain (e.g., a MAPK substrate peptide from Cdc25C, and the proline-directed WW phospho-binding domain; a MAPK substrate peptide from the Epidermal Growth Factor Receptor (EGFR), and the Forkhead-Associated 2 domain). In certain embodiments, the heterologous polypeptide contains a kinase substrate in Src, Abl or EGFR and a phosphotyrosine binding SH2 domain. In some embodiments, the heterologous polypeptide contains a kinase substrate for autophosphorylation in human Cyclin B 1 and a Polo Box Domain of Plk1. The heterologous polypeptide can include any other suitable combination of a post-translational modification substrate and a corresponding post-translational modification binding domain.

The heterologous polypeptide that confers allosteric modulation of Cas9 may be any suitable polypeptide domain that changes conformation upon exposure to electromagnetic radiation, e.g., exposure to an appropriate wavelength of light. The light-sensitive heterologous polypeptide may be derived from any suitable light-sensitive protein. Examples of light-sensitive proteins include, but are not limited to, Light-Oxygen-Voltage (LOV), Cryptochrome (CRYs), Blue-light-using FAD (BLUF), Phytochrome (PHY), UVR8, and opsin families of proteins. In some instances, the heterologous polypeptide may include all, or a suitable portion thereof, of the LOV2 domain of *Avena sativa* phototropin 1 (AsLOV2), a fungal circadian clock photoreceptor Vivid (VVD), a *Bacillus subtilis* stress response protein (YtvA), a FLAVIN-BINDING, KELCH REPEAT, F-BOX 1 essential to plant flowering (FKF1), and a 222 amino acid LOV-transcription factor present in *Erythrobacter litoralis* (EL222). For additional examples, see, e.g., Kawano et al., Nat Commun. 2015 Feb. 24; 6:6256, which discloses pairs of distinct photoswitches called 'magnets' engineered to recognize each other based on electrostatic interactions.

Signaling Polypeptides

In some cases, a Cas9 fusion polypeptide of the present disclosure comprises a heterologous polypeptide that is a substrate for post-translational modification of the variant Cas9 polypeptide. The heterologous polypeptide can modify the ability of the Cas9 polypeptide to bind to and/or cleave a target nucleic acid by, e.g., inducing degradation of the Cas9 polypeptide. In some cases, the heterologous polypeptide includes an E3 ubiquitin ligase substrate, such as, but not limited to, an E3 ubiquitin ligase substrate from Cdt1 and Germinin.

In some embodiments, the heterologous polypeptide can provide for increased or decreased stability (i.e., the heterologous polypeptide is a stability control peptide, e.g., a degron, which in some cases is controllable (e.g., a temperature sensitive or drug controllable degron sequence). In some embodiments, the heterologous polypeptide can provide for increased or decreased transcription from the target nucleic acid (i.e., the heterologous polypeptide is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous polypeptide can provide a binding domain (i.e., the heterologous polypeptide is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.).

Suitable heterologous polypeptides that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the Cas9 fusion polypeptide with controllable stability such that the Cas9 fusion polypeptide can be turned "on" (i.e., stable) or "off" (i.e., unstable, degraded) depending on the desired conditions. For example, if the degron is a temperature sensitive degron, the Cas9 fusion polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Targeting Polypeptides

In some cases, a Cas9 fusion polypeptide of the present disclosure comprises a heterologous polypeptide that provides for targeting of the variant Cas9 polypeptide to a particular cell type, to a particular location within the body, to a particular location within a cell. The heterologous polypeptide may be any suitable polypeptide that can target the variant Cas9 to a location of interest. The target location of interest may be a target organ, such as the brain, heart, skin, retina, intestine, lung, kidney, adrenal gland, liver, bladder, spleen, thymus, prostate, testis, ovary, uterus, mammary or any other organ. The target location of interest may be a target tissue or cell type, such as blood vessel, muscle, epithelium, fat, cartilage, bone marrow, neuron, myocyte, chondrocyte, osteocyte, adipocyte, lymphocyte, or any other tissue or cell type. The target location of interest may be a target organelle or subcellular location, such as the nucleus, mitochondria, lysosome, endoplasmic reticulum, golgi, nucleolus, centrosome, endosome, plasma membrane, chloroplast, or any other organelle or subcellular location. The target location of interest may be healthy, or may be pathophysiological, such as cancerous, inflammatory, diabetic, ischemic, or have any other pathology.

In some cases, a targeting heterologous polypeptide includes a RGD-4C, NGR, or GSL peptide that target angiogenic vasculature of tumors. In some cases, a targeting heterologous polypeptide includes a polypeptide that targets bone marrow, prostate, placenta, adipose tissue, ovary, ureter or spleen, as described in U.S. Pat. No. 8,710,017, which is incorporated herein by reference. Other suitable targeting heterologous polypeptides are described in, e.g., Li et al., Methods Mol Biol. 2014, 1108:57; Kanki, et al., J Mol Cell Cardiol. 2011, 50:841; Veleva et al., Molecules. 2011, 16:900; and Rangel et al., Nat Commun. 2012, 3:788, which are incorporated by reference herein.

In some cases, a heterologous polypeptide provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a Cas9 fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases, the heterologous polypeptide includes a lipid-binding protein, or a suitable lipid binding domain thereof. The heterologous polypeptide may include any suitable lipid-binding domain, including, but not limited to, a pleckstrin homology (PH) domain, a protein kinase C (PKC) conserved 1 (C1-) and conserved 2 (C2-) domains.

In some cases, a Cas9 fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., a Cas9 fusion polypeptide). In some embodiments, a PTD is covalently linked to the carboxyl terminus of a polypeptide (e.g., a Cas9 fusion polypeptide). In some cases, the PTD is inserted interally in the Cas9 fusion polypeptide (i.e., is not at the N- or C-terminus of the Cas9 fusion polypeptide) at a suitable insertion site, as described herein. In some cases, a subject Cas9 fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a Cas9 fusion polypeptide includes one or more NLSs (e.g., 2 or more, 3 or more, 4 or more, or 5 or more NLSs). In some embodiments, a PTD is covalently linked to a nucleic acid (e.g., a Cas9 guide nucleic acid, a polynucleotide encoding a Cas9 guide nucleic acid, a polynucleotide encoding a Cas9 fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 1117); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 1118); Transportan GWTLNSAGYLLGKINLKALAALAKKIL (SEQ ID NO:1119); KALAWEAKLAKALAKALAKHLAKALAKALKCEA (SEQ ID NO:1120); and RQIKIWFQNRRMKWKK (SEQ ID NO:1121). Exemplary PTDs include but are not limited to, YGRKKRRQRRR (SEQ ID NO:1122), RKKRRQRRR (SEQ ID NO:1123); an arginine homopolymer of from 3 arginine residues to 50 arginine residues; Exemplary PTD domain amino acid sequences include, but are not limited to, any of the following: YGRKKRRQRRR (SEQ ID NO:1124); RKKRRQRR (SEQ ID NO:1125); YARAAARQARA (SEQ ID NO:1126); THRLPRRRRRR (SEQ ID NO:1127); and GGRRARRRRRR (SEQ ID NO:1128). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching poly-anion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Conjugation Sites

In some cases, a variant Cas9 polypeptide of the present disclosure comprises a heterologous polypeptide that provides a conjugation site for conjugation to a second moiety via bioorthogonal chemistry. The conjugation site may be a site for any suitable biorthogonal chemistry. Examples of bioorthogonal chemistries include, but are not limited to, [3±2]cycloadditions, Staudinger ligation, oxime ligation or hydrazone ligation (Dirksen et al., Biocong. Chem. 19:2543-2548 (2008)), inverse electron demand Diels-Alder (e.g., tetrazine ligation (Blackman et al., J. Am. Chem. Soc. 130:13518-13519 (2008)), and [2+2+2]cycloaddition (e.g., quadricyclane ligation (Sletten et al., J. Am. Chem. Soc. 133:17570-17573 (2011)).

In some embodiments, a Cas9 fusion polypeptide contains a heterologous polypeptide that provides a conjugation site for conjugation to a second moiety via a conjugation chemistry, where the Cas9 fusion polypeptide is modified to remove conjugation sites that are not in the heterologous polypeptide. In some cases, the conjugation site contains at least one sulfhydryl moiety (e.g., a cysteine residue) for reacting with a sulfhydryl-reactive chemical group (e.g., maleimide, haloacetyl, pyridyldisulfied, thiosulfonate, vinylsulfone, etc.) and the Cas9 fusion polypeptide does not contain a sulfhydryl moiety (e.g., a cysteine residue) outside of the heterologous polypeptide sequence. In some cases, the conjugation site contains a single sulfhydryl moiety for reacting with a sulfhydryl-reactive chemical group and the Cas9 fusion polypeptide does not contain a sulfhydryl moiety outside of the heterologous polypeptide sequence. Where the Cas9 fusion polypeptide does not contain a sulfhydryl moiety outside of the heterologous polypeptide sequence, such a Cas9 fusion polypeptide has been modified to remove naturally existing cysteines (e.g., a cysteine residue corresponding to C80 and/or C574 of the *S. pyogenes* Cas9 protein set forth in SEQ ID NO:5). For example, in some cases, naturally existing cysteines are removed and/or mutated (e.g., substituted to a serine residue, e.g., a substitution to serine of the cysteine residue corresponding to C80 and/or C574 of the *S. pyogenes* Cas9 protein set forth in SEQ ID NO:5, e.g., C80S and/or C574S).

In some cases, a Cas9 fusion polypeptide of the present disclosure comprises a heterologous polypeptide that provides an attachment site. In some cases, a Cas9 fusion polypeptide of the present disclosure comprises: a) a Cas9 polypeptide that has been modified such that it does not include any Cys residues (e.g., Cys residues found in a naturally-occurring Cas9 polypeptide; and b) an insertion of a single Cys residue at an insertion site as indicated above. In some cases, a Cas9 fusion polypeptide of the present disclosure comprises: a) a Cas9 polypeptide that has been modified such that it does not include any Cys residues (e.g., Cys residues found in a naturally-occurring Cas9 polypeptide; and b) an insertion of a single non-coded amino acid residue at an insertion site as indicated above. In some cases, a Cas9 fusion polypeptide of the present disclosure comprises: a) a Cas9 polypeptide that has been modified such that it does not include any Cys residues (e.g., Cys residues found in a naturally-occurring Cas9 polypeptide; and b) a heterologous polypeptide that comprises a single Cys residue inserted into the Cas9 polypeptide at an insertion site as indicated above, where the single Cys residue provides an attachment site for a second moiety. In some cases, a Cas9 fusion polypeptide of the present disclosure comprises: a) a Cas9 polypeptide; and b) a heterologous polypeptide that comprises a single non-coded amino acid residue inserted into the Cas9 polypeptide at an insertion site as indicated above, where the single non-coded amino acid residue provides an attachment site for a second moiety. Suitable non-coded amino acids include azide-modified amino acids, where the azide moiety provides an attachment site for modified phosphine-mediated, or strained cycloalkyne-mediated, etc., attachment of a second moiety.

The second moiety attached to the Cas9 fusion polypeptide can be a small molecule, a polypeptide, a lipid, a sugar, a polysaccharide, and the like. Small molecules (e.g., compounds having a molecular weight of less than 2000 daltons) can include therapeutic agents; cancer chemotherapeutic agents; cell targeting agents; DNA damaging agents; imaging agents; and the like.

Functional Polypeptides

In some cases, a Cas9 fusion polypeptide (e.g., a Cas9 polypeptide having a heterologous polypeptide that provides an activity) has enzymatic activity that modifies target nucleic acid (e.g., nuclease activity (which can be provided by the Cas9 sequences, but can alternatively be provided by exogenous amino acid sequences), methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity) and/or a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

In some embodiments, a Cas9 fusion polypeptide contains a heterologous polypeptide and can bind and/or modify a target nucleic acid (e.g., cleave, methylate, demethylate, etc.) and/or modify a polypeptide associated with target nucleic acid (e.g., methylation, acetylation, etc., of, for example, a histone tail) and/or modulate transcription of a target nucleic acid. In some cases, a Cas9 fusion polypeptide with a heterologous polypeptide has reduced nuclease activity (e.g., as described above) and contains a heterologous polypeptide that provides an activity that will be exhibited by the Cas9 fusion polypeptide (e.g., target cleavage, target methylation, transcription modulation, etc.).

In some such cases, a method of binding, e.g., in some cases where the Cas9 fusion polypeptide contains a heterologous polypeptide with an activity (e.g., an enzymatic activity) that modifies the target nucleic acid, the method can also be considered to be a method of modifying the target nucleic acid. In some cases, a method of binding a target nucleic acid (e.g., a single or double stranded target nucleic acid) can result in modification of the target nucleic acid. Thus, in some cases, a method of binding a target nucleic acid (e.g., a single or double stranded target nucleic acid) can be a method of modifying the target nucleic acid.

Suitable heterologous polypeptide include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable heterologous polypeptides include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable heterologous polypeptide (or fragments thereof) for a subject Cas9 fusion polypeptide include, but are not limited to those described in the PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

For example, suitable heterologous polypeptides include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable heterologous polypeptides include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable heterologous polypeptide include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of heterologous polypeptides to accomplish increased or decreased transcription include transcription activator and transcription repressor domains (e.g., the Kruppel associated box (KRAB or SKD); the Mad mSIN3 interaction domain (SID); the ERF repressor domain (ERD), etc.). In some such cases, a Cas9 fusion polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject Cas9 fusion polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR)

domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627.

Some RNA splicing factors that can be used (in whole or as fragments thereof) as heterologous polypeptides for a Cas9 fusion polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cώ-elements that are located in either the core exon region or the exon extension region (i.e., between the two alternative 5' splice sites). For more examples, see WO2010075303.

Linkers

In some embodiments, a subject Cas9 fusion polypeptide can include a Cas9 polypeptide that is linked to an internally inserted heterologous amino acid or heterologous polypeptide (a heterologous amino acid sequence) via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. In some cases, a linker peptide is stiff; for example, prolines can be used to generate a stiff linker. For example, a peptide that includes a poly(Pro) stretch can be used to generate a stiff linker. As another example, a peptide that includes Pro-Pro-Ser-Ala can be used as a linker. A variety of different linkers are commercially available and are considered suitable for use.

Exemplary linker polypeptides include glycine polymers $(G)_n$, glycine-serine polymers (including, for example, $(GS)_n$, $GSGGS_n$ (SEQ ID NO: 817), $GGSGGS_n$ (SEQ ID NO: 818), and $GGGS_n$ (SEQ ID NO: 819), where n is an integer of at least one), glycine-alanine polymers, alanine-serine polymers. Exemplary linkers can comprise amino acid sequences including, but not limited to, GGSG (SEQ ID NO: 820), GGSGG (SEQ ID NO: 821), GSGSG (SEQ ID NO: 822), GSGGG (SEQ ID NO: 823), GGGSG (SEQ ID NO: 824), GSSSG (SEQ ID NO: 825), and the like. The ordinarily skilled artisan will recognize that design of a peptide conjugated to any elements described above can include linkers that are all or partially flexible, such that the linker can include a flexible linker as well as one or more portions that confer less flexible structure.

Cas9 Guide RNA

A nucleic acid molecule that binds to a CRISPR/Cas protein (e.g., a Cas9 protein) and targets the complex to a specific location within a target nucleic acid is referred to herein as a "CRISPR/Cas guide nucleic acid" or "CRISPR/Cas guide RNA". When the guide RNA is for a Cas9 protein, e.g., a Cas9 fusion polypeptide, it is referred to as a "Cas9 guide RNA."

A Cas9 guide RNA can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein, e.g., a fusion Cas9 polypeptide, form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein, e.g., a fusion Cas9 polypeptide, to any desired sequence of any desired target nucleic acid, with the exception (e.g., as described herein) that the PAM sequence can be taken into account. Thus, for example, a Cas9 guide RNA can have a targeting segment with a sequence that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a subject Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 962-1075 (which are from crRNAs), or complements thereof, to form a dsRNA duplex of a protein binding segment.

Targeting Segment of a Cas9 Guide RNA

The first segment of a subject guide nucleic acid includes a guide sequence (i.e., a targeting sequence) (a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 guide RNAs can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10): 1163-71; Cho et al., Genetics. 2013 November; 195(3): 1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2): 333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Nucleic Acids

The present disclosure provides a nucleic acid comprising a nucleotide sequence encoding a fusion Cas9 polypeptide of the present disclosure. The present disclosure provides a nucleic acid/protein complex comprising: a) a fusion Cas9 polypeptide of the present disclosure; and b) a guide RNA.

The present disclosure provides compositions and methods that include a viral expression vector that includes, on the same DNA molecule: (i) a donor template sequence (having homology to a target locus of a target genome), and (ii) a nucleotide sequence that encodes a Cas9 guide RNA that hybridizes to a target sequence of the target locus of the targeted genome. Subject compositions and methods can also include a Cas9 fusion polypeptide of the present disclosure, or a nucleic acid encoding the Cas9 fusion polypeptide of the present disclosure (e.g., DNA or RNA, e.g., an mRNA). In some cases, the Cas9 fusion polypeptide is provided as a protein (e.g., not encoded by a nucleic acid). In some cases, the Cas9 fusion polypeptide is provided as an mRNA. In some cases, the Cas9 fusion polypeptide is provided as a DNA encoding the Cas9 fusion polypeptide, e.g., as part of a recombinant expression vector (e.g., a plasmid, a viral expression vector, e.g., a different viral expression vector than that which includes the donor template sequence and the Cas9 guide RNA).

In some embodiments, a subject method involves introducing into a cell (or a population of cells) (1) a viral expression vector that includes, on the same DNA molecule: (i) a donor template sequence (having homology to a target locus of a target genome), and (ii) a nucleotide sequence (operably linked to a promoter operable in a cell, e.g., a eukaryotic cell) that encodes a Cas9 guide RNA that hybridizes to a target sequence of the target locus of the targeted genome; and (2) a Cas9 fusion polypeptide of the present disclosure (or a nucleic acid comprising a nucleotide sequence encoding a Cas9 fusion polypeptide of the present disclosure). In some embodiments the targeted cell is in vitro and/or ex vivo. In some embodiments the targeted cell is in vivo.

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a Cas9 guide RNA is operably linked to a control element, e.g., a transcriptional control element, such as a promoter. In some embodiments, a nucleotide sequence encoding a Cas9 protein (e.g., a Cas9 fusion polypeptide comprising: a wild type Cas9 protein; a variant Cas9 protein, etc.) is operably linked to a control element, e.g., a transcriptional control element, such as a promoter.

The transcriptional control element can be functional in the targeted HSC (e.g., mobilized peripheral blood (mPB) CD34(+) cell, bone marrow (BM) CD34(+) cell, etc.)

Non-limiting examples of eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that can be fused to the Cas9 fusion protein, thus resulting in a chimeric polypeptide.

In some embodiments, a nucleotide sequence encoding a Cas9 guide RNA and/or a Cas9 fusion polypeptide is operably linked to an inducible promoter. In some embodiments, a nucleotide sequence encoding a Cas9 guide RNA and/or a Cas9 fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

Methods of introducing a nucleic acid into a host cell are known in the art, and any known method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

Introducing the viral expression vector into cells (along with a subject Cas9 fusion protein or nucleic acid encoding the protein) can occur in any culture media and under any culture conditions that promote the survival of the cells.

In some embodiments, a nucleotide sequence encoding a Cas9 protein, e.g. a subject Cas9 fusion polypeptide, can be codon optimized. In some cases, a codon optimized nucleotide sequence encoding a Cas9 fusion protein includes a sequence encoding a wildtype Cas9 protein or a variant Cas9 protein. Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target and/or host cell was a human cell, a subject Cas9 fusion protein, encoded by a human codon optimized nucleotide sequence would be a suitable Cas9 protein. As another non-limiting example, if the intended target and/or host cell was a mouse cell, a Cas9 protein encoded by a mouse codon optimized nucleotide sequence would be a suitable Cas9 protein. While codon optimization is not required, it is acceptable and may be preferable in certain cases.

In some embodiments, a Cas9 protein can be provided as RNA. The RNA can be provided by direct chemical synthesis or may be transcribed in vitro from a DNA (e.g., encoding the Cas9 protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): el 1756, and the commercially available TransMessenger® reagents from Qiagen, Stemfect™ RNA Transfection Kit from Stemgent, and TranslT®-mRNA Transfection Kit from Mirus Bio LLC. See also Beumer et al. (2008) Efficient gene targeting in *Drosophila* by direct embryo injection with zinc-finger nucleases. PNAS 105(50):19821-19826.

Vectors may be provided directly to the subject cells. In other words, the cells are contacted with vectors comprising the subject nucleic acids (e.g., viral expression vectors having the donor template sequence and encoding the Cas9 guide RNA; encoding the Cas9 protein) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding Cas9 guide RNA and/or a Cas9 fusion protein to HSCs can include suitable promoters for driving the expression, that is, transcriptional activation, of the nucleic acid of interest. In other words, the nucleic acid of interest will be operably linked to a promoter. This may include ubiquitously acting promoters, for example, the CMV-O-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a Cas9 guide RNA and/or a Cas9 protein to the subject cells may include nucleic acid sequences that encode for selectable markers in the target cells, so as to identify cells that have taken up the Cas9 guide RNA and/or Cas9 protein.

A Cas9 fusion protein can be introduced into cells as RNA. Methods of introducing RNA into cells are known in the art and may include, for example, direct injection, transfection, or any other method used for the introduction of DNA. A Cas9 fusion protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the Cas9 fusion polypeptide may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 826). As another example, the permeant peptide comprises the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 November 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A Cas9 fusion polypeptide of the present disclosure may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a Cas9 guide RNA, encoding a Cas9 fusion protein, etc.) and proteins (e.g., a Cas9 fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

A Cas9 fusion polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A Cas9 fusion polypeptide of the present disclosure may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein.

To induce cleavage or any desired modification to a target nucleic acid (e.g., genomic DNA), or any desired modification to a polypeptide associated with target nucleic acid, the Cas9 guide RNA and/or the Cas9 fusion polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different Cas9 guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Introducing Components into a Target Cell

A Cas9 guide RNA (or a nucleic acid comprising a nucleotide sequence encoding same and/or a Cas9 fusion polypeptide of the present disclosure (or a nucleic acid that includes a nucleotide sequence encoding a Cas9 fusion polypeptide of the present disclosure) can be introduced into a host cell by any of a variety of well-known methods.

Methods of introducing a nucleic acid into a host cell are known in the art, and any known method can be used to introduce a nucleic acid (e.g., an expression construct) into a target cell. Suitable methods include, include e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a Cas9 fusion polypeptide of the present disclosure is provided as a nucleic acid (e.g., an mRNA, a DNA, a plasmid, an expression vector, a viral vector, etc.) that encodes the Cas9 fusion polypeptide. In some cases, the Cas9 fusion polypeptide of the present disclosure is provided directly as a protein. A Cas9 fusion polypeptide of the present disclosure can be introduced into a cell (provided to the cell) by any convenient method; such methods are known to those of ordinary skill in the art. As an illustrative example, a Cas9 fusion polypeptide of the present disclosure can be injected directly into a cell (e.g., with or without nucleic acid encoding a Cas9 guide RNA and with or without a donor polynucleotide). As another example, a preformed complex of a Cas9 fusion polypeptide of the present disclosure and a Cas9 guide RNA (an RNP) can be introduced into a cell (e.g., via nucleofection; via a protein transduction domain (PTD) conjugated to one or more components, e.g., conjugated to the Cas9 protein, conjugated to a guide RNA, conjugated to a Cas9 fusion polypeptide of the present disclosure and a guide RNA; etc.).

Host Cells

The present disclosure provides host cells comprising (e.g., genetically modified to comprise) a nucleic acid of the present disclosure. The present disclosure provides host cells comprising (e.g., modified to comprise, e.g., genetically modified to comprise) a recombinant vector of the present disclosure. The modified host cells are in some cases in vitro host cells. In some cases, the modified host cells are in vivo host cells.

Suitable host cells include, e.g. a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like.

A suitable host cell can be a stem cell (e.g. an embryonic stem (ES) cell, an induced pluripotent stem (iPS) cell); a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be maintained for fewer than 10 passages in vitro. Host cells are in many embodiments unicellular organisms, or are grown in culture.

If the cells are primary cells, they may be harvest from an organism (e.g., an individual) by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells can be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell or is derived from a rodent cell. In some embodiments, a subject genetically modified host cell is a human cell or is derived from a human cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

Donor Polynucleotide (Donor Template)

In some cases, the contacting occurs under conditions that are permissive for nonhomologous end joining or homology-directed repair. In some cases, the method further comprises contacting the target DNA with a donor polynucleotide, wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, Cas9 guide RNA and a Cas9 fusion polypeptide are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, a complex comprising a Cas9 guide RNA and a Cas9 fusion polypeptide is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the cleavage site induced by a Cas9 fusion polypeptide. The donor polynucleotide will contain sufficient homology to a genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described above for nucleic acids encoding a Cas9 guide RNA and/or a Cas9 fusion polypeptide and/or donor polynucleotide.

Non-Human Genetically Modified Organisms

In some embodiments, a genetically modified host cell has been genetically modified with an exogenous nucleic acid comprising a nucleotide sequence encoding a subject Cas9 fusion polypeptide (e.g., a Cas9 fusion polypeptide of the present disclosure comprising wild-type (WT) Cas9 sequences; a Cas9 fusion polypeptide of the present disclosure comprising a variant Cas9 polypeptide, having one or more mutations relative to a WT Cas9, such as a Cas9 with reduced nuclease activity). If such a cell is a eukaryotic single-cell organism, then the modified cell can be considered a genetically modified organism. In some embodiments, subject non-human genetically modified organism is a Cas9 transgenic multicellular organism.

In some embodiments, a subject genetically modified non-human host cell (e.g., a cell that has been genetically modified with an exogenous nucleic acid comprising a nucleotide sequence encoding a subject Cas9 fusion polypeptide can generate a subject genetically modified non-human organism (e.g., a mouse, a fish, a frog, a fly, a worm, etc.). For example, if the genetically modified host cell is a pluripotent stem cell (i.e., PSC) or a germ cell (e.g., sperm, oocyte, etc.), an entire genetically modified organism can be derived from the genetically modified host cell. In some embodiments, the genetically modified host cell is a pluripotent stem cell (e.g., ESC, iPSC, pluripotent plant stem cell, etc.) or a germ cell (e.g., sperm cell, oocyte, etc.), either in vivo or in vitro, that can give rise to a genetically modified organism. In some embodiments the genetically modified host cell is a vertebrate PSC (e.g., ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism is suitable for producing a genetically modified host cell comprising an exogenous nucleic acid comprising a nucleotide sequence encoding a subject Cas9 fusion polypeptide. Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; Husaini et al., GM Crops. 2011 June-December; 2(3):150-62. Epub 2011 Jun. 1: Approaches for gene targeting and targeted gene expression in plants.

In some embodiments, a genetically modified organism comprises a target cell for methods of the invention, and thus can be considered a source for target cells. For example, if a genetically modified cell comprising one or more exogenous nucleic acids comprising nucleotide sequences encoding a subject Cas9 fusion polypeptide is used to generate a genetically modified organism, then the cells of the genetically modified organism comprise the one or more exogenous nucleic acids comprising nucleotide sequences encoding the subject Cas9 fusion polypeptide. In some such embodiments, the DNA of a cell or cells of the genetically modified organism can be targeted for modification by introducing into the cell or cells a Cas9 guide RNA (e.g., a truncated Cas9 guide RNA) (or a nucleic acid encoding the Cas9 guide RNA) and in some cases a ligand for a heterologous polypeptide inserted in the Cas9 fusion polypeptide and that binds and/or undergoes a conformational change upon contacting the ligand (e.g., to induce binding to a binding partner of the heterologous polypeptide, to induce a conformational change of the Cas9 fusion polypeptide, etc.) (e.g., and/or in some cases a donor polynucleotide). For example, the introduction of a Cas9 guide RNA (or a DNA encoding the same) into a subset of cells (e.g., brain cells, intestinal cells, kidney cells, lung cells, blood cells, etc.) of the genetically modified organism can target the DNA of such cells for modification, the genomic location of which will depend on the targeting sequence of the introduced Cas9 guide RNA.

In some embodiments, a genetically modified organism is a source of target cells for methods of the invention. For example, a genetically modified organism comprising cells that are genetically modified with an exogenous nucleic acid comprising a nucleotide sequence encoding a subject Cas9 fusion polypeptide can provide a source of genetically modified cells, for example PSCs (e.g., ESCs, iPSCs, sperm, oocytes, etc.), neurons, progenitor cells, cardiomyocytes, etc.

In some embodiments, a genetically modified cell is a PSC comprising an exogenous nucleic acid comprising a nucleotide sequence encoding a subject Cas9 fusion polypeptide. As such, the PSC can be a target cell such that the DNA of the PSC can be targeted for modification by introducing into the PSC a Cas9 guide RNA (e.g., a truncated Cas9 guide RNA) (or a nucleic acid encoding the Cas9 guide RNA) and in some cases a ligand for a heterologous polypeptide inserted in the Cas9 fusion polypeptide and that binds and/or undergoes a conformational change upon contacting the ligand (e.g., light, a dimerizing agent, etc.), and optionally a donor nucleic acid (donor polynucleotide), and the genomic location of the modification will depend on the targeting sequence of the introduced Cas9 guide RNA. Thus, in some embodiments, the methods described herein can be used to modify the DNA (e.g., delete and/or replace any desired genomic location) of PSCs derived from a subject genetically modified organism. Such modified PSCs can then be used to generate organisms having both (i) an exogenous nucleic acid comprising a nucleotide sequence encoding a subject Cas9 fusion polypeptide and (ii) a DNA modification that was introduced into the PSC.

An exogenous nucleic acid comprising a nucleotide sequence encoding a subject Cas9 fusion polypeptide (e.g., comprising: wild-type (WT) Cas9 sequences; a variant Cas9, having mutations relative to a WT Cas9, such as a Cas9 with reduced nuclease activity, etc.) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

A subject genetically modified non-human organism can be any organism other than a human, including for example, a plant; algae; an invertebrate (e.g., a cnidarian, an echinoderm, a worm, a fly, etc.); a vertebrate (e.g., a fish (e.g., zebrafish, puffer fish, gold fish, etc.), an amphibian (e.g., salamander, frog, etc.), a reptile, a bird, a mammal, etc.); an ungulate (e.g., a goat, a pig, a sheep, a cow, etc.); a rodent (e.g., a mouse, a rat, a hamster, a guinea pig); a lagomorpha (e.g., a rabbit); etc.

Transgenic Non-Human Animals

As described above, in some embodiments, a subject nucleic acid (e.g., one or more nucleic acids comprising nucleotide sequences encoding a subject Cas9 fusion polypeptide, e.g., a Cas9 fusion polypeptide comprising: WT Cas9 sequences; a variant Cas9, having mutations relative to a WT Cas9, such as a Cas9 with reduced nuclease activity, etc.; and the like), e.g., a recombinant expression vector, is used as a transgene to generate a transgenic animal that produces a Cas9 fusion polypeptide. Thus, the present disclosure further provides a transgenic non-human animal, which animal comprises a transgene comprising a subject nucleic acid comprising a nucleotide sequence encoding a Cas9 fusion polypeptide (e.g., one ore more nucleic acids comprising nucleotide sequences encoding a Cas9 fusion polypeptide). In some embodiments, the genome of the transgenic non-human animal comprises a subject nucleotide sequence encoding a Cas9 fusion polypeptide. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g., zebra fish, gold fish, puffer fish, cave fish, etc.), an amphibian (frog, salamander, etc.), a bird (e.g., chicken, turkey, etc.), a reptile (e.g., snake, lizard, etc.), a mammal (e.g., an ungulate, e.g., a pig, a cow, a goat, a sheep, etc.; a lagomorph (e.g., a rabbit); a rodent (e.g., a rat, a mouse); a non-human primate; etc.), etc.

Nucleotide sequences encoding a Cas9 fusion polypeptide (e.g., one or more nucleic acids comprising nucleotide sequences encoding a Cas9 fusion polypeptide) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some embodiments, a subject nucleic acid (e.g., one or more nucleic acids comprising nucleotide sequences encoding a subject Cas9 fusion polypeptide, e.g., a Cas9 fusion polypeptide comprising: WT Cas9 sequences; a variant Cas9, having mutations relative to a WT Cas9, such as a Cas9 with reduced nuclease activity; and the like), e.g., a recombinant expression vector, is used as a transgene to generate a transgenic plant that produces a Cas9 fusion polypeptide. Thus, the present disclosure further provides a transgenic plant, which plant comprises a transgene comprising a subject nucleic acid comprising a nucleotide sequence encoding a Cas9 fusion polypeptide (e.g., one or more nucleic acids comprising nucleotide sequences encoding a Cas9 fusion polypeptide). In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A subject nucleic acid may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545, 817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

Also provided by the subject disclosure are transformed plant cells, tissues, plants and products that contain the transformed plant cells. A feature of the subject transformed cells, and tissues and products that include the same is the presence of a subject nucleic acid integrated into the genome, and production by plant cells of a fusion Cas9 polypeptide. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a fusion Cas9 polypeptide can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Methods

A Cas9 fusion polypeptide of the present disclosure finds use in a variety of methods. A subject Cas9 fusion polypeptide can be used in any method that a Cas9 protein can be used. For example, a Cas9 fusion polypeptide, or a variant thereof, can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Because a method that uses a Cas9 fusion polypeptide includes binding of the fusion polypeptide to a particular region in a target nucleic acid (by virtue of being targeted there by an associated Cas9 guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid, modulation of translation of the target nucleic acid, genome editing, modulation of a protein associated with the target nucleic acid, isolation of the target nucleic acid, etc.). For examples of suitable methods, Cas9 variants, guide RNAs, etc., see, for example, Jinek et al., Science. 2012 Aug. 17; 337(6096): 816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; *Mali* et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853;

20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a Cas9 fusion polypeptide, etc., encompass all methods for contacting the target nucleic acid. For example, a Cas9 fusion polypeptide can be provided as protein, RNA (encoding the Cas9 fusion polypeptide), or DNA (encoding the Cas9 fusion polypeptide); while a Cas9 guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for Cas9 fusion polypeptide, in the form of an RNA in some cases for the guide RNA), and also encompasses the introduction into the cell of one or more nucleic acids encoding one or more of the components (e.g., nucleic acid(s) having nucleotide sequence(s) encoding Cas9 fusion polypeptide protein(s), nucleic acid(s) having nucleotide sequence(s) encoding guide RNA(s), and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a subject method is a method that includes contacting a target nucleic acid with a subject Cas9 fusion polypeptide. In some cases, a subject method includes contacting a target nucleic acid with a Cas9 fusion polypeptide and a Cas9 guide RNA (e.g., a truncated Cas9 guide RNA, e.g., not having stem loops 2 or 3). In some cases, a subject method includes contacting a target nucleic acid with a Cas9 fusion polypeptide and a Cas9 guide RNA (e.g., a truncated guide RNA, e.g., not having stem loops 2 or 3) and a ligand for a heterologous polypeptide inserted in the Cas9 fusion polypeptide and that binds and/or undergoes a conformational change upon contacting the ligand (e.g., light, a dimerizing agent, etc.). In some cases, a method is a method of contacting a target nucleic acid with a system. In some cases, the system can include: (i) a subject Cas9 fusion polypeptide and a Cas9 guide RNA; (ii) a subject Cas9 fusion polypeptide and a Cas9 guide RNA and a ligand for a heterologous polypeptide; or (iii) a subject Cas9 fusion polypeptide and a Cas9 guide RNA and a ligand for a heterologous polypeptide and a donor polynucleotide.

Thus, in some cases, where the Cas9 fusion polypeptide includes a heterologous polypeptide that conditionally binds to a binding partner and confers inducible activity to the Cas9 fusion polypeptide, the subject method includes contacting the Cas9 fusion polypeptide to a condition that induces activity of the Cas9 fusion polypeptide, thereby contacting a target nucleic acid to the active Cas9 fusion polypeptide. In some cases, the condition that induces activity of the Cas9 fusion polypeptide includes contacting the Cas9 fusion polypeptide with a ligand (or an increasing or reducing the amount of a ligand) that binds to and/or induces a conformational change in the heterologous polypeptide inserted in the Cas9 fusion polypeptide. The ligand may be any suitable ligand that binds to and/or induces a conformational change in the heterologous polypeptide. In some cases, the ligand is a small molecule (e.g., rapamycin, 4-hydroxytamoxifen (4-HT), etc.), light, a receptor ligand (e.g., 4-hydroxytamoxifen (4-HT)), a metabolite (e.g., cAMP; lactate; etc.), an ion ($Ca^{2+}$, $Zn^{2+}$, $Cu^{2+}$, $Na^{+}$, Cl, K, etc.), etc. In some cases, the condition is a cellular signaling event that causes post-translational modification of the heterologous polypeptide (e.g., activating a kinase cascade to phosphorylate a kinase substrate in the heterologous polypeptide; depolarizing an excitable cell to increase intracellular calcium concentration and activate a Cas9 fusion polypeptide that contains a heterologous polypeptide with a calcium binding domain, etc.) In some cases, the conditions necessary to modulate activity of a subject Cas9 fusion polypeptide may be provided indirectly to the cell or tissue in which the Cas9 fusion polypeptide resides, e.g., by administering a drug to an organism that activates a kinase cascade in a cell of interest, which in turn phosphorylates a kinase substrate in the heterologous polypeptide; providing a sensory stimulation to an organism that activates a neural circuit, that in turn depolarizes a neuron of interest to increase intracellular calcium concentration and activate a Cas9 fusion polypeptide that contains a heterologous polypeptide with a calcium binding domain, etc.

Target Nucleic Acids and Target Cells of Interest

A Cas9 fusion polypeptide of the present disclosure, when bound to a guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome, derived from a chromosome, chromosomal, plasmid, viral, extracellular, intracellular, mitochondrial, chloroplast, linear, circular, etc.) and can be from any organism (e.g., as long as the Cas9 guide RNA can hybridize to a target sequence in a target nucleic acid, that target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Introducing Components into a Target Cell

A Cas9 guide RNA (or a nucleic acid comprising a nucleotide sequence encoding same), and/or a Cas9 fusion polypeptide (or a nucleic acid comprising a nucleotide sequence encoding same) and/or a donor polynucleotide can be introduced into a host cell by any of a variety of well-known methods.

Methods of introducing a nucleic acid into a host cell are known in the art, and any known method can be used to introduce a nucleic acid (e.g., an expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. Any or all of the components can be introduced into a cell as a composition (e.g., including any convenient combination of: a Cas9 fusion polypeptide, a Cas9 guide RNA, a dimerizing agent, a donor polynucleotide, etc.) using known methods, e.g., such as nucleofection.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Materials and Methods

The following materials and methods were used throughout the Examples.

Strains and Media

*Escherichia coli* MG1655, which have chromosomally integrated constitutive GFP and RFP expression, were used for in vivo screening, fluorescence measurements, and transformation assays. Cell transformation, plasmid maintenance, and verification of transformation were done as previously described using AmpR and CmR as selectable markers. EZ-rich defined growth medium (EZ-RDM, Teknoka) was used for in vivo fluorescence assays unless otherwise noted. Super optimal broth (S.O.B) medium was used for library outgrowth and screening. The arC9 ligands used (4-hydroxytamoxifen (4-HT), nafoxidine, beta-estradiol, and diethylstilbestrol) were all ordered from Sigma and resuspended in dimethyl sulfoxide (DMSO).

Transposon Library Construction

A modified transposon containing an antibiotic resistance marker (S1) was inserted into pUC19 plasmid carrying dCas9 in an in vitro reaction. The coding sequence of dCas9 was subsequently excised via restriction digest, size-selected for successful transposon insertion, and cloned, using standard molecular biology procedures, into the expression plasmid pdCas9-bacteria (Addgene ID: 44249). A golden gate reaction was then used to remove the modified transposon and insert the domain of interest (PDZ, ER) in its place. No selection was used for this cloning step, but efficiencies of reaction were >99%. Completed libraries were transformed into *E. coli* using electroporation.

Library Sequencing and Analysis

The open reading frame (ORF) coding for the Cas9 insertion constructs were excised from plasmids via restriction digestion and then sheared to ~300 bp fragments for sequencing. All libraries were prepped with a NEBnext® DNA Library Prep Kit (New England Biolabs) and sequenced on Illumina platform sequencers (MySeq® and HiSeq®). Sequencing data was analyzed with a custom Python pipeline that is available online at http(colon)//github(dot)com/SavageLab/dipseq. In brief, reads were filtered to remove those that did not contain both Cas9 and sequence from the inserted domain (PDZ or estrogen receptor (ER)-ligand binding domain (LBD)). The inserted domain was then trimmed from the read and the remaining sequence was aligned to dCas9 to calculate the insertion site in nucleotides from the start codon. Linker sequences were extracted from the original sequence. The insertion site, linker length, and insert sequence were then used to calculate whether the insertion was in-frame and forward-oriented relative to dCas9. For such productive insertions, the amino acid (AA) insertion site was calculated as the carboxyl (C)-terminal most amino acid after which the amino (N)-terminus of the insert was detected. In this manner, it was ensured that reads catching the N- or C-terminal end of the insertion would result in the same calculated insertion site. This scheme was tested for correctness and recall by processing one million synthetic reads for each library. Each library was sequenced twice and reads identifying N- and C-terminal insertions for the same site were used as internal technical replicates, giving four technical replicates with which to calculate fold changes and associated p-values. Fold changes were calculated using the DESeq package, which uses a negative binomial model so as not to underestimate the dispersion of read counts at each site. All p-values reported were corrected for multiple hypothesis testing using the Benjamini-Hochberg procedure implemented by DESeq.

Clustered Regularly Interspaced Short Palindromic Repeats Interference (CRISPRi) Screen and Fluorescence-Activated Cell Sorting Selection Screening of the PDZ libraries was accomplished by transforming and screening at least >10 fold more *E. coli* than the theoretical library size and repeating two rounds of positive screening and fluorescence-activated cell sorting (FACS) selection. Screening for the ER library followed these same methods however the primary screen and FACS selection was for function with 4-HT, the secondary screen and FACS selection was against function without 4-HT, and the final screen was for function with 4-HT on plates. From these plates colonies were picked by eye (FIG. 7) for dCas9 based repression of RFP and tested in triplicate for RFP based repression after overnight growth in 2 μM anhydrotetracycline (aTc) and with and without 10 μM 4-HT in SOB media.

Figure 7A:
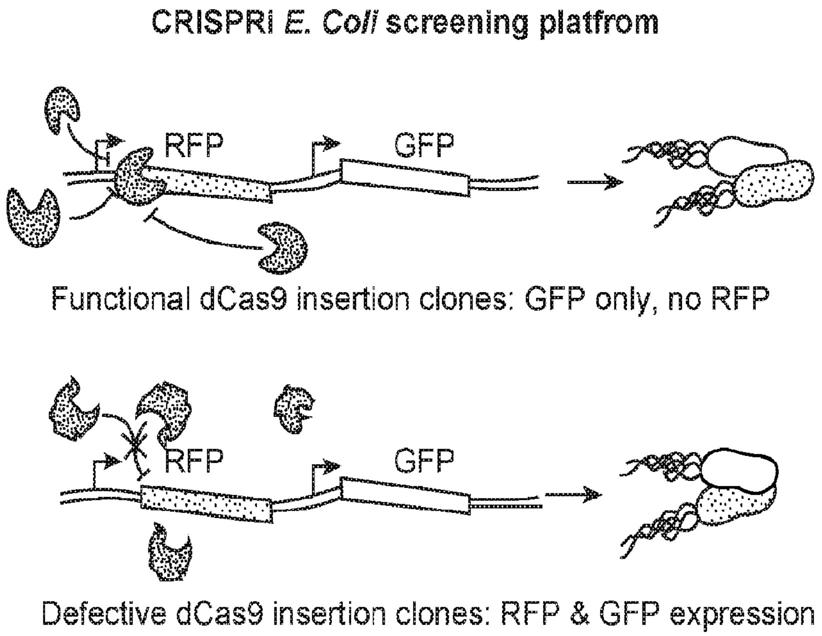
FIG. 7A-7C are a collection of images and figures showing controls for the clustered regularly interspaced short palindromic repeats interference (CRISPRi) screening protocol.
Figure 7B:
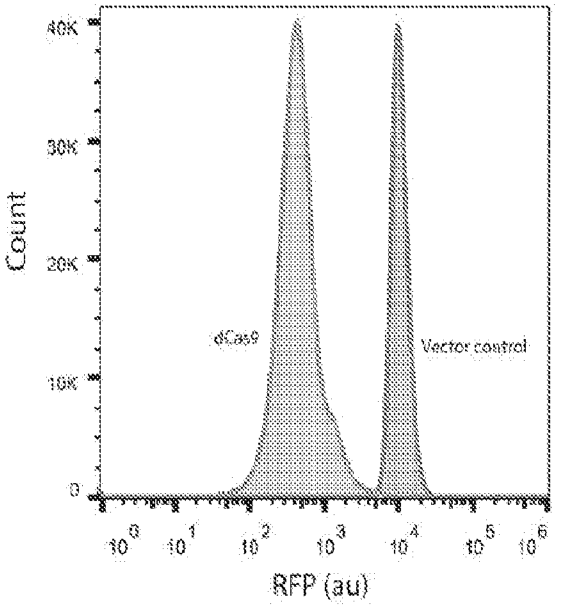
Figure 7C:
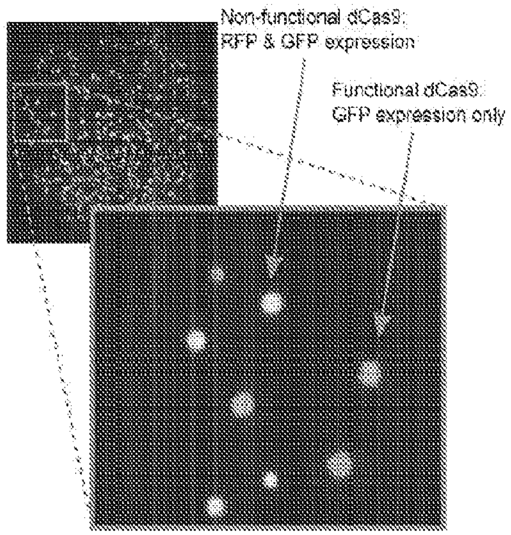

FIG. 7A-7C. CRISPRi screening protocol controls (FIG. 7A) Schematic of the *E. coli* screening platform for determining DNA-binding competent dCas9 insertion mutants. (FIG. 7B) Flow cytometry of the red fluorescent protein (RFP) repression by dCas9. A 20 fold change in RFP fluorescence when dCas9 was present for 6+ hours, similar to previously reported results reported. This provided a clear signal by which to select functional Cas9 insertion mutants (FIG. 7C) On-plate screening of RFP repression by dCas9. The lack of RFP signal was visible by eye when screening colonies after overnight growth on plates.

CRISPRi Green Fluorescent Protein (GFP) Repression Assays

For individual PDZ-construct testing, colonies were cultured from plates, PDZ-dCas9 plasmid DNA recovered, separated from the RFP guide plasmid (pgRNA-bacteria Addgene ID: 44251) via restriction digestion with BsaI and co-transformed with a guide plasmid to repress chromosomal GFP. GFP repression for each construct was then tested in triplicate in a 96-well microplate reader (Tecan M1000) at 37° C. PDZ clones were grown with appropriate antibiotics, 0.2 nM aTc, dCas9, and inducer. $OD_{600\ nm}$ absorbance was measured for each well. GFP signal was measured, normalized for $OD_{600\ nm}$ and compared when the cultures were approaching saturation (80% of the maximum $OD_{600\ nm}$) The arC9 construct was treated and assayed in the same fashion as above with induction using 2 M aTc. Fold changes for the effect of different ligands were calculated by normalizing the GFP/$OD_{600}$ of the arC9 construct to that of a vector control and dividing the fluorescent values without ligand by the fluorescent values with ligand treatment. For single cell analysis of arC9, cells were grown for ~6 hours with antibiotics and inducer, washed with PBS, and assayed for GFP fluorescence using a Sony SH800 cell sorter.

Transformation Assay

*E. coli* containing a sgRNA plasmid which targets the genome (either the chromosomal RFP or GFP) were made electrocompetent as described previously 10 and similar to previous work all tests were done with the same batch of electrocompetent cells to minimize transformation variability. *E. coli* with these self-targeting guides were electroporated with 9 fmol of either wtCas9, dCas9 plasmid, or a test construct plasmid (active PDZ-Cas9s, or arC9) in triplicate using a BTX Harvard Apparatus ECM 630 High Throughput Electroporation System. Cells were recovered in 1 mL SOB with catabolite repression (S.O.C.) medium post-electroporation for 1 hr. Colony forming unit (CFU)/mL was calculated by spotting 2 technical replicates of 10-fold serial dilutions onto plates containing antibiotics for both plasmids.

Human Embryonic Kidney (HEK) 293T-Enhanced GFP (EGFP)-PEST Cell Line Creation

The d2EGFP reporter construct was created in a modified lentivirus backbone with EF1-a promoter driving the gene of interest and a second PGK promoter driving production of a gene which confers resistance to hygromycin. The EGFP is destabilized by fusion to residues 422-461 of mouse ornithine decarboxylase, giving an in vivo half-life of ~2 hours. Transduced 293T cells were selected with hygromycin (250 μg/ml). d2EGFP clones were isolated by sorting single cells into 96-well plates and characterized by intensity of d2EGFP. Lentivirus was produced by polyethylenimine (PEI) (Polysciences Inc., 24765) transfection of 293T cells with gene delivery vector co-transfected with packaging vectors pspax2 and pMD2.G essentially as described previously.

HEK 293T GFP Disruption Assay

GFP disruption assays were based on those previously described. Briefly, HEK cells were cultured in 10 cm dishes using Dulbecco's Modification of Eagle's Medium (DMEM) with 4.5 g/L glucose, L-glutamine, sodium pyruvate (Corning Cellgro®) plus 10% fetal bovine serum, 1×MEM Non-Essential Amino Acids Solution (Gibco®) and Pen-Strep (Gibco®). One day before transfection, ~3×10^4 cells were plated into each well of a 96-well plate with the DMEM medium plus hygromycin and allowed to settle. One hour before transfection the media was removed and replaced with media with ligand treatment or vehicle control. Cells were transfected with Lipofectamine® 2000 (Life Technologies) and plasmid DNA (FIGS. 13A and 13B) according to manufacturer's protocol. Cells were analyzed for EGFP and mCherry® expression at 48 or 72 hours post transfection using a BD LSR Fortessa® high-throughput sequencer. Transfected cells were gated positive based on mCherry® fluorescence and the percent EGFP disruption for three independent biological replicates was calculated from this gate (FIGS. 14A-14C).

Figure 13A:
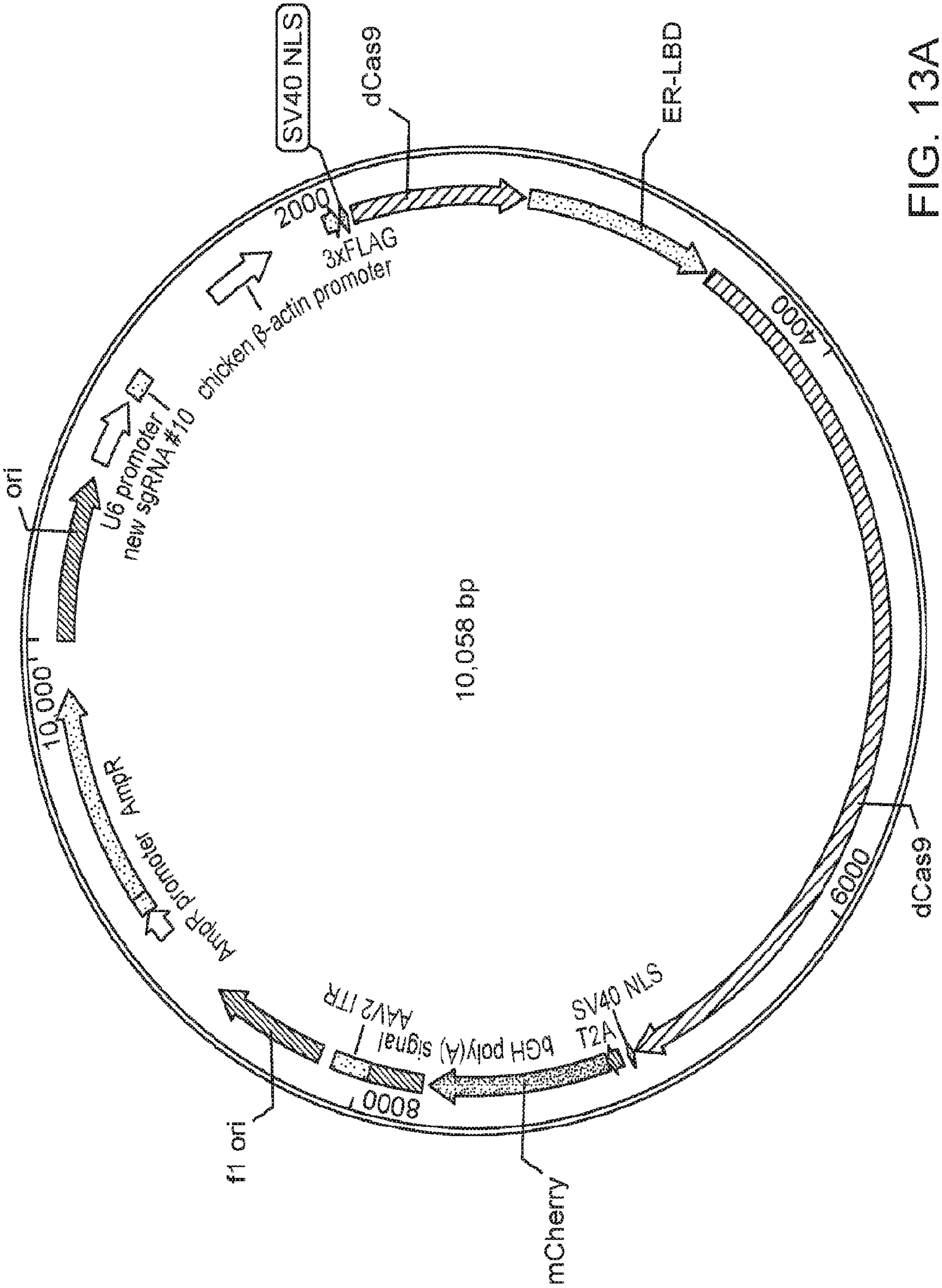
FIGS. 13A and 13B are schematic diagrams showing arC9 human plasmids.
Figure 13B:

FIG. 13A-13B. ArC9 Human Plasmid. (FIG. 13A) Schematic description of the human arC9 expression plasmid with the 2× nuclear localization signal (NLS), T2A cleavable linker and mCherry®. Plasmid is originally derived from a pX330 variant. (FIG. 13B) Schematic of the human arC9 expression plasmid without NLS.

Figure 14A:
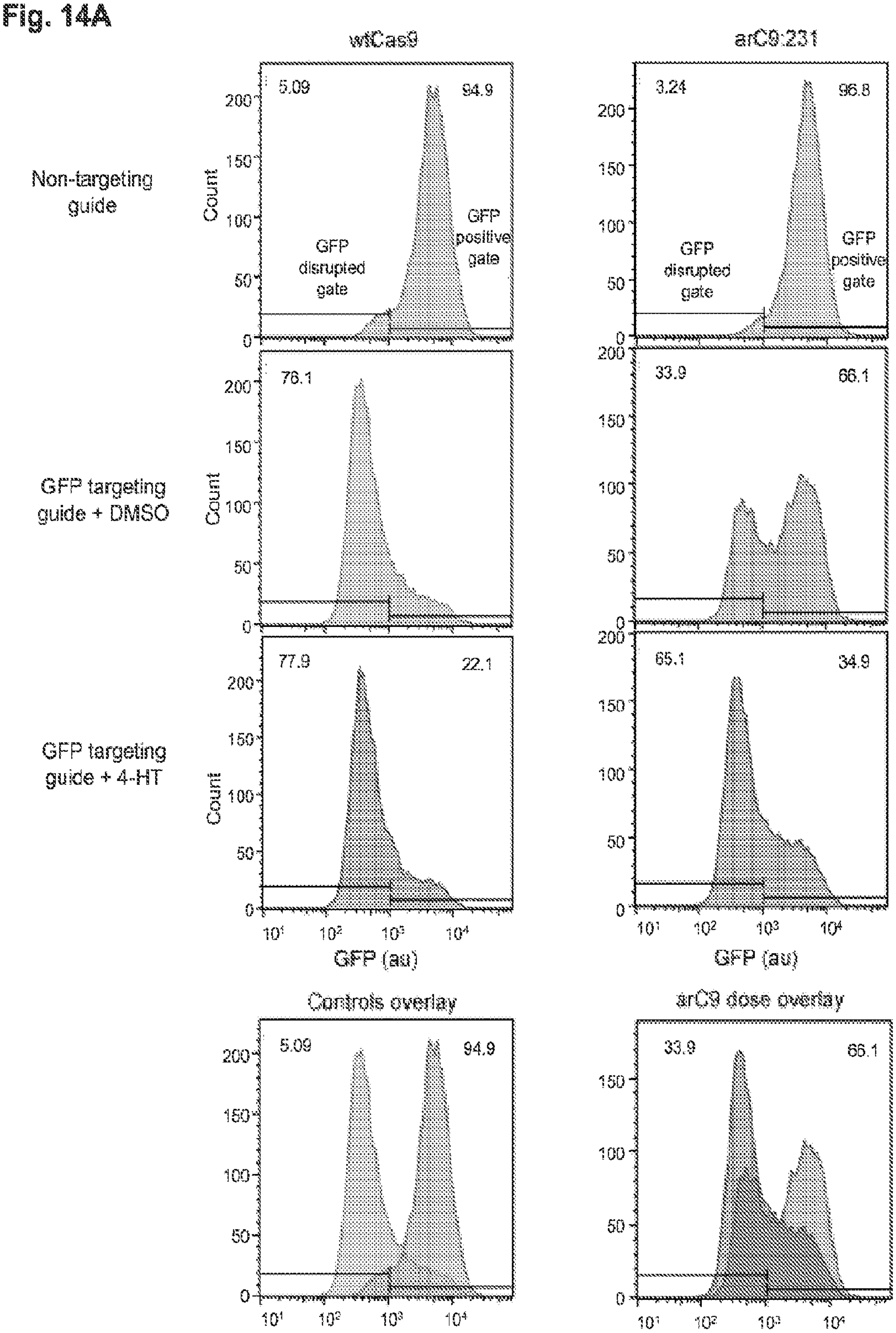
FIG. 14A-14C are a collection of figures showing arC9 expression levels in human embryonic kidney (HEK) 293T cells, according to embodiments of the present disclosure.
Figure 14B:
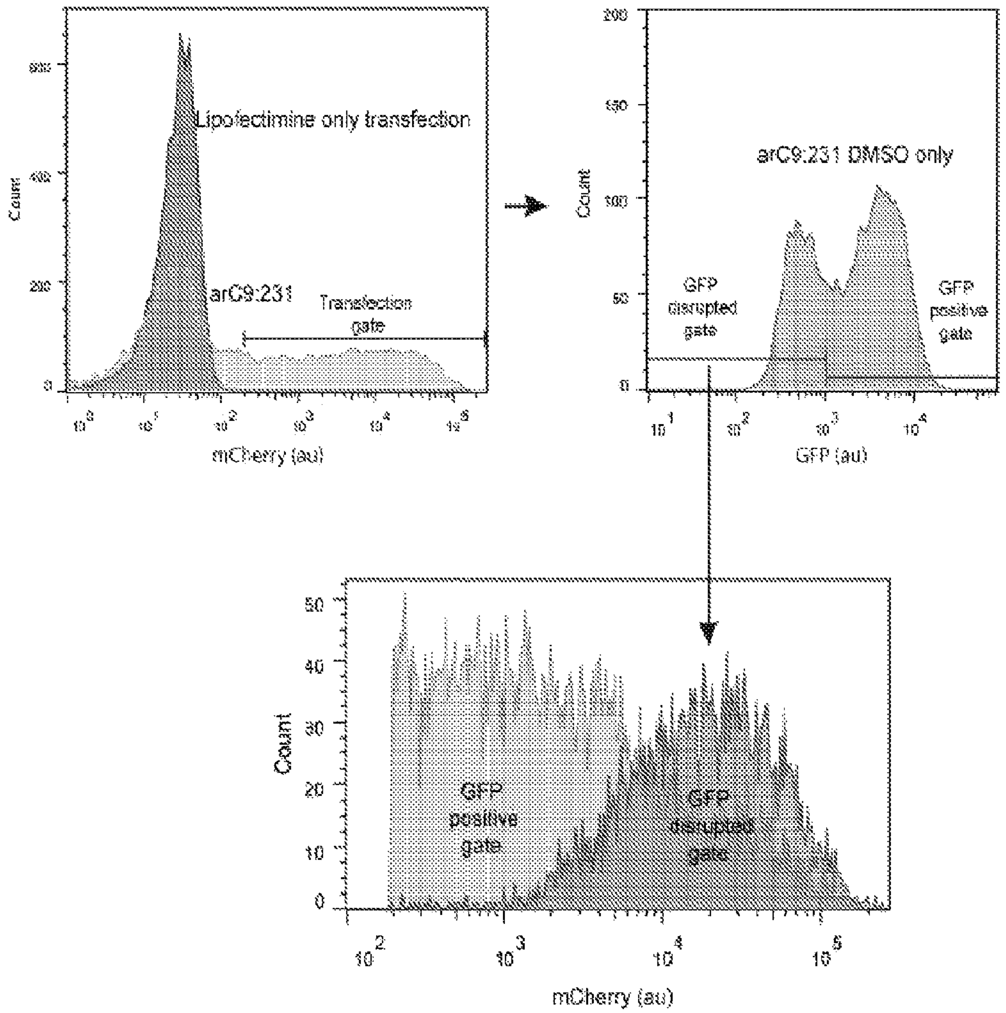
Figure 14C:
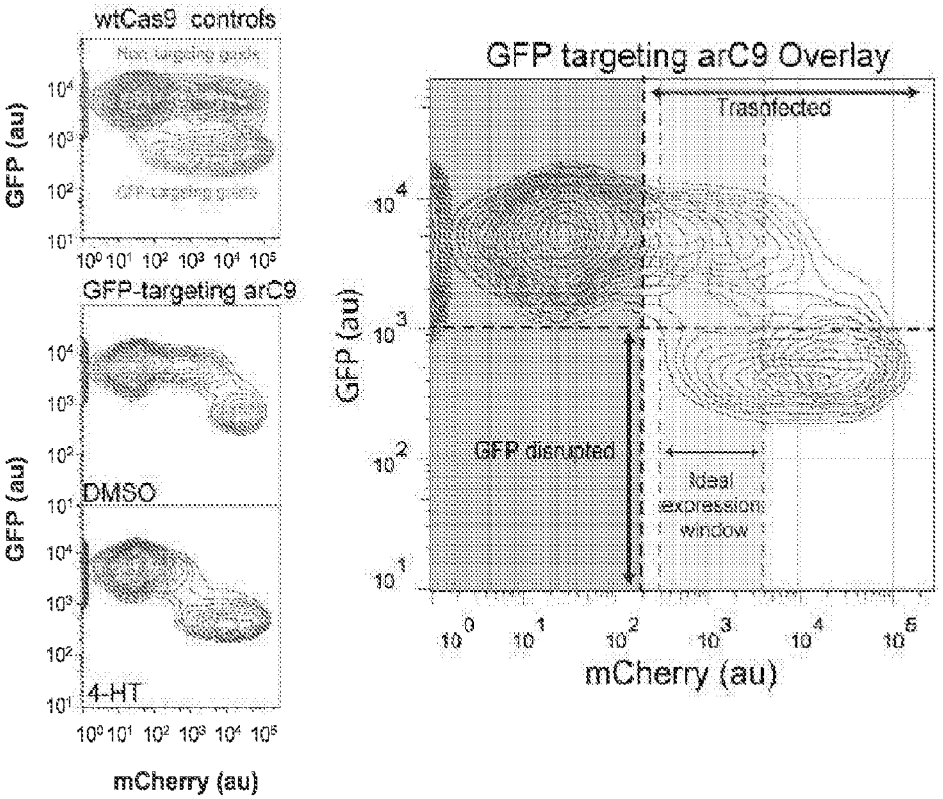

FIG. 14A-14C. HEK 293T transfection optimization for arC9 expression levels. (FIG. 14A) Upon transfection of 75 ng of plasmid into the HEK293T cell line and measurement EGFP fluorescence via Flow cytometry at 48 hours it was observed that 2×NLS-Cas9 disrupted ~70-80% of EGFP signal regardless of treatment condition. 2×NLS-arC9 also disrupted GFP signal but with only a 2 fold increase upon the addition of 4-HT (FIG. 14B). 4-HT-induced activation was seen at low levels of arC9-mCherry® expression, but higher levels of arC9-mCherry® expression caused GFP disruption regardless of ligand presence. Specifically, the mCherry® signal for the arC9 transfected cells—in which GFP was disrupted regardless of 4-HT treatment—was 8.5× greater than that of the non-disrupted cells. Therefore transfection conditions were optimized and the expression was reduced to levels similar to the ideal gates posed in (FIG. 14C) by lowering the plasmid transfection to 5 ng of DNA. This resulted in significantly less background activity while maintaining 4-HT activation (see FIG. 3B).

Figure 5A:
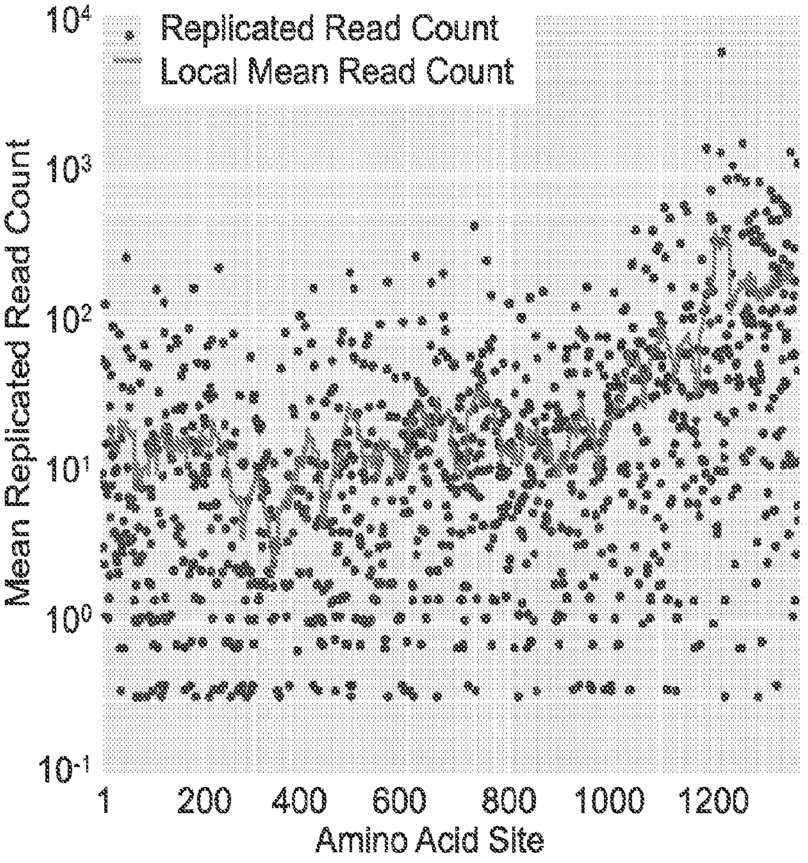
FIGS. 5A and 5B are a collection of figures showing results of sequencing a naïve transposon library, according to embodiments of the present disclosure.
Figure 5B:
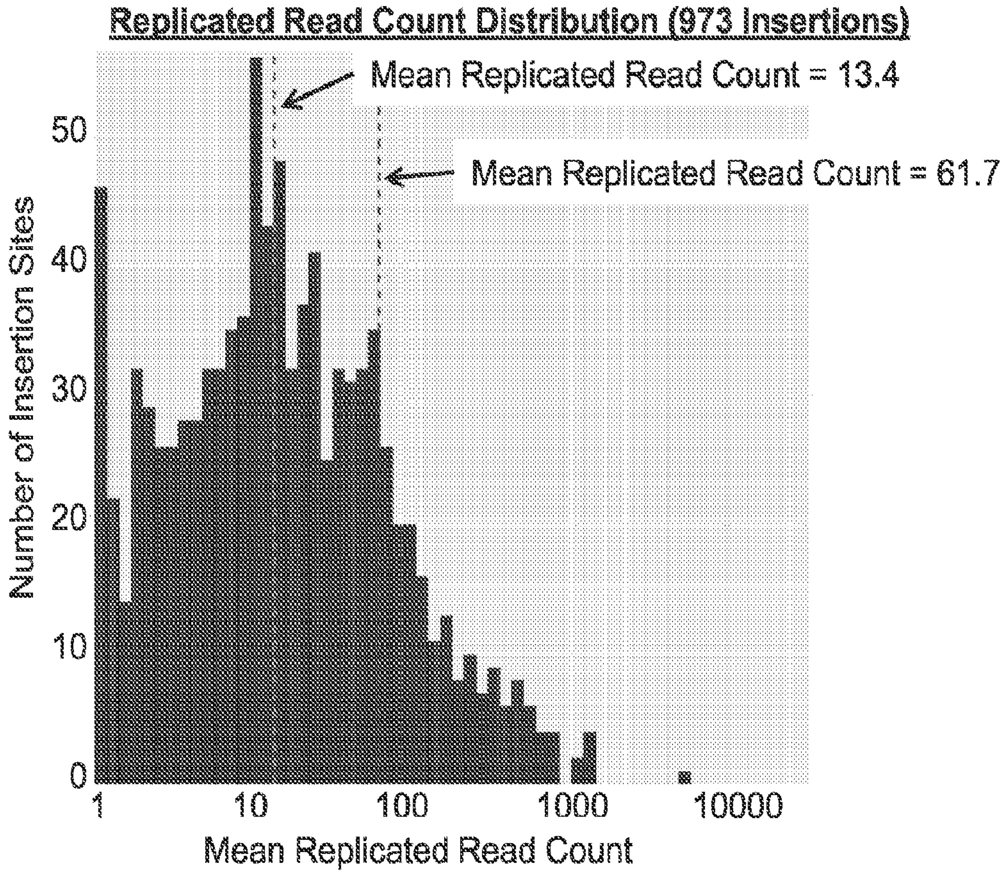

Example 2: Mapping Domain Insertion Potential into Cas9 with the Alpha-Syntrophin PDZ Protein Interaction Domain The plasticity of the Cas9 structure was profiled by examining its ability to tolerate a synthetic domain insertion while still retaining RNA-guided DNA binding activity. An unbiased Cas9 insertion library was created using randomized in vitro transposition (FIG. 1A). Briefly, an engineered Mu transposon possessing an antibacterial selection marker flanked by BsaI endonuclease sites was inserted randomly throughout a catalytically inactive Cas9 (dCas9)-containing plasmid by in vitro transposition (FIG. 1A, FIGS. 4A-4D). After selection and sub-cloning to isolate only those plasmids with transposition events inside of the Cas9 ORF, the library was characterized by deep sequencing. This analysis revealed that the library possessed good insertion coverage, with domain insertions at >70% of all possible amino acid (AA) sites in dCas9 observed at least once (FIGS. 5A and 5B). Once isolated, this naïve library was used to construct specific insertion libraries by cleavage with BsaI and religation with DNA fragments containing an ORF of interest. (FIG. 1A, FIGS. 4A-4D).

FIG. 1A. Unbiased transposon-based domain insertion library creation.

FIG. 4A-4D. Construction of a transposition library (FIG. 4A) Schematic of the Mu transposon used for transposition. (FIG. 4B) Schematic areing the inserted transposon. (FIG. 4C) ORF excision of an intra-Cas9 transposon using Type II-S restriction enzyme BsaI. Any ORF can be subsequently ligated into these sticky ends. (FIG. 4D) Description of the sticky ends and linkers used to ligate in the PDZ and ER-LBD domains. Ala and Ser are hardcoded on each side providing the correct sticky ends for a Golden Gate ligation and additional diversity is provided by “BCT” codons (encoding Ala, Ser, or Pro). In total, there are 13 possible amino acid variations per terminus.

FIGS. 5A and 5B. Naïve transposon library sequencing. (FIG. 5A) Deep sequencing of the transposon library. Sequencing and alignment of the naïve transposon insertion library indicates coverage across the Cas9 coding sequence with a bias for insertion towards the C-terminus. (FIG. 5B) Cumulative distribution of the replicated insertion site data. 973 in-frame insertions covering 71% of all possible sites were observed. All read counts represent the corrected replicated averages generated from DESeq.

Figure 6A:
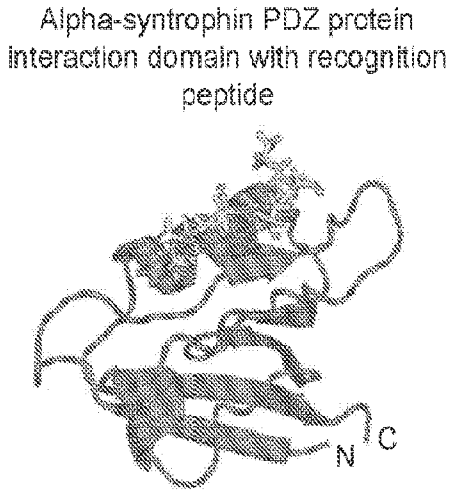
FIGS. 6A and 6B are a collection of images depicting a PDZ domain as a potential scaffolding element for Cas9, according to embodiments of the present disclosure.

The alpha-1-syntrophin PDZ domain was chosen as a proof of concept insertion domain due to its small size (86 amino acids), well-folded nature, and adjacent N- and C-termini (FIG. 6A). It was hypothesized that this domain would be minimally perturbative and act as a molecular ‘potentiometer’—where the PDZ’s capacity to insert is indicative of the absolute insertion potential of a given amino acid site within Cas9. Moreover, as the PDZs are known protein-protein interaction domains, PDZ-Cas9s identified here could further be used as protein scaffolds to recruit other domains for editing, epigenetic modification and activation/repression purposes (FIG. 6B).

Figure 6B:
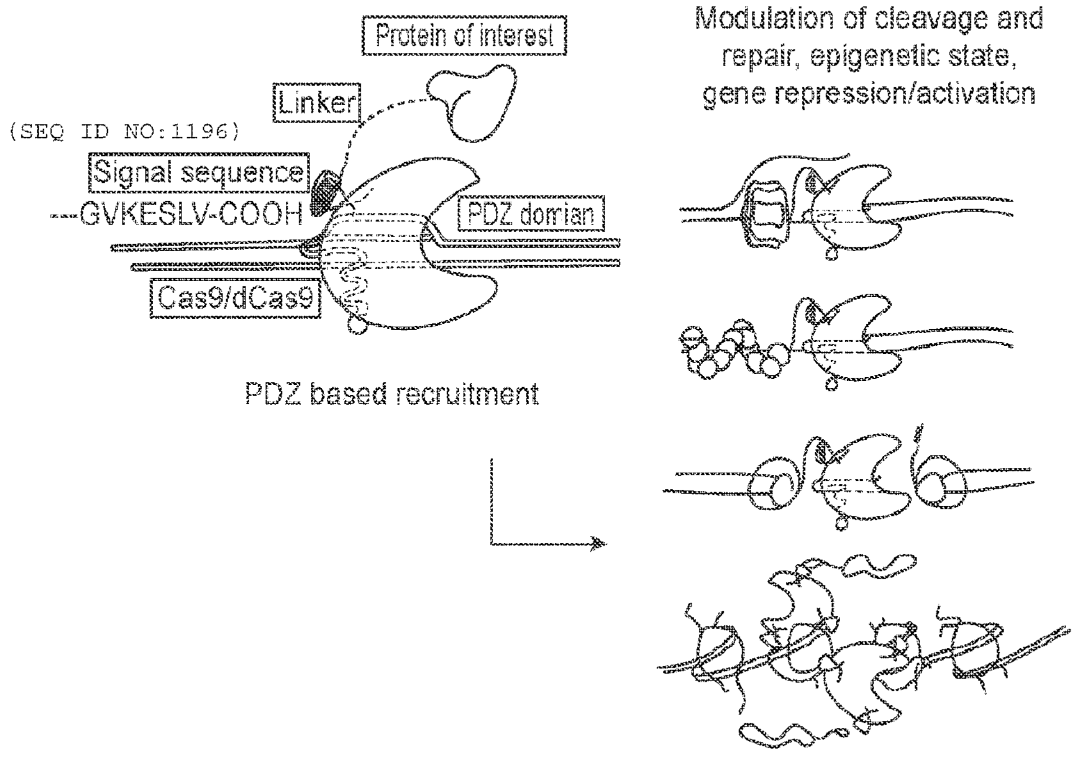

FIGS. 6A and 6B. The PDZ domain as a potential scaffolding element (FIG. 6A) The Alpha-Syntrophin PDZ protein interaction domain. The adjacent N- and C-termini and its peptide ligand are depicted (Protein Data Bank (PDB) ID: 2PDZ) (FIG. 6B) PDZ based recruitment. The PDZ domain is a protein interaction domain that specifically recognizes a seven amino acid C-terminal motif that can be modularly attached to any protein of interest. This provides a mechanism by which it is possible to recruit one or many different proteins to a cleavage site or binding site to increase the local concentration. This will allow for the recruitment of proteins that may be processive, DNA or epigenetic modifying enzymes, activators or repressor, and even libraries of protein domains fused to the PDZ recruitment amino acid sequence.

Figure 8A:
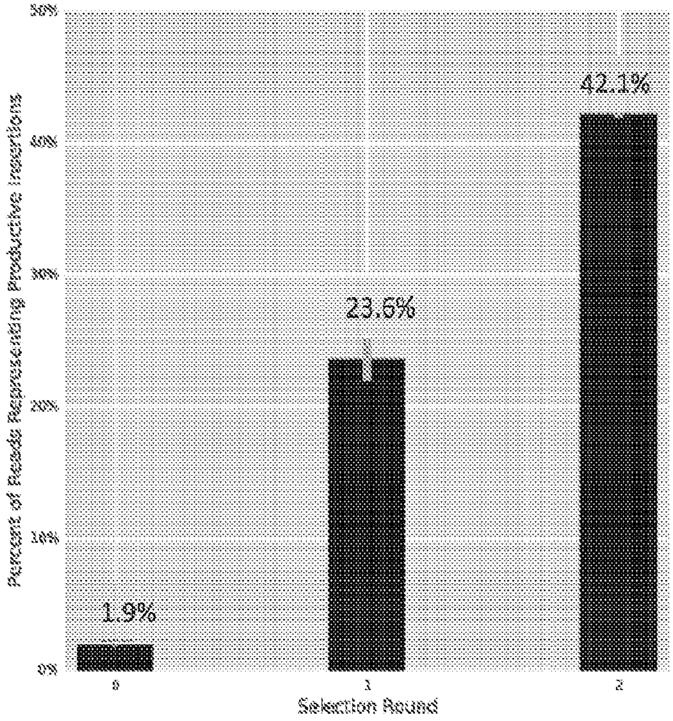
FIG. 8A-8B are a collection of figures showing domain insertion profiling of a PDZ-insertion library, according to embodiments of the present disclosure.
Figure 8B:
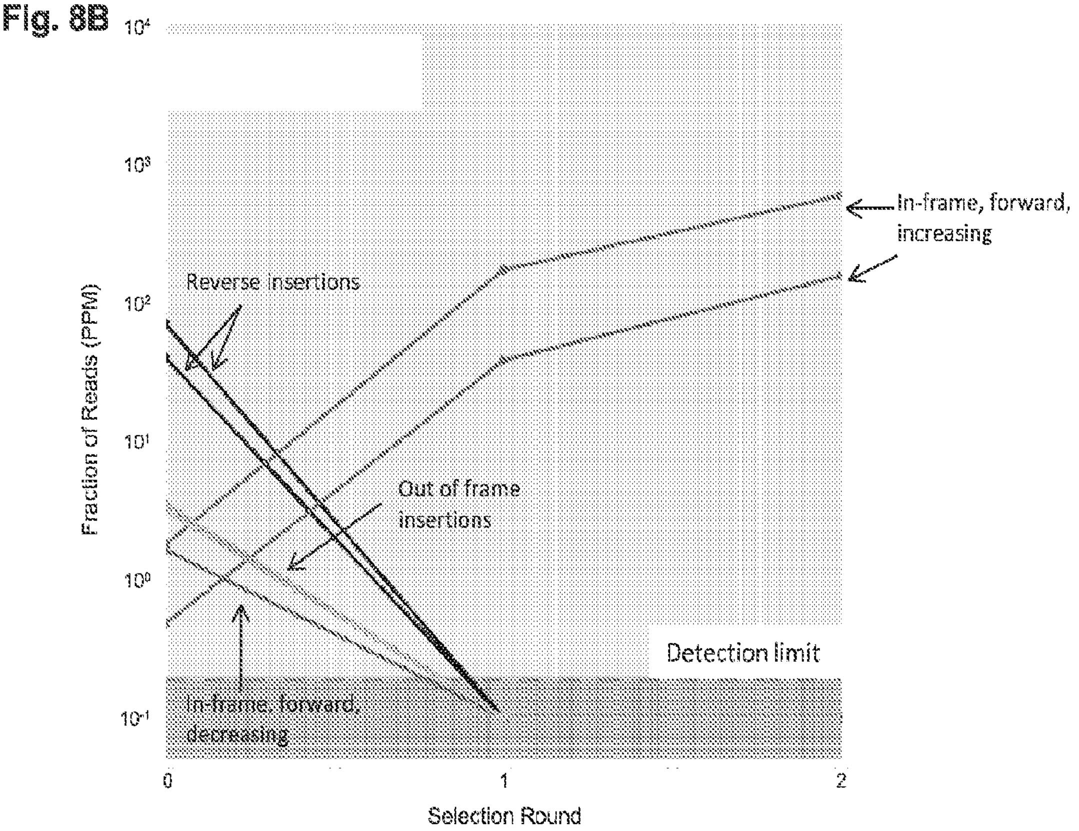

The PDZ domain possessing flanking amino acid linkers was cloned into the naïve library (FIGS. 4A-4D) and passaged through two rounds of a CRISPRi screen. Briefly, cells expressing Red Fluorescent Protein (RFP) and Green Fluorescent Protein (GFP) were assayed using fluorescence activated cell-sorting (FACS) to identify Cas9 variants capable of repressing RFP in a single guide RNA (sgRNA)-dependent fashion (FIGS. 7A-7C). After sorting, the Cas9 libraries were subjected to deep sequencing to identify insertion sites. Comparison of the pre- and post-screen libraries demonstrated that the screen increased the fraction of in-frame insertions by ~20 fold (FIG. 8A). Such insertions are referred to as ‘productive’ because they can produce a full-length insertion protein. Tracking individual clones revealed that non-productive insertions are often cleared from the library (FIG. 8B). Thus, the screen enriched productive PDZ-dCas9 insertion mutants.

FIGS. 8A and 8B. Domain insertion profiling of the PDZ-insertion library (FIG. 8A) Screening-based enrichment of functional Cas9 clones. Passage of the PDZ insertion library through a round of selection increased the number of in-frame, forward insertions (‘productive’) sequenced. Thus the CRISPRi based screen enriched full length coding proteins. Error bars represent standard deviation of four technical replicates. (FIG. 8B) Trajectories of representative insertion site clones. Out of frame and reverse insertions were observed to be eliminated from the library.

Figure 1B:
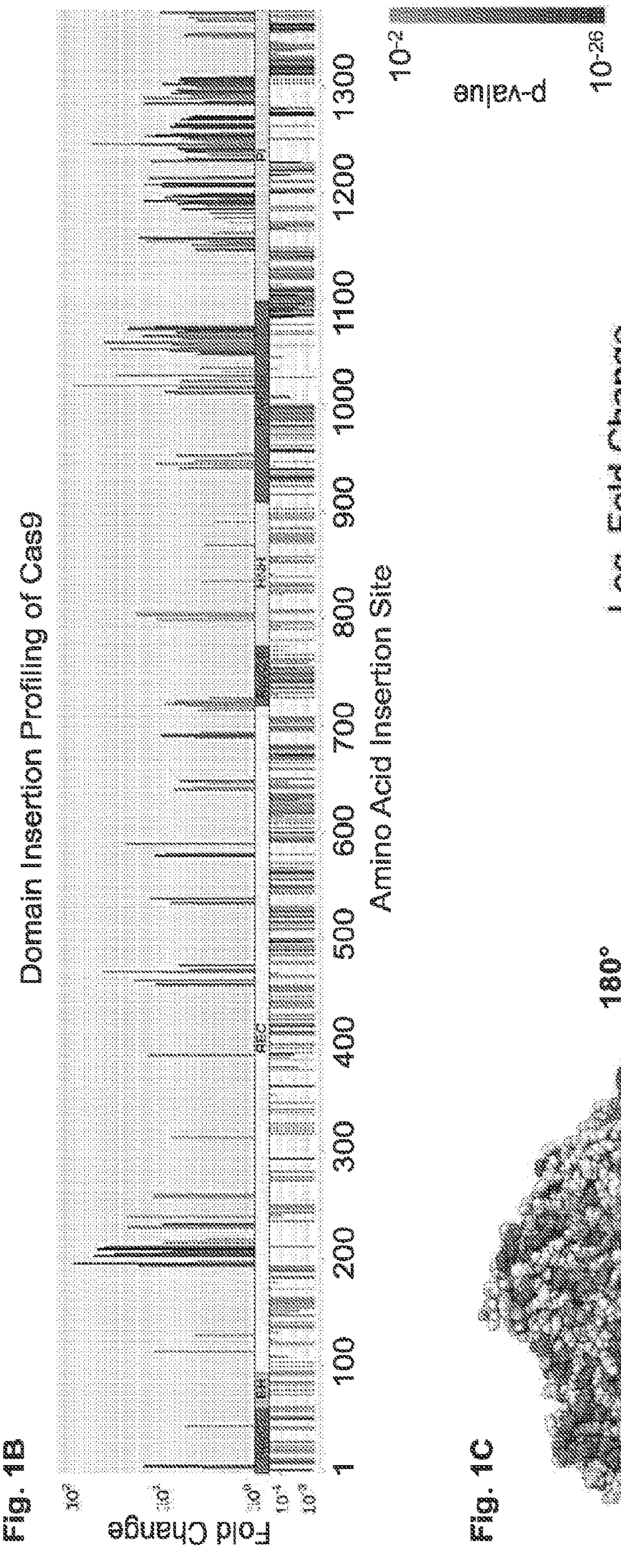
Figure 1C:
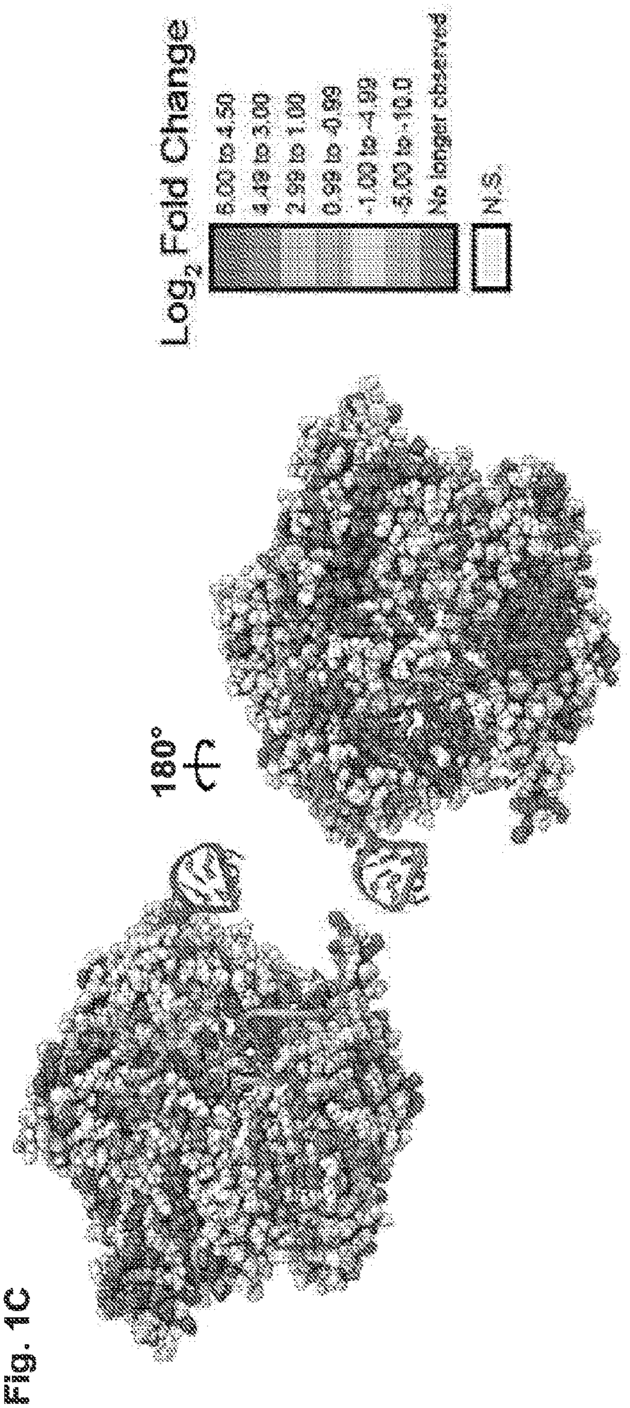
Figure 9A:
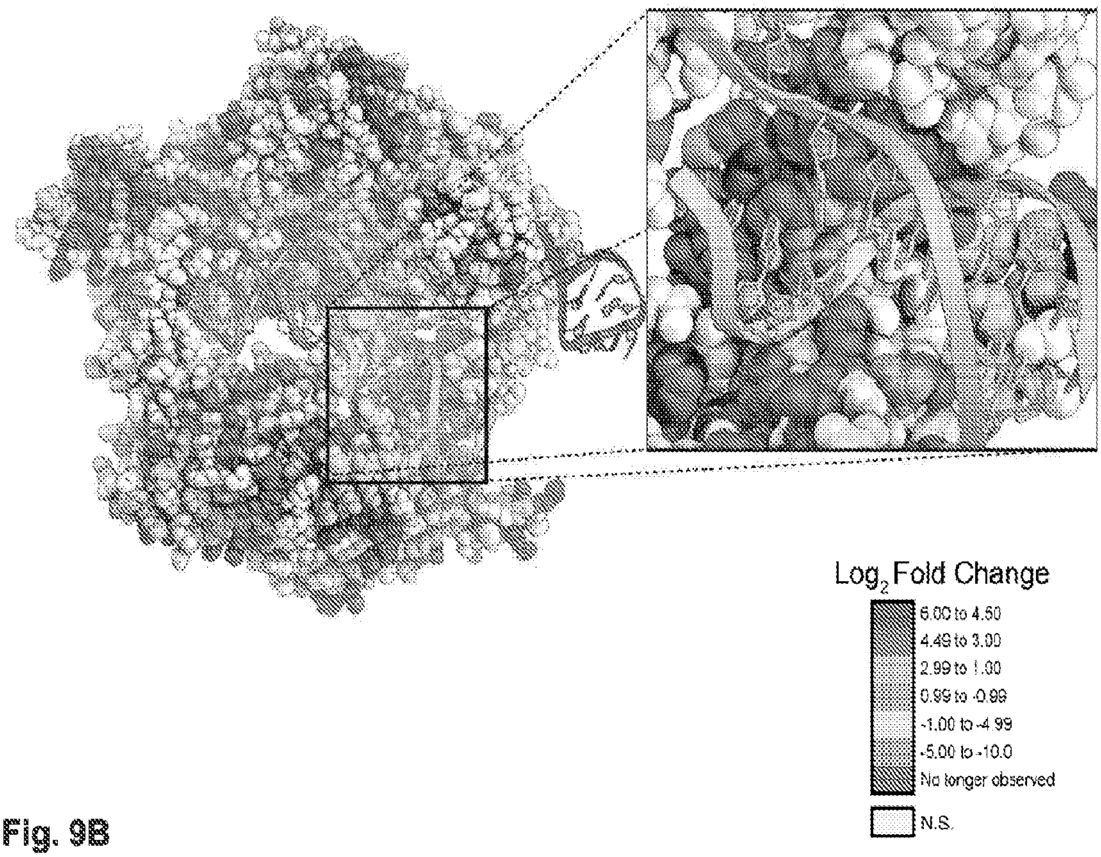
FIG. 9A-9B are a collection of images showing PDZ-insertion sites in Cas9, according to embodiments of the present disclosure.
Figure 9B:
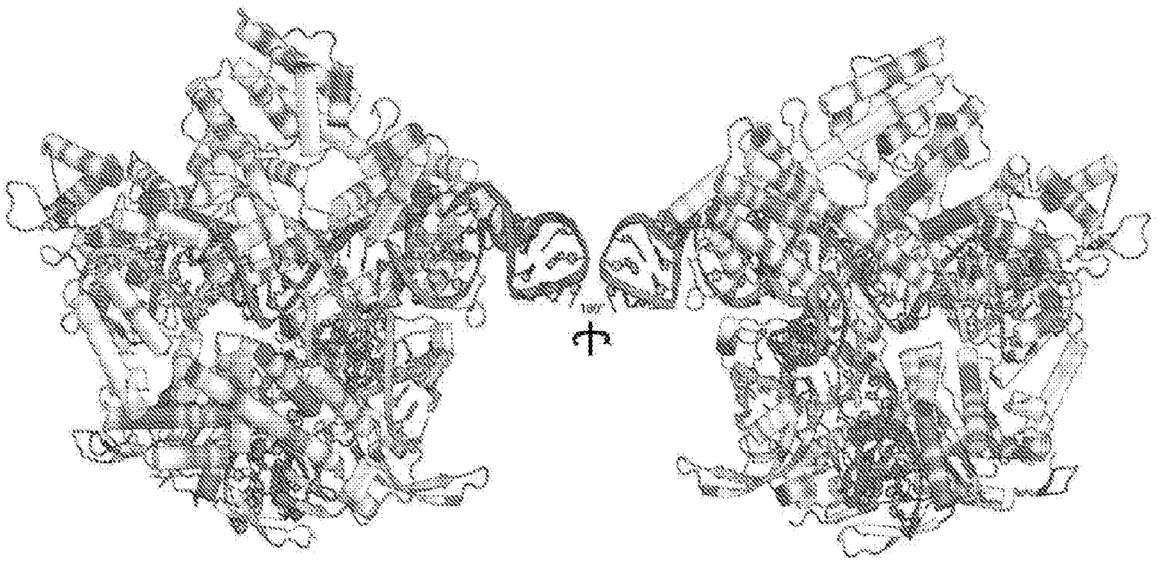
Figure 10A:
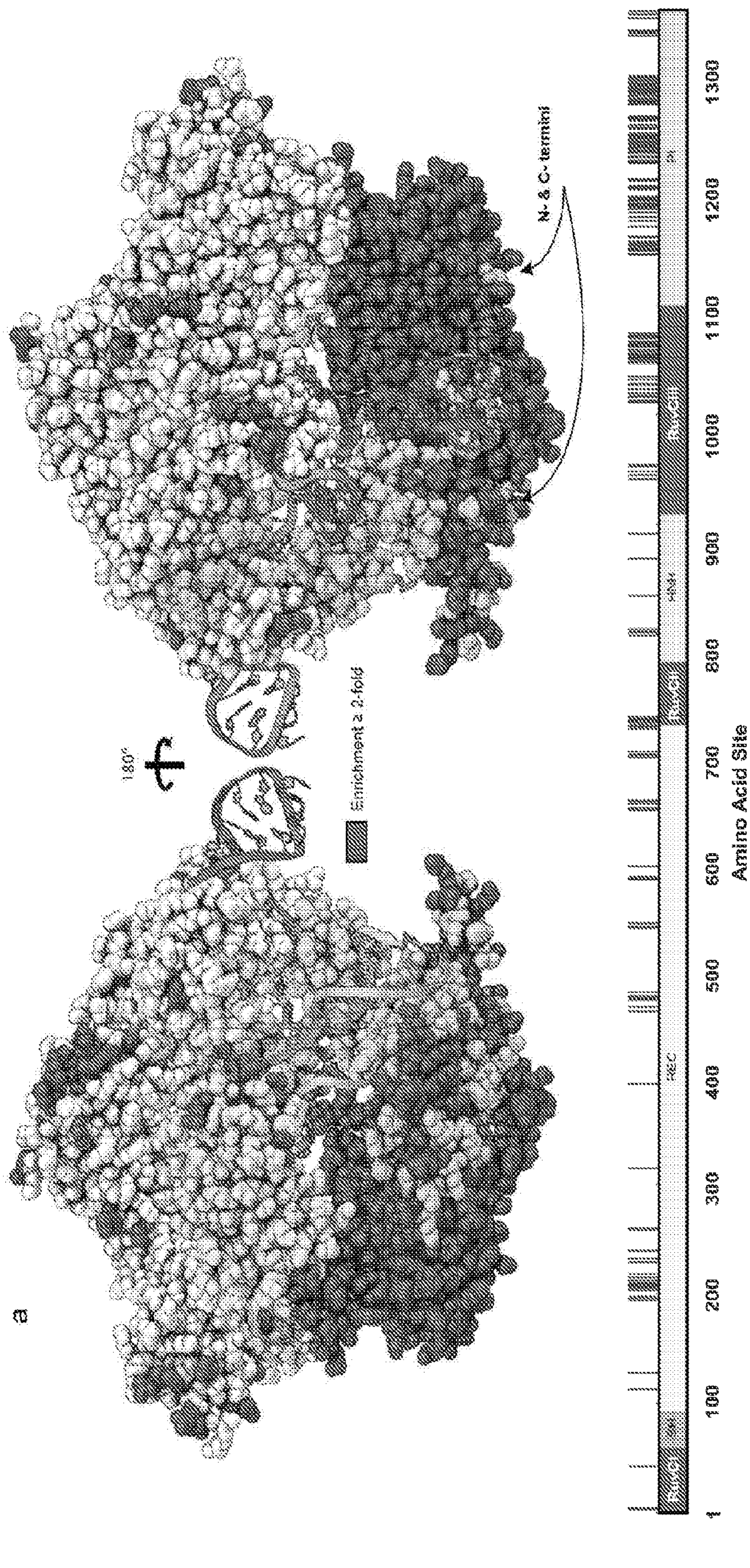
FIG. 10A-10B are a collection of images showing PDZ-insertion sites in Cas9, according to embodiments of the present disclosure.
Figure 10B:
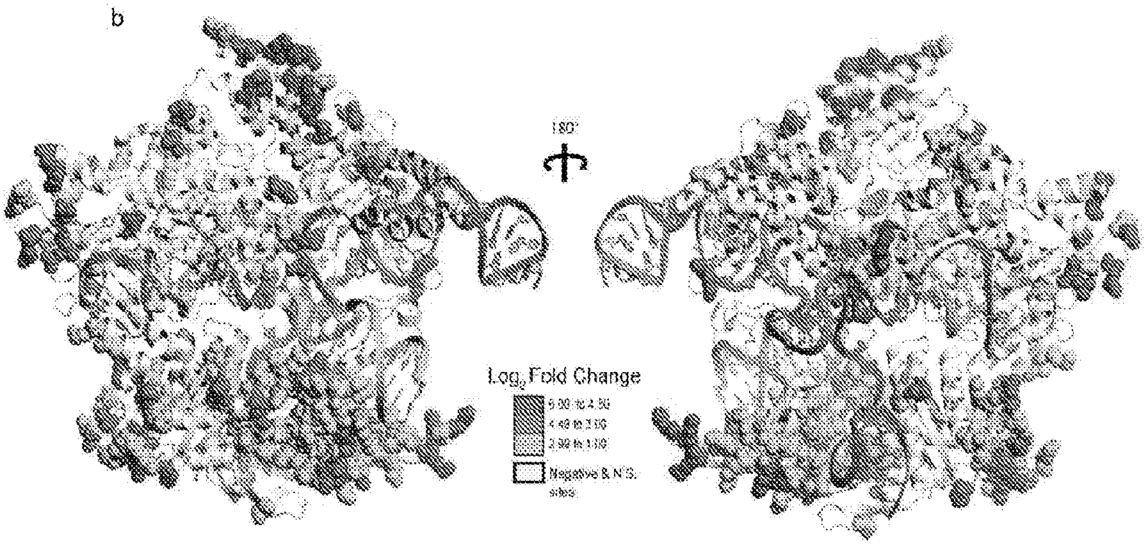
Figure 15:
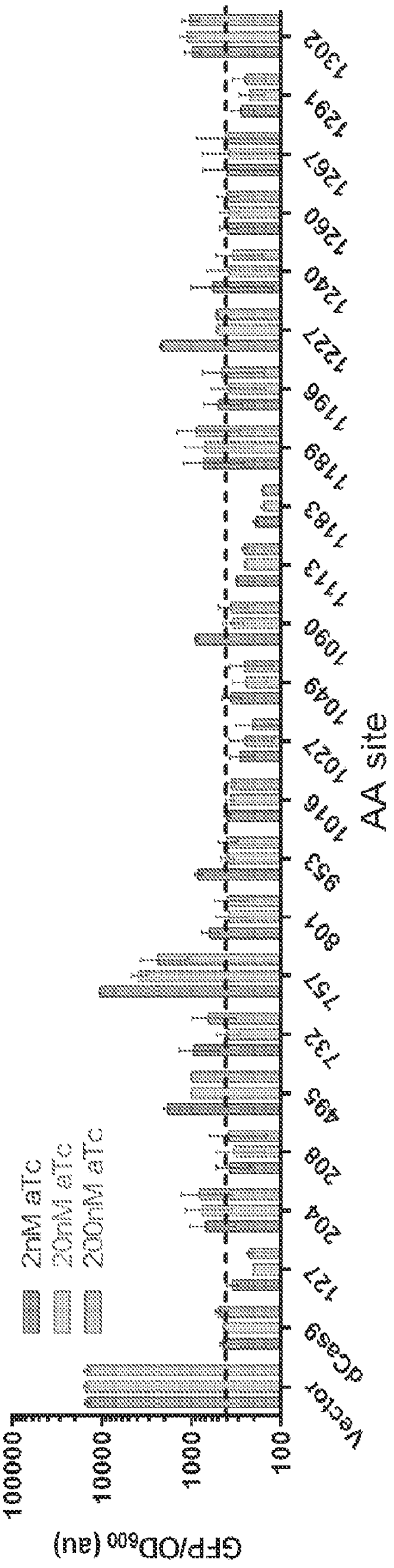
FIG. 15 is a figure showing validation of PDZ domain insertions in Cas9, according to embodiments of the present disclosure.

Calculation of the log 2-fold enrichment of insertion sites between the final and unscreened PDZ insertion library revealed statistically significant changes for roughly half of the amino acid (AA) sites in Cas9 (FIG. 1B, FIG. 15, Table 1 in FIGS. 19A-19C). Domain insertions at the majority of residues within dCas9 are strongly selected against, with the bulk of clones falling out of the pool by the second round of screening. Sites with negative fold changes were highly overrepresented in critical motifs such as the core of Cas9, sgRNA-binding grooves, the bridge helix, the PAM-binding pocket and the DNA:RNA heteroduplex recognition channel (FIG. 1C, FIGS. 9A and 9B). Nevertheless, small local clusters of amino acids that are tolerant to insertions were found and a total of 176 statistically significant ($p<0.1$) sites enriched ≥2-fold were recovered (FIG. 1B, FIG. 1C). When mapped onto the holo Cas9-DNA-RNA crystal structure 11, the enriched insertion sites tended to cluster in discrete regions, often around flexible loops, the ends of helices, and at solvent-exposed residues. Specifically, hotspots were found in an abundance of Cas9's domains: at six distinct clusters within the alpha helical (RNA recognition) lobe, the linker between the alpha helical and nuclease lobes, the HNH domain, three extended sites in the RuvCIII region and throughout the PAM interacting (C-Terminal) domain (FIG. 1C, FIGS. 10A and 10B). These insertion sites provide unprecedented access to both 5' and 3' ends of the bound DNA (~10 Å) as well as the groove hypothesized to hold the non-targeted DNA strand. Thus, these insertions open the door for much closer and specific interactions with bound DNA. Intriguingly, a number of tolerated insertions in alpha helices and beta sheets was found to be concentrated around the PAM interacting domain (i.e. AA 1291, 1260, 1196, 1267, 1064, 1161, 1148). The insertions presumably disrupt these secondary structures but have little impact on binding function.

FIGS. 1B and 1C. (FIG. 1B) Fold change values for insertions at specific amino acid sites after two rounds of screening. Positive values represent a preference for domain insertion at the site to remain in the library after screening for function. Negative values indicate a loss of clones with an insertion at the site. More significant P values are represented as darker color bars. Dashed bars represent sites that were not sequenced before screening. Negative bars that reach $10^3$ represent clones which have been cleared from the library (i.e. not observed after selection). (FIG. 1C) $Log_2$ fold change values mapped onto the structure of Cas9 (PDB ID:4UN3).

FIG. 15. Validation of PDZ Domain Insertions for dCas9 based repression of GFP in *E. coli*. Individual dCas9-PDZ insertion clones were recovered and tested for repression of GFP in comparison to wild-type (wt) dCas9 and a negative control. Most are wt levels of repression.

FIG. 9A-9B. PDZ-insertion sites avoid critical structural motifs. (FIG. 9A) Mapping the $log_2$ fold change of the PDZ-insertions onto the RNA:DNA holo Cas9 crystal structure (PDB ID: 4UN3) demonstrates how the unbiased insertion technique can experimentally delineate regions of critical structure and function. The PAM binding pocket (PAM residues in yellow) and the RNA:DNA channel are selected against. (FIG. 9B) PDZ insertions are not readily observed in core packing regions of the RuvC and RecI domains and are also selected against in the sgRNA binding grooves (FIG. 1C) and bridge helix.

FIGS. 10A and 10B. Mapping enriched PDZ-insertion sites (FIG. 10A) Mapping the enriched insertions sites onto a RNA:DNA bound Cas9 crystal structure (PDB ID: 4UN3). Sites enriched by at least two-fold are indicated. Domains are indicated in the primary sequence bar. (FIG. 10B) Enriched sites with the degree of saturation mapped to fold change in the profiling. Many sites with high fold-change mapped to amino acids that are unresolved in the crystal structures and are presumably in unstructured loops.

Figure 1D:
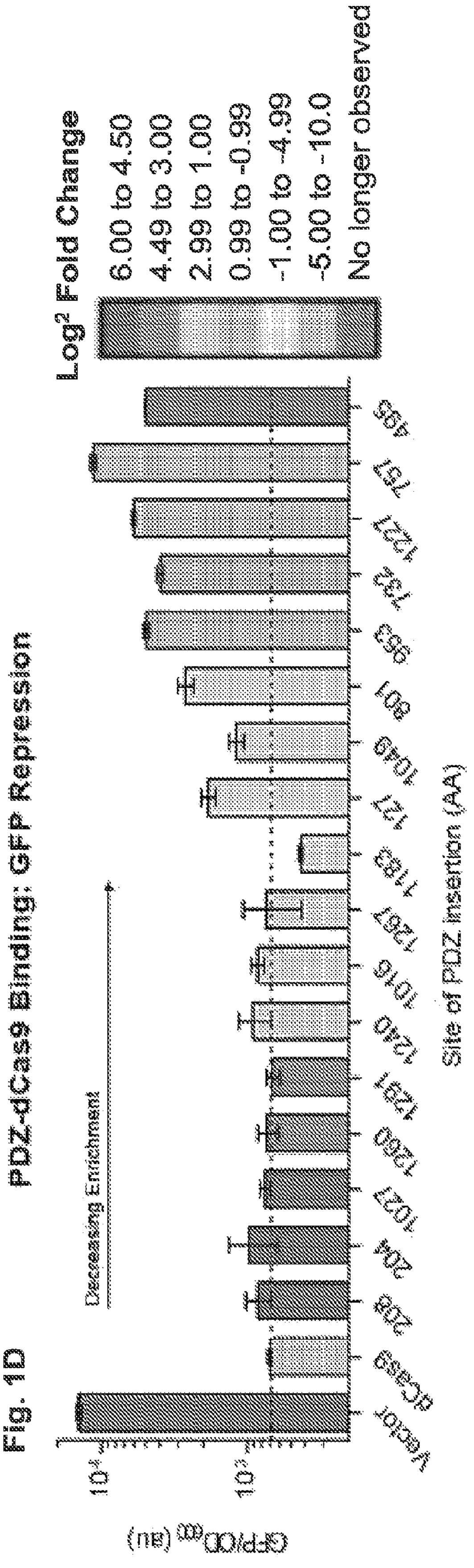
Figure 1E:
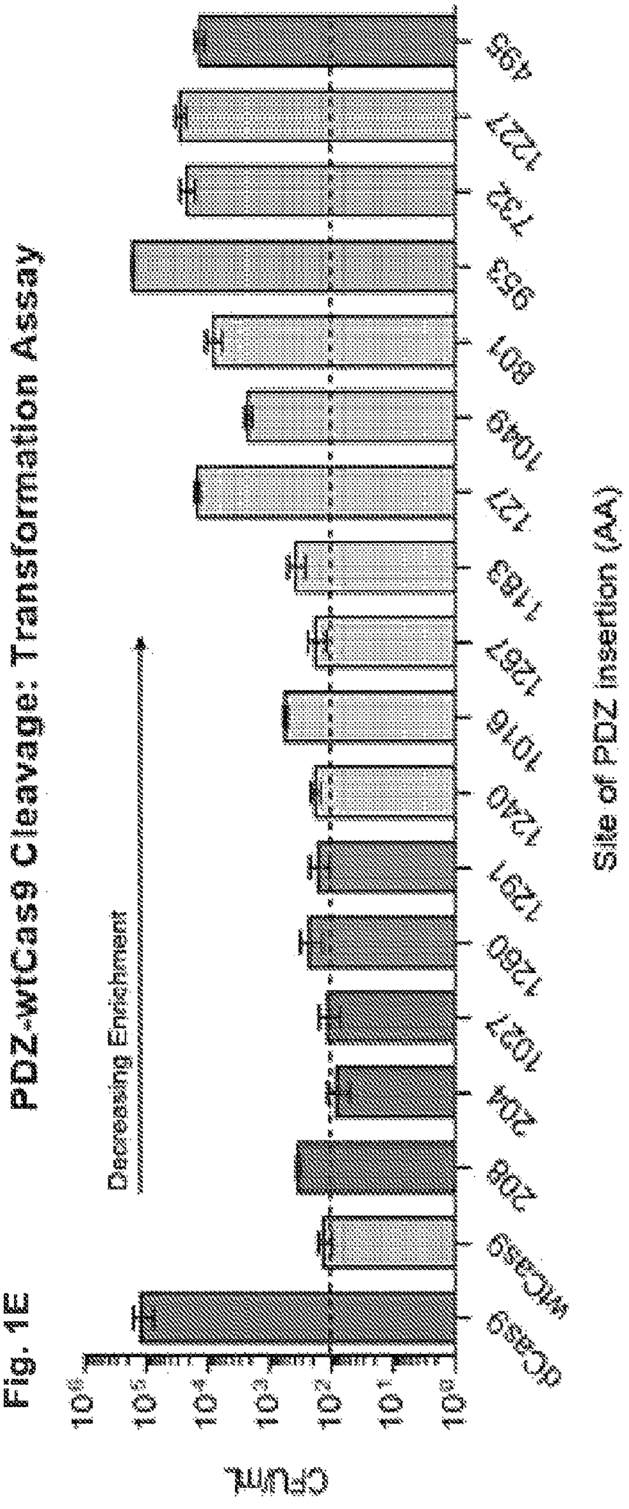

In order to confirm the binding activity of dCas9 proteins with PDZ domain insertions, plasmid DNA for individual clones was isolated and used to transform *E. coli* together with a GFP-targeting sgRNA-expression plasmid. When cells were tested for GFP repression, effective repression was found to correspond well with the calculated fold change of the insertion site, where highly enriched clones perform as well as wild-type (WT) dCas9 (FIG. 1D). To determine whether the PDZ-Cas9 clones still possessed nuclease activity, the catalytic residues (D10 & H840) were reintroduced and tested in an *E. coli* based transformation assay. In this assay, effective DNA cutting leads to genomic cleavage and cell death. Once again, cleavage activity correlated with fold change, and the most highly enriched PDZ-Cas9 clones maintained WT Cas9 levels of cleavage-induced cell death (FIG. 1E). This striking result demonstrated that it is possible to insert an entire exogenous domain at numerous sites within Cas9's primary sequence while maintaining native activity levels.

FIGS. 1D and 1E. (FIG. 1D) GFP repression activity of individual PDZ insertion sites. Values represent biological triplicates with standard deviation, constructs are in order of decreasing fold change. (FIG. 1E) Cleavage activity of clones via an *E. coli* based transformation assay. Cas9 activity results in genomic cleavage and lower CFU/mL.

Figure 11:
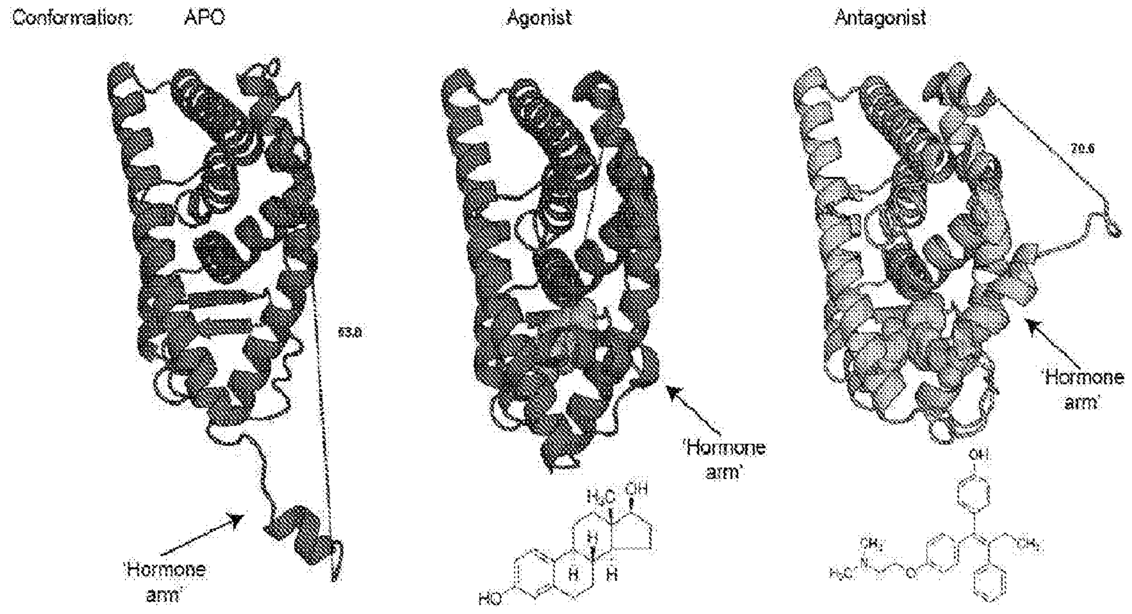
FIG. 11 is an image showing conformations of the estrogen receptor (ER) alpha ligand binding domain (LBD).

Example 3: Creation of a Switch-Like Cas9 Though Insertion of the Estrogen Receptor Ligand Binding Domain Whether unbiased domain insertion profiling could be used to reveal sites in Cas9 amenable to allosteric coupling was explored. As a proof of concept, the well-studied Estrogen Receptor a Ligand Binding Domain (ER-LBD; residues 302-552 of ERα) was chosen. Based on crystallographic data, this domain is known to adopt distinct conformations dependent on ligand binding; the antagonist-bound conformation places the N- and C-termini of ER-LBD substantially closer together (~20 Å) than either the apo or agonist-ligand bound forms (FIG. 11). This conformational switch serves as a mechanism by which an allosteric signal can be transduced.

FIG. 11. Conformations of the estrogen receptor alpha ligand binding domain (ER-LBD). Conformations of the ER-LBD. Crystal structures of the apo, 17-beta-estradiol and 4-hydoxytamoxifen-bound ER-LBD (PDB ID's:1A52, 1GWR, 3ERT respectively) clearly demonstrate the range of conformational change this domain can undergo. The 'hormone arm,' or helix 12, places the N- and C-termini up to 63 Å apart in the apo form, 37 Å in the agonist bound form (β-E), and 20 Å in the antagonist bound structure.

Figure 2A:
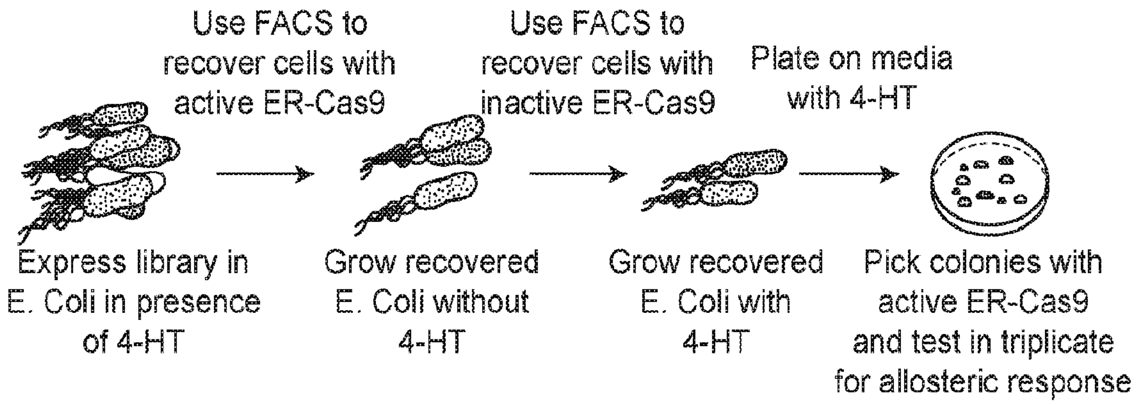
FIG. 2A-2E are a collection of diagrams, images and figures showing creation of a switch-like Cas9, according to embodiments of the present disclosure.
Figure 12:
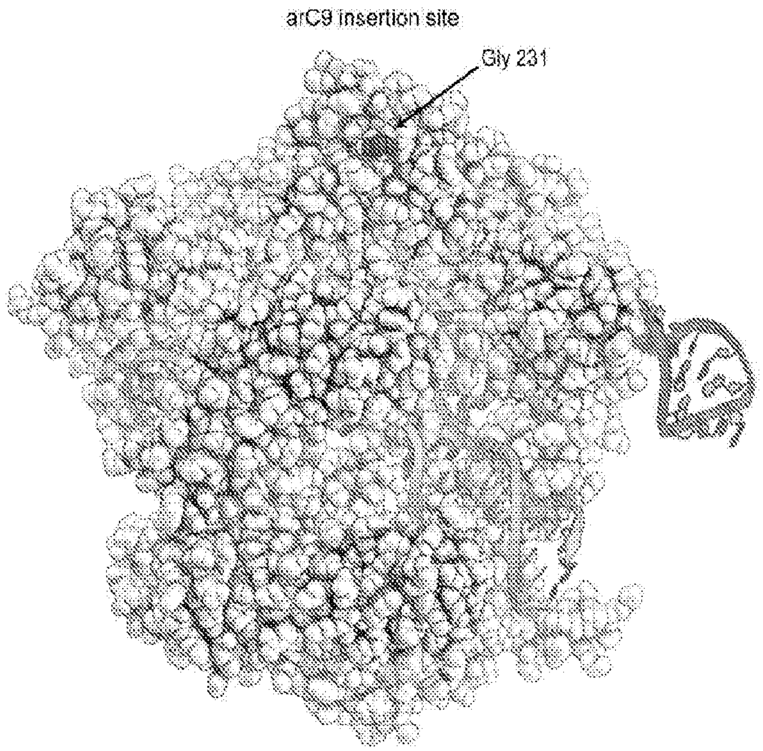
FIG. 12 is an image showing the ER-LBD insertions site in Cas9, according to embodiments of the present disclosure.
Figure 16:
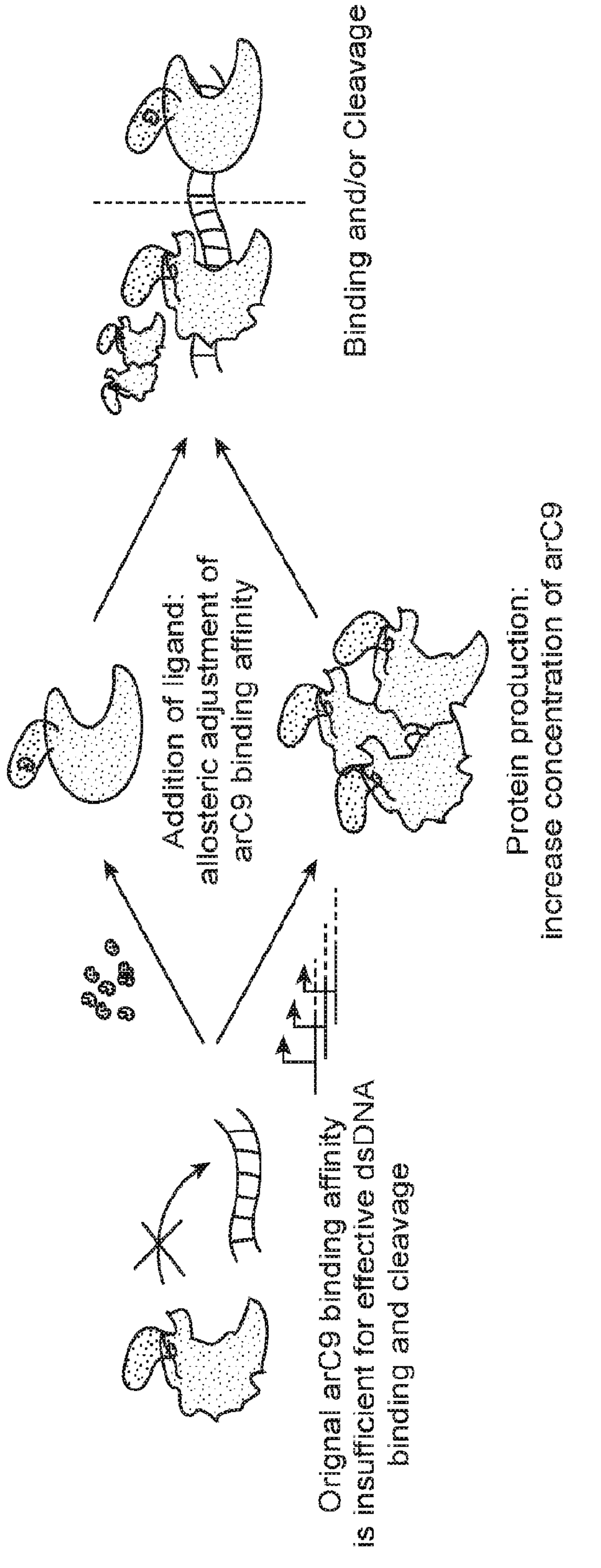
FIG. 16 is a figure showing a schematic model to explain the dual dependence of arC9 activity on expression level and 4-HT.

In order to create an allosterically-regulated Cas9 (arC9), the ER-LBD was introduced into the naïve dCas9 domain insertion library in the manner previously described and passaged through a modified version of the RFP CRISPRi-based assay. Briefly, a positive screen in the presence of ligand 4-hydroxytamoxifen (4-HT) was carried out, followed by a negative screen for loss of activity in the absence of ligand (FIG. 2A). Clones were recovered by plating, re-transformed with sgRNA targeting GFP, and assayed for repression in *E. coli*. An insertion site at AA 231 that demonstrated a 4-HT-dependent decrease in GFP fluorescence was identified, indicating switch-like behavior (FIG. 12, FIG. 16). Notably, this site was also enriched during the PDZ screen (Table 1 in FIGS. 19A-19C).

FIG. 2A. Schematic of the screen/counter-screen procedure to select for ligand responsive ER-Cas9 insertions.

FIG. 12. arC9 Hit. Depiction of the recovered ER-LBD insertion site at amino acid Gly231 (PDB ID: 4UN3).

FIG. 16. Allosteric response to 4-Hydroxytamoxifen (4-HT) of ER-LBD domain insertions. ER-LBD was found to regulate dCas9 based GFP repression by domain insertion into identified sites 199-200, 230-231 and 1249-1250.

Figure 2B:
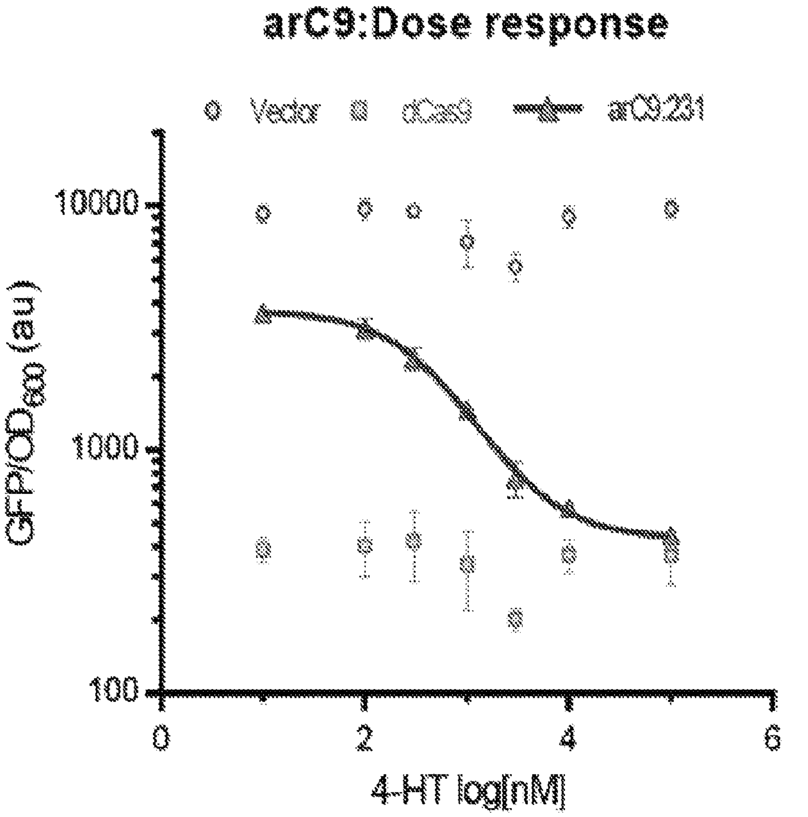
Figure 2C:
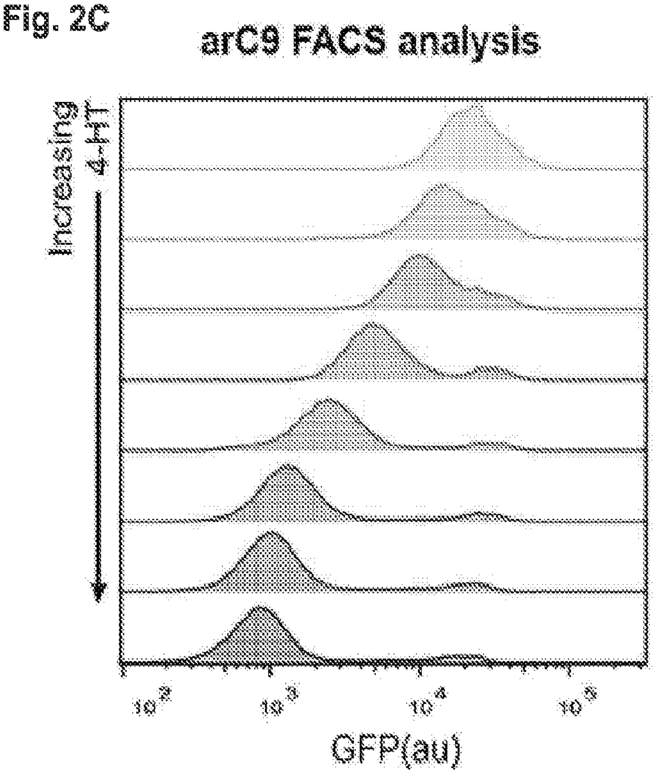
Figure 2D:
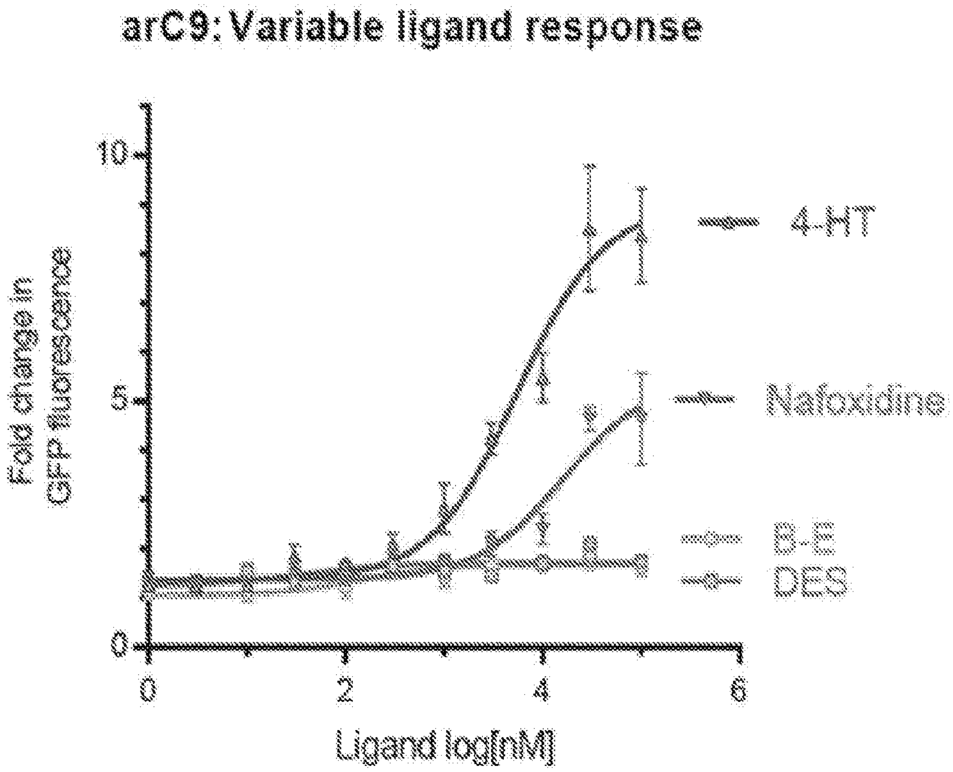
Figure 2E:
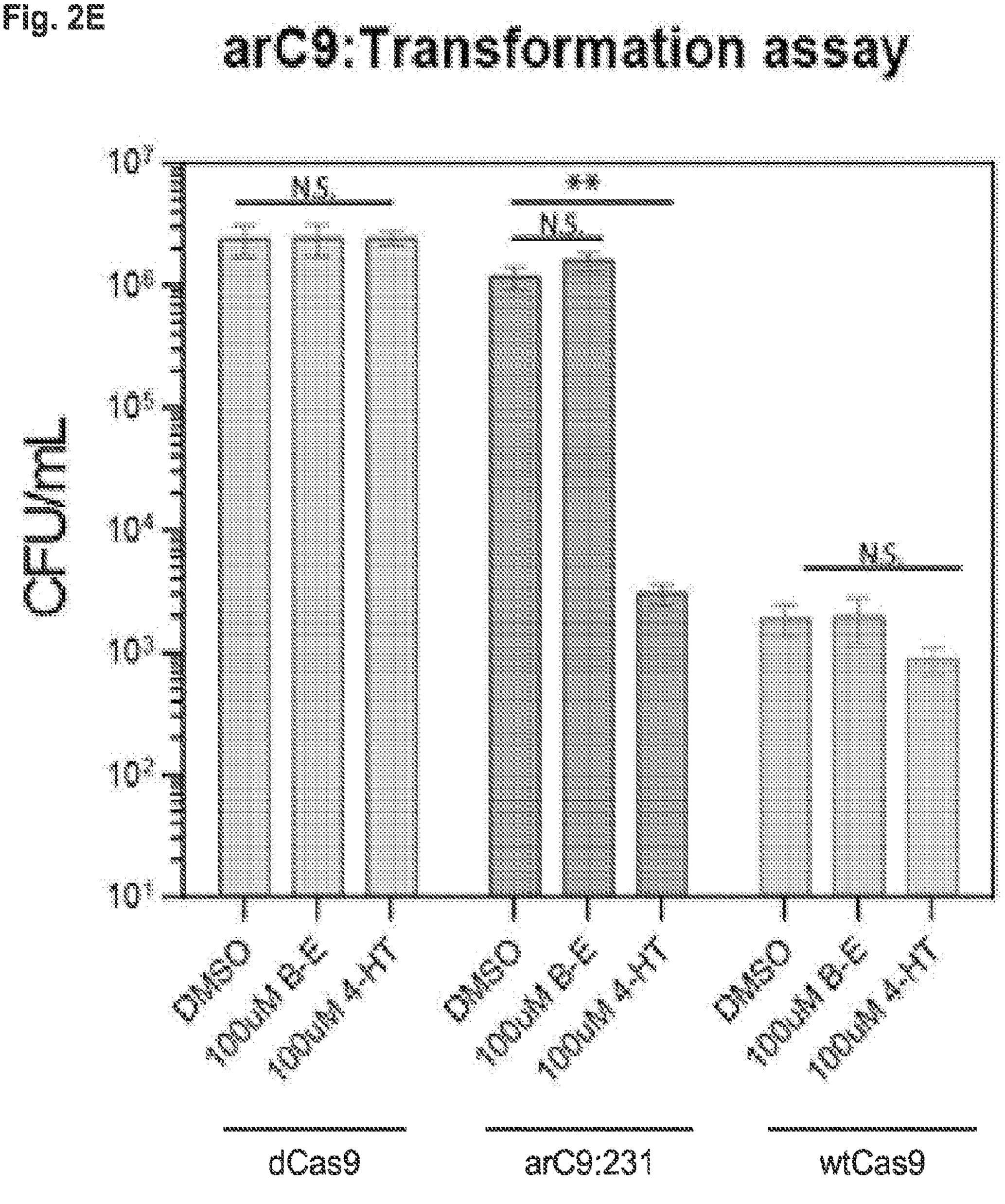

Insertion of ER-LBD at Gly231 (arC9:231) was first characterized in *E. coli*. ArC9:231 exhibited 4-HT dose-dependent repression of GFP with a ~10 fold change in activity in ensemble and single cell experiments (FIGS. 2B and 2C). Therefore arC9 represented a tunable CRISPRi effector. As hypothesized, arC9 also exhibited clear ligand discrimination. CRISPRi-based GFP repression increased only with ligands that encourage the ER-LBD to enter an antagonist conformation (4-HT and nafoxidine) as opposed to ligands encouraging the agonist conformation, beta-estradiol and diethylstilbestrol (FIG. 2D). This further supported the argument that the ER-LBD insertion at AA 231 was able to transduce the specific binding of 4-HT, the antagonist ER-LBD conformation, into Cas9 activity. To determine if arC9:231 also exhibited allosteric control over cleavage activity, the catalytic residues were reintroduced (D10 & H840) and tested in the *E. coli* transformation assay (FIG. 2E, FIG. 17). arC9 increased chromosomal cleavage-based *E. coli* cell death at least 100-fold more in the presence of 4-HT ligand than with DMSO vehicle control (p value<0.01), indicating that allosteric modulation of arC9 also extends to cleavage activity.

FIG. 2B-2E. (FIG. 2B) Dose-response curve to 4-HT. ArC9:231 has an $IC_{50}$ of 440±70 nM (S.D) and a Hill coefficient of 1.04 as expected for the non-cooperative binding of 4-HT to ER-LBD. (FIG. 2C) Single cell analysis of arC9:231 binding in response to increasing concentrations of 4-HT. Flow cytometry data agrees well with ensemble data demonstrating a >9 fold switch between arC9 plus and minus 4-HT (arC9 GFP signal without 4-HT mean: 24,310 (au) and with 100 μM 4-HT: 2,631 (au). (FIG. 2D) Dose response of arC9:231 binding to various ligands (B-E and DES are beta-estradiol & diethylstilbestrol). Response is normalized to vector control fluorescence under the same conditions and testing was done in SOB media. ArC9 only responds to ligands which bind to the ER-LBD in the antagonist conformation (see FIG. 11). (FIG. 2E) Switching of arC9:231 cleavage activity.

Figure 17:
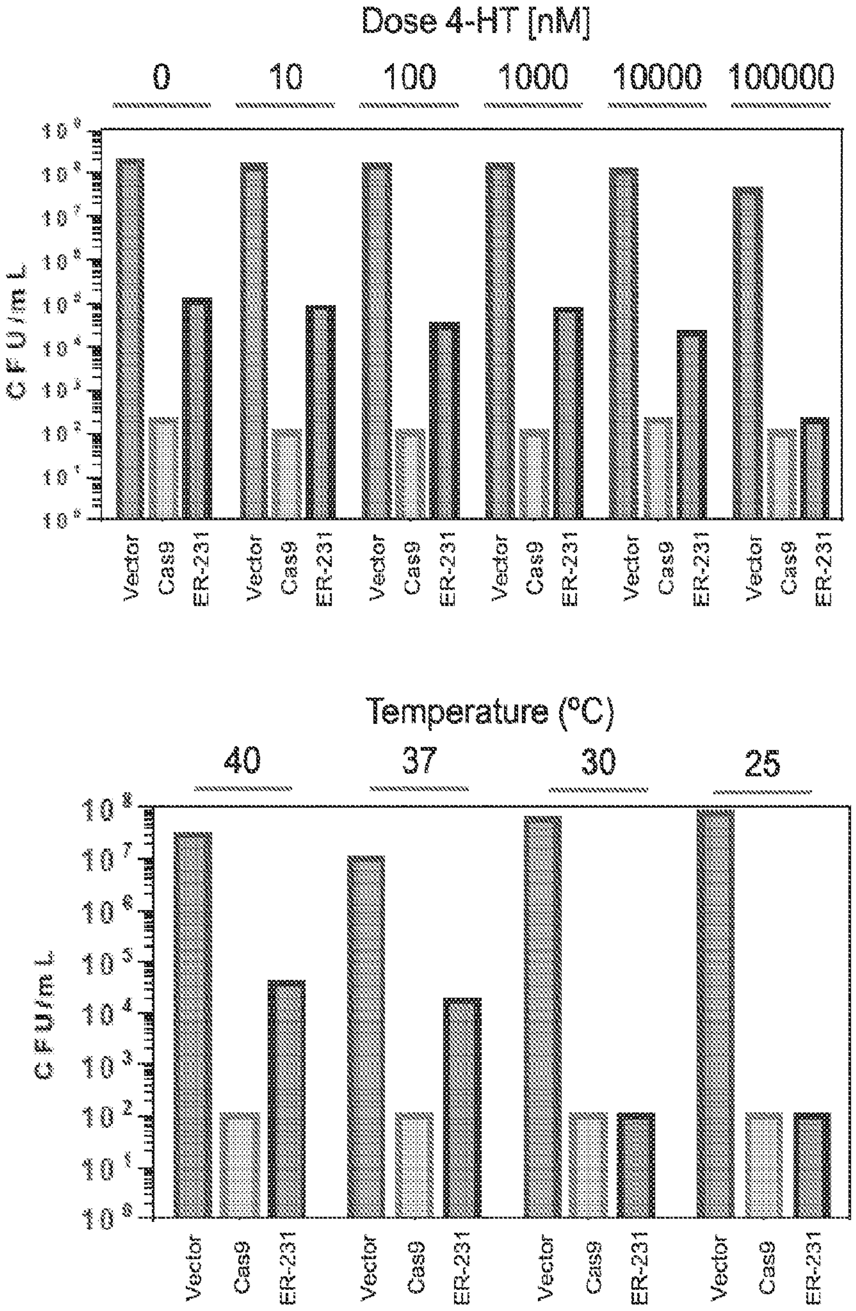
FIG. 17 is a figure showing cleavage responses of arC9: 231 to 4-HT and temperature, according to embodiments of the present disclosure.

FIG. 17. Cleavage response of Allosteric ER-Cas9 231 to 4HT and Temperature in *E. coli*. Allosteric ER-Cas9 231 increases its cleavage of the genome leading to death in *E. coli* killing 10^3 more CFU in the presence of 4-HT or a lower temperature.

Figure 3A:
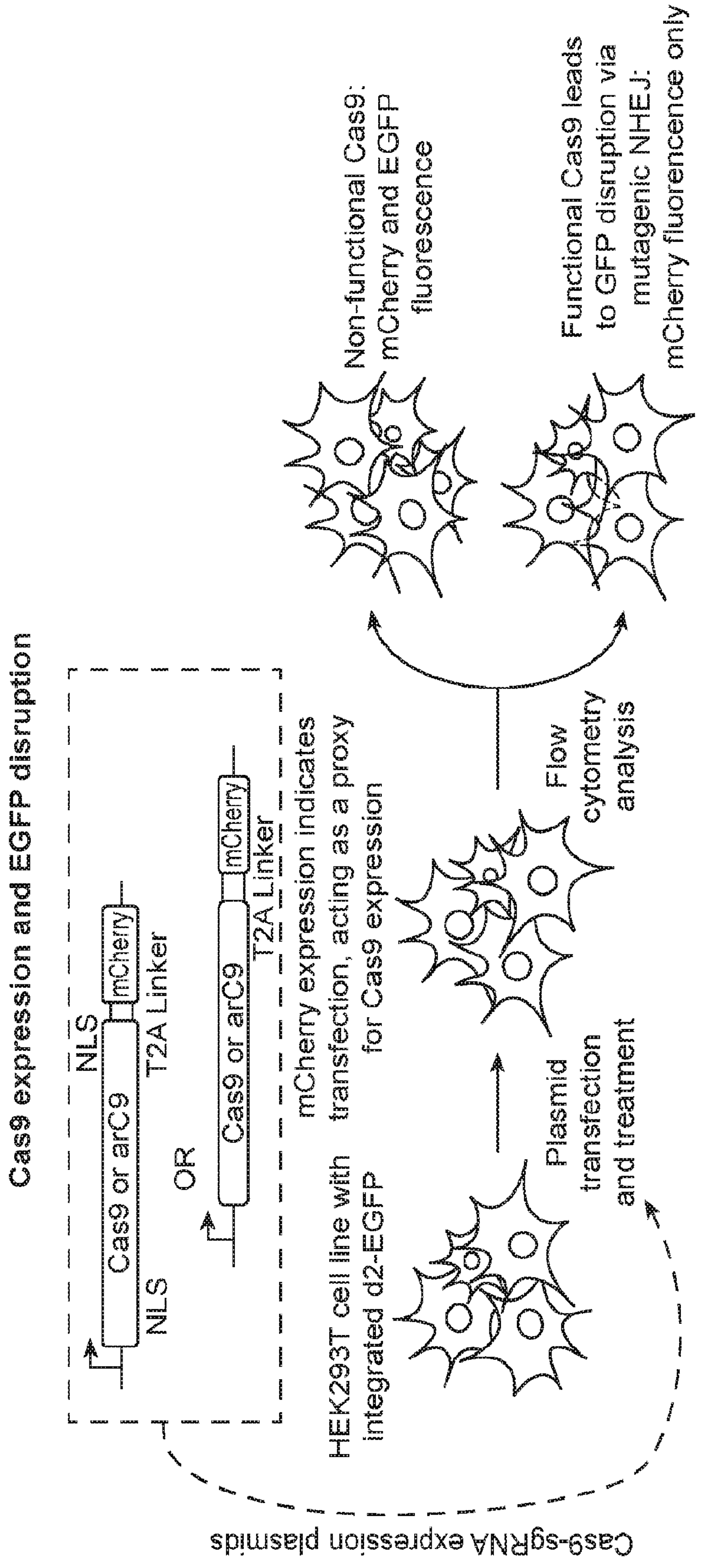
FIG. 3A-3D are a collection of diagrams, images and figures showing testing of arC9 in eukaryotic cells, according to embodiments of the present disclosure.

Example 4: Testing arC9 in Eukaryotic Cells arC9:231 function was tested in eukaryotic cells. Cas9 and arC9:231 constructs flanked by nuclear localization sequences (NLS) were transfected into a Human Embryonic Kidney (HEK293T) cell line possessing lentiviral integrated EGFP-PEST and assayed for GFP disruption (FIG. 3A, FIGS. 13A and 13B). After 72 hours, Cas9 was found to disrupt 91% of the EGFP signal regardless of treatment condition (FIG. 3B, FIGS. 14A-14C). A 6-fold induction of arC9-mediated GFP disruption upon the addition of 4-HT (10.9±0.5% to 66±1%) (FIG. 3B) was observed over this time period. Higher expression conditions led to an increase of GFP disruption even in the absence of 4-HT (FIGS. 14A-14C).

Figure 3B:
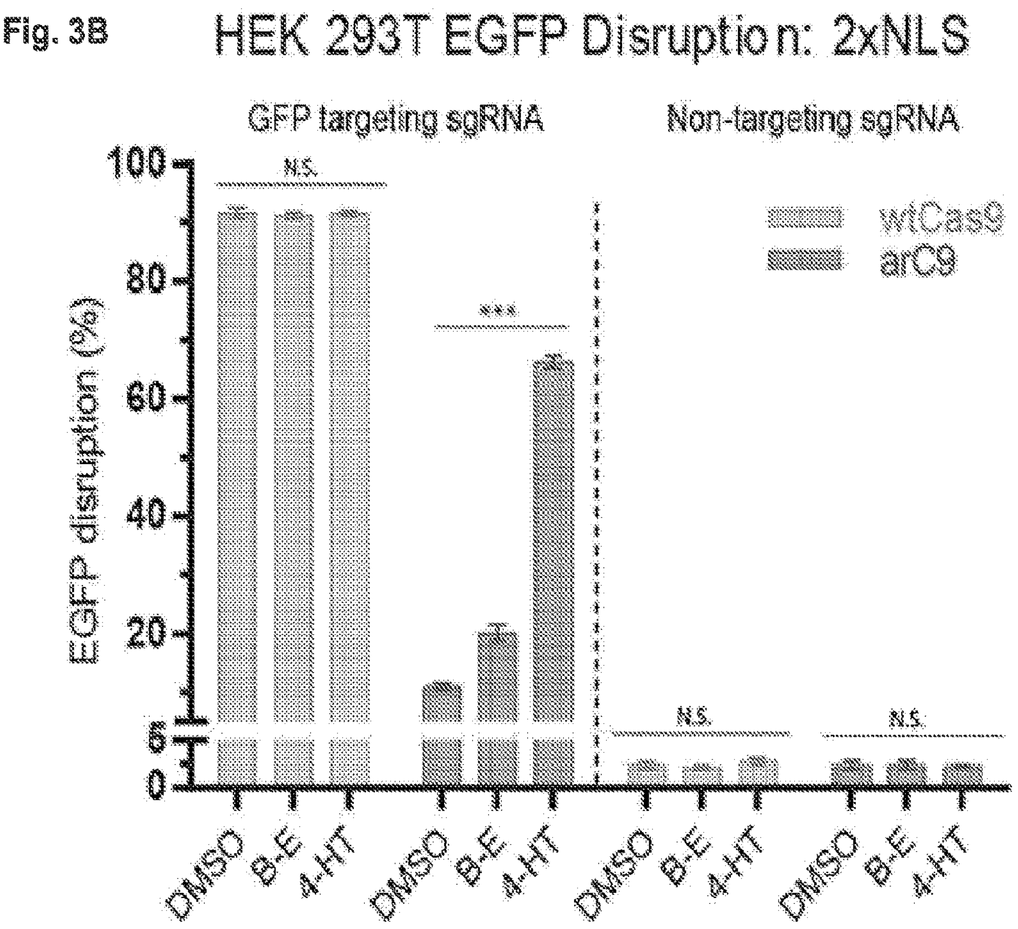

FIGS. 3A and 3B. (FIG. 3A) Schematic of the arC9:231 expression constructs and GFP disruption assay. (FIG. 3B) Quantification of EGFP disruption at 72 hours for Cas9 and arC9 with a N- and C-terminal nuclear localization signal (NLS) in triplicate. These data demonstrate a ~6 fold increase in EGFP disruption. Background activity of arC9 is 10.9±0.5% (S.D.) while EGFP disruption in the presence of 300 nM 4-HT increases to 66±1% (S.D.) Error bars represent one standard deviation of biological replicates. Transfection used five ng of plasmid DNA.

FIGS. 13A and 13B. ArC9 Human Plasmid. (FIG. 13A) Schematic description of the human arC9 expression plasmid with the 2×NLS (yellow) T2A cleavable linker and mCherry. Plasmid is originally derived from a pX330 variant. (FIG. 13B) Schematic of the human arC9 expression plasmid without NLS.

Figure 3C:
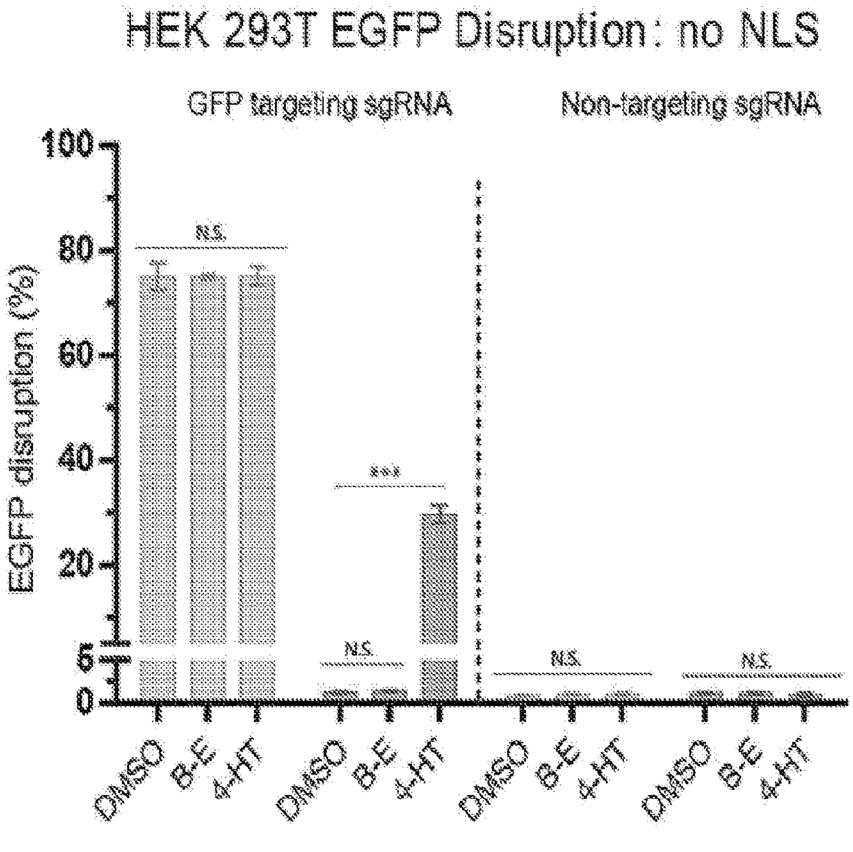

Therefore, the known ligand-dependent nuclear localization activity of ER-LBD was used in conjunction with the allosteric regulation of arC927. By removing the NLS from the arC9 construct it was possible to reduce its activity without 4-HT to background levels, while still maintaining robust activity with 4-HT. A dose-dependent response and maximum 24-fold increase in EGFP disruption in the presence of 300 nM 4-HT was observed (FIGS. 3C, D). The lack of background activity for arC9 suggests a strategy for reducing undesired cleavage by Cas9 because under all conditions WT Cas9 EGFP disruption activity remained >70% even without an NLS (FIG. 3C). Finally, a model to explain the dual dependence of arC9 activity on expression level and 4-HT was developed (FIG. 16). ArC9 clearly functioned as a 4-HT inducible nuclease in human cells, demonstrating that unbiased domain insertion can be used to engineer new functionalities into Cas9.

Figure 3D:
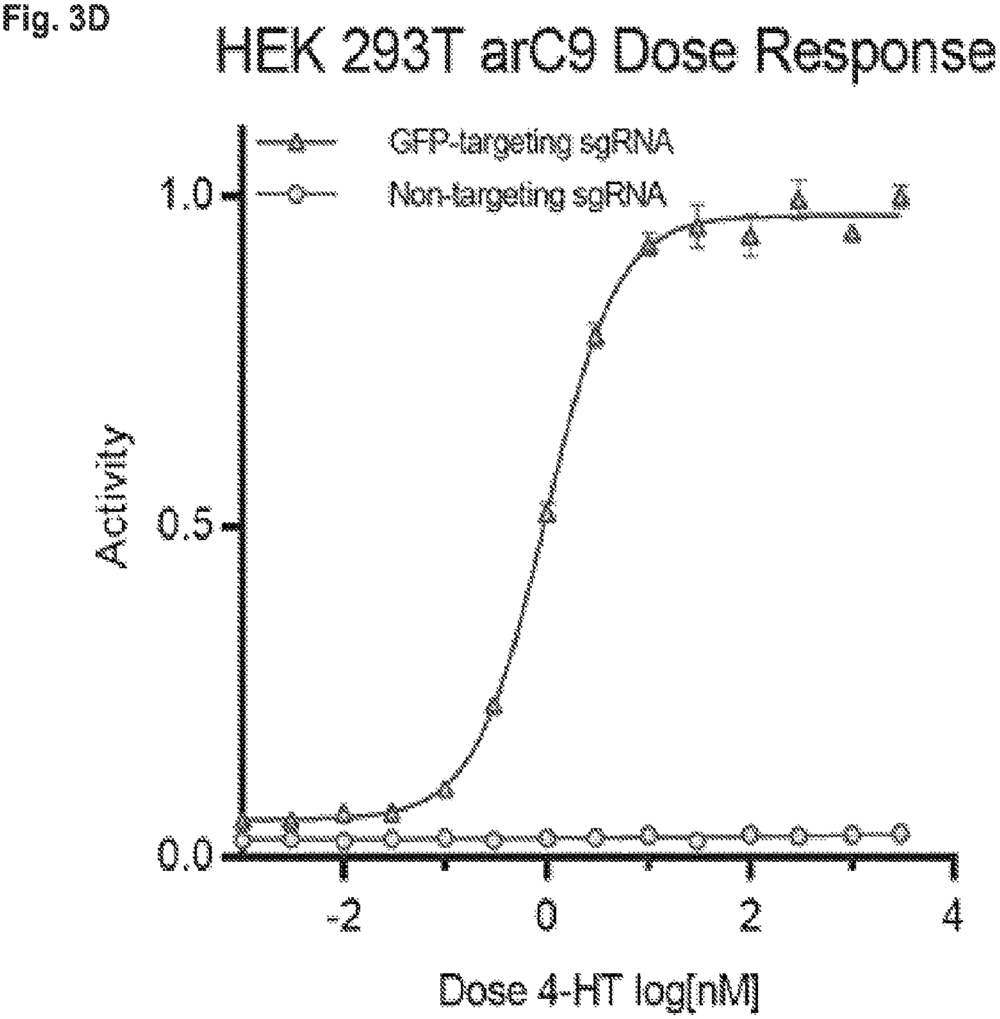
Figures 4A, 4B:
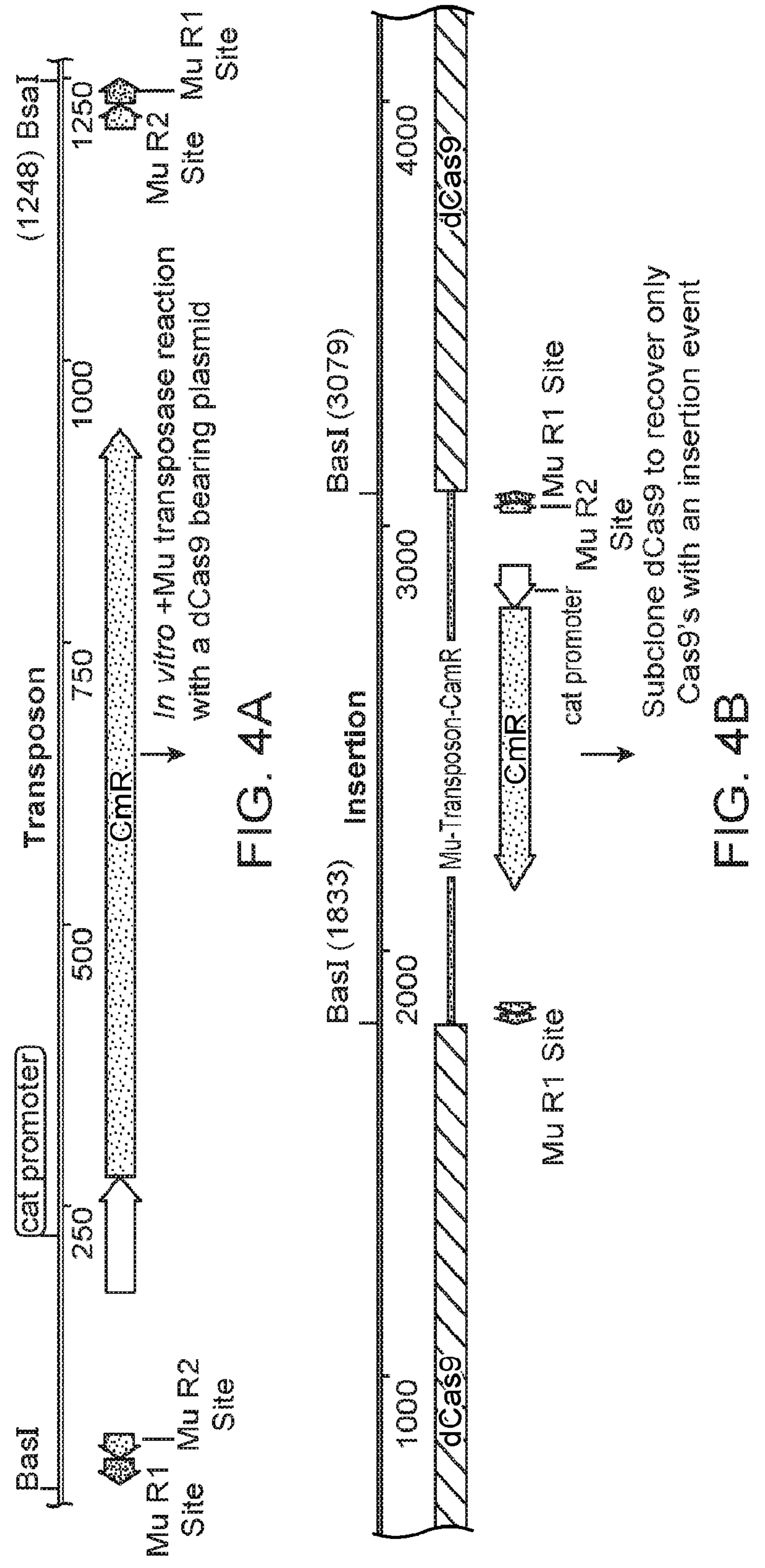
FIG. 4A-4D are a collection of figures showing construction of a transposition library, according to embodiments of the present disclosure.
Figure 4C:
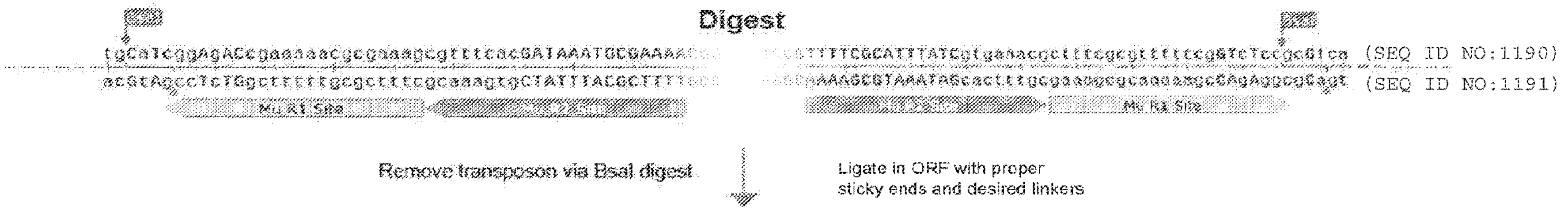
Figure 4D:
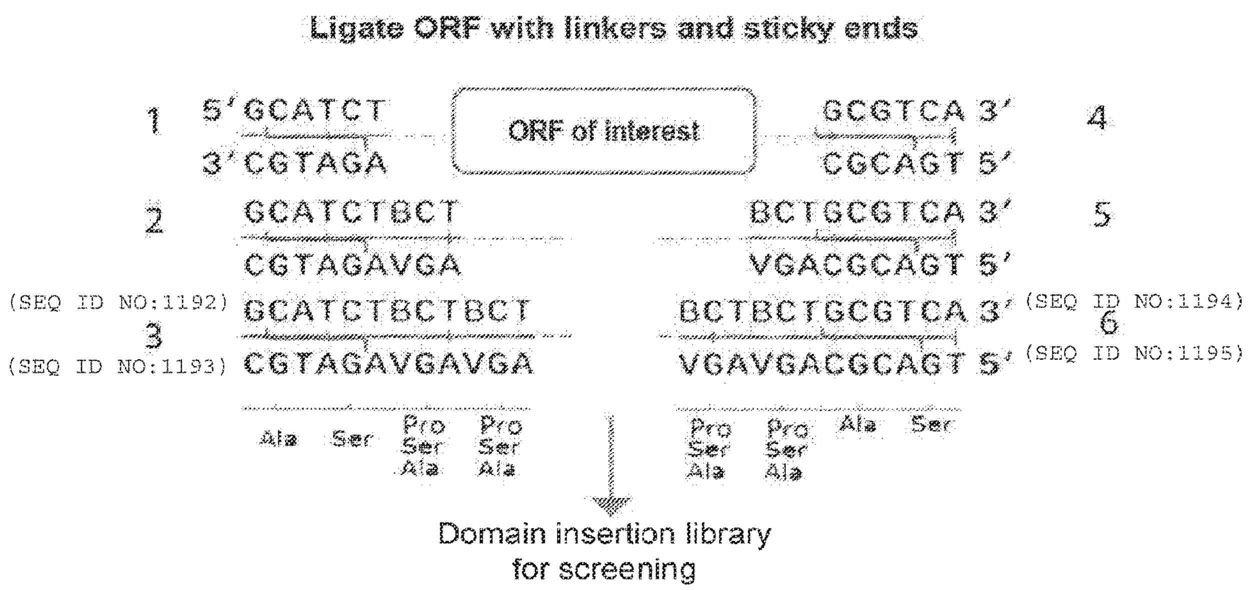

FIGS. 3C and 3D. (FIG. 3C) Quantification EGFP disruption at 72 hours for Cas9 and arC9 without an NLS. Background activity of arC9 is not significantly different from a non-targeting negative control. EGFP disruption in the presence of 4-HT increases to 30±2% (S.D.) this represents at least a 24-fold increase in arC9 activity in the presence of 300 nM 4-HT. Transfection used 50 ng of plasmid DNA (*p values <0.001). (FIG. 3**D) Dose response of arC9 w/o NLS normalized to maximum activity. IC50 is 1.0±0.2 nM (S.D).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11008555B2). An electronic copy of the "Sequence Listing" will also be available from the USPTO upon request and payment of the fee set forth in 37 CFR 1.19(b)(3).

What is claimed is:

1. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal, or that is immediately adjacent and N-terminal, to an amino acid residue corresponding to a residue selected from 3, 4, 42, 719, 721, 724, 940, 941, 944, 947, 952, 1010, 1011, 1012, 1015, 1016, 1022, 1026, 1027, 1031, 1034, 1046, 1047, 1049, 1050, 1051, 1052, 1053, 1054, 1056, 1058, 1061, 1062, 1063, 1064, 1065, 1068, 1070, 1071, and 1073 of the Cas9 protein set forth in SEQ ID NO: 5, wherein the heterologous polypeptide confers an inducible conformational change on the Cas9 fusion polypeptide, and wherein the Cas9 fusion polypeptide retains cleavage and/or binding activity relative to the activity of the Cas9 polypeptide without the inserted heterologous amino acid or heterologous polypeptide.

2. The Cas9 fusion polypeptide of claim 1, wherein the heterologous polypeptide is an estrogen receptor alpha ligand binding domain (ER-LBD).

3. A cell comprising the Cas9 fusion polypeptide of claim 1.

4. A nucleic acid comprising a nucleotide sequence that encodes the Cas9 fusion polypeptide of claim 1.

5. A cell comprising the nucleic acid of claim 4.

6. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal, or that is immediately adjacent and N-terminal, to an amino acid residue corresponding to a residue selected from 4, 193, 202, 204, 208, 209, 211, 228, 238, 460, 468, 588, 802, 804, 1027, 1052, 1058, 1064, 1071, 1156, 1191, 1243, 1244, and 1287 of the Cas9 protein set forth in SEQ ID NO: 5, wherein the Cas9 fusion polypeptide retains cleavage and/or binding activity relative to the activity of the Cas9 polypeptide without the inserted heterologous amino acid or heterologous polypeptide.

7. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal, or that is immediately adjacent and N-terminal, to an amino acid residue corresponding to a residue selected from 202, 204, 208, 209, 211, 468, 1027, 1052, 1058, and 1244 of the Cas9 protein set forth in SEQ ID NO: 5, wherein the Cas9 fusion polypeptide retains cleavage and/or binding activity relative to the activity of the Cas9 polypeptide without the inserted heterologous amino acid or heterologous polypeptide.

8. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted in a linker that is between the alpha helical and nuclease lobes at a position that is immediately adjacent and C-terminal, or that is immediately adjacent and N-terminal, to an amino acid residue corresponding to a residue selected from 715 and 717, of the Cas9 protein set forth in SEQ ID NO: 5, wherein the Cas9 fusion polypeptide retains cleavage and/or binding activity relative to the activity of the Cas9 polypeptide without the inserted heterologous amino acid or heterologous polypeptide.

9. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted in an HNH domain at a position that is immediately adjacent and C-terminal, or that is immediately adjacent and N-terminal, to an amino acid residue corresponding to a residue selected from 798, 801, 802, 804, 834, 868, and 890, of the Cas9 protein set forth in SEQ ID NO: 5, wherein the Cas9 fusion polypeptide retains cleavage and/or binding activity relative to the activity of the Cas9 polypeptide without the inserted heterologous amino acid or heterologous polypeptide.

10. A Cas9 fusion polypeptide comprising:

(a) a Cas9 polypeptide; and (b) a heterologous amino acid or heterologous polypeptide inserted internally within the Cas9 polypeptide, wherein the heterologous amino acid or heterologous polypeptide is inserted at a position that is immediately adjacent and C-terminal, or that is immediately adjacent and N-terminal, to an amino acid residue corresponding to residue 231 of the Cas9 protein set forth in SEQ ID NO: 5, wherein the Cas9 fusion polypeptide retains cleavage and/or binding activity relative to the activity of the Cas9 polypeptide without the inserted heterologous amino acid or heterologous polypeptide.

11. A method of binding a target nucleic acid, comprising:

contacting a target nucleic acid with: (i) a Cas9 fusion polypeptide of claim 1, and (ii) a Cas9 guide RNA.

12. The method of claim 11, wherein the Cas9 fusion polypeptide modulates transcription from the target nucleic acid, modifies the target nucleic acid, or cleaves the target nucleic acid.

13. The method of claim 11, wherein the method further comprises contacting the target nucleic acid with a donor template polynucleotide.

14. A method of binding a target nucleic acid, the comprising introducing into a cell: i) a DNA or RNA encoding a Cas9 fusion polypeptide of claim 1; ii) a DNA encoding a Cas9 guide RNA; or iii) a combination thereof.

* * * * *